United States Patent [19]

Santafianos et al.

[11] Patent Number: 5,369,123
[45] Date of Patent: Nov. 29, 1994

[54] NITROGEN-SUBSTITUTED MEVINIC ACID DERIVATIVES USEFUL AS HMG-COA REDUCTASE INHIBITORS

[75] Inventors: Dinos P. Santafianos, Maplewood; Kathleen M. Poss, Lawrenceville, both of N.J.; Eric M. Gordon, Palo alto, Calif.; Peggy J. McCann, West Trenton, N.J.

[73] Assignee: E. R. Squibb & Sons, Inc., Princeton, N.J.

[21] Appl. No.: 958,849

[22] Filed: Oct. 9, 1992

[51] Int. Cl.$^5$ .............. A61K 31/40; A61K 31/365; C07D 309/30; C07C 69/74

[52] U.S. Cl. .................. 514/428; 514/429; 514/460; 514/510; 548/517; 548/579; 549/292; 560/119

[58] Field of Search ............ 548/517, 579; 549/292; 560/119; 514/428, 429, 460, 510

[56] References Cited

U.S. PATENT DOCUMENTS

| | | | |
|---|---|---|---|
| 3,983,140 | 9/1976 | Endo et al. | 260/343.5 |
| 4,346,227 | 8/1982 | Terahara et al. | 560/119 |
| 4,866,186 | 9/1989 | Thompson et al. | 549/292 |
| 4,921,974 | 5/1990 | Duggan | 549/214 |

FOREIGN PATENT DOCUMENTS

| | | |
|---|---|---|
| 0137444A2 | 4/1985 | European Pat. Off. . |
| 0349063A2 | 1/1990 | European Pat. Off. . |
| 0465265 | 1/1992 | European Pat. Off. . |

OTHER PUBLICATIONS

Rasmussen et al., "A Versatile Synthesis of Novel N,N,N″-Trisubstituted Guanidines", *Synthesis*, 460–466 (1988).
Kim et al., "Monosubstituted Guanidines From Primary Amines And Aminoiminomethanesulfonic Acid", *Tetrahedron Lett.*, 29, 3183–3186 (1988).
Atwal et al., "A Facile Synthesis of Cyanoguanidines From Thioureas", *Tetrahedron Lett.*, 30, 7313–7316 (1989).
Poss et al., "A Mild and Efficient Method For The Preparation of Guanidines", Abstract ORGN 424, 203rd Meeting of the American Chemical Society (Apr., 1992).
Sharts, C. M., "N,N-Difluoroalkylamines by Direct Fluorination of Alkylamines", *J. Org. Chem.*, 33(3), 1008–1011 (1968).
Grakauskas et al., "Direct Fluorination of Substituted Carbamates", *J. Org. Chem.*, 34(10), 2840–2845 (1969.
Wiesboeck et al., "The Preparation of N,N-Difloroalkylamines By Aqeous Fluorination", *Tetrahedron*, 26, 837–840 (1970).
Grakauskas et al., "Direct Fluorination of Amides", *J. Org. Chem.*, 35(5), 1545–1549 (1970).
Balko et al., "Halocyclizations: The Cyclization of Heterocyclic Olefinic Amides and Ureas", *Tetrahedron Lett.*, 30(16), 2045–2048 (1989).

*Primary Examiner*—C. Warren Ivy
*Assistant Examiner*—Ba K. Trinh
*Attorney, Agent, or Firm*—Suzanne E. Babajko

[57] ABSTRACT

Novel nitrogen-substituted mevinic acid derivatives which inhibit the activity of HMG-CoA reductase. Pharmaceutical compositions, and methods of use for the treatment or prevention of hypercholesterolemia, atherosclerosis, hyperlipoproteinaemia and hyperlipidemia are provided, as are novel methods for preparation and intermediate compounds.

11 Claims, No Drawings

NITROGEN-SUBSTITUTED MEVINIC ACID DERIVATIVES USEFUL AS HMG-COA REDUCTASE INHIBITORS

FIELD OF THE INVENTION

The present invention relates to new nitrogen-substituted mevinic acid derivatives which inhibit the activity of 3-hydroxy-3-methyl-glutaryl-coenzyme A (HMG-CoA) reductase, to pharmaceutical compositions containing such compounds, to methods for preparing, and new intermediates formed in the preparation of such compounds, and to methods of using such compounds.

SUMMARY OF THE INVENTION

The instant invention provides compounds having the following formula I:

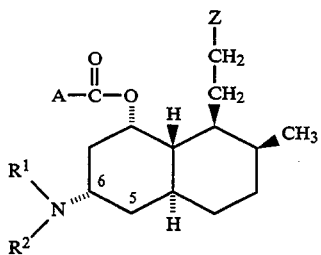

where
A is alkyl or aryl;
Z is the open chain moiety:

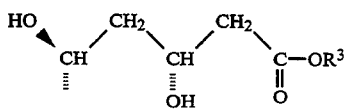

or Z is the lactone moiety:

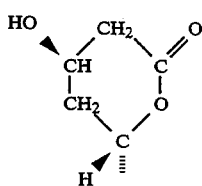

(i) $R^1$ and $R^2$ are each independently selected from:
(1) hydrogen;
(2) alkyl;
(3) aryl;
(4) acyl;
(5) $R^5$—$SO_2$—;
(6) $(R^4)(R^6)N$—$SO_2$—;
(7) $(R^4)(R^6)N$—SO—;

(8) 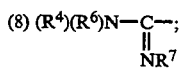

(9) $(R^4)(R^6)N$—C(O)—;
(10) $(R^5)O$—C(O)—;
(11) alkenyl;
(12) alkynyl;
(13) carbocyclo;
(14) heterocyclo;
(15) $R^5$—SO—; or
(16) fluoro; or (ii) $R^1$ and $R^2$, together with the nitrogen atom to which they are bonded, form a heterocyclo group;

$R^3$ is:
(1) hydrogen;
(2) a pharmaceutically acceptable cation; or
(3) a moiety which, together with the atoms to which it is bonded, forms a pharmaceutically acceptable ester group;

$R^4$ and $R^6$ are each independently selected from:
(1) hydrogen;
(2) alkyl;
(3) aryl;
(4) carbocyclo;
(5) alkenyl;
(6) alkynyl; or
(7) heterocyclo;

$R^5$ is selected from:
(1) alkyl;
(2) aryl;
(3) carbocyclo;
(4) alkenyl;
(5) alkynyl; or
(6) heterocyclo; and $R_7$ is selected from:
(1) hydrogen;
(2) alkyl;
(3) aryl;
(4) cyano;
(5) nitro; or
(6) —$COOR^5$;

and N-oxides and/or salts, preferably pharmaceutically acceptable salts, thereof.

The compounds of the instant invention are inhibitors of the enzyme 3-hydroxy-3-methylglutaryl coenzyme A reductase (HMG-CoA reductase) and are thus inhibitors of cholesterol biosynthesis (hypocholesterolemic agents). The instant invention therefore provide methods and pharmaceutical compositions for reducing or maintaining plasma cholesterol levels. The instant invention also provides methods and pharmaceutical compositions for the treatment and/or prevention of atherosclerosis, hyperlipidemia, and hyperlipoproteinaemia. Further provided are the novel methods and intermediates produced in the preparation of the inventive compounds.

The inventive compounds are advantageous in that they raise the plasma ratio of high density lipoprotein (HDL) cholesterol to low density lipoprotein (LDL) cholesterol.

Use of the inventive compounds as anti-fungal and anti-cancer agents, as well as in the treatment of gallstones, is also contemplated in the instant invention.

DETAILED DESCRIPTION OF THE INVENTION

The terms "alk", "alkan" or "alkyl", as employed herein alone or as part of another group, denote both straight and branched chain, optionally substituted radicals, preferably containing 1 to 8 carbons in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, and the various branched chain isomers thereof The terms "alk", "alkan", or "alkyl" as used herein, therefore, denote both unsubstituted as well as substituted moieties. Exemplary substituents may include, for example, one or more, such as 1, 2 or 3, of the following: halo-substituents (F, Br, Cl or I), trihalomethyl substituents (e.g. $CF_3$), alkoxy substituents, aryl substituents such as unsubstituted aryl substituents (e.g. to form a benzyl group), alkyl-aryl substituents, or haloaryl substituents, cycloalkyl substituents such as unsubstituted cycloalkyl substituents, fluoro-substituted cycloalkyl substituents, or alkylcycloalkyl substituents, carbocyclo-oxy substituents, hydroxy substituents, amino substituents, mono- or diarylamino substituents, mono- or dialkylamino substituents, alkanoylamino substituents, arylcarbonylamino substituents, nitro substituents, cyano substituents, thiol substituents, arylthio substituents, alkylthio substituents, alkylsulfinyl substituents, arylsulfinyl substituents, alkylsulfonyl substituents, arylsulfonyl substituents, alkylcarbonyloxy substituents, alkenyl substituents such as unsubstituted alkenyl substituents (e.g. allyl substituents) fluoro-substituted alkenyl substituents or arylalkenyl substitutents, alkenyloxy substituents, alkynyloxy substituents, alkynyl substituents such as unsubstituted alkynyl substituents or fluoro-substituted alkynyl substituents, aryloxy substituents, heterocyclo substituents such as unsubstituted heterocyclo or fluoro-substituted heterocyclo substituents, heterocyclo-oxy substituents, carboxyl substituents, alkoxycarbonyl substituents, cycloalkyloxycarbonyl substituents, alkenyloxycarbonyl substituents, alkynyloxycarbonyl substituents, aryloxycarbonyl substituents, heterocyclo-oxycarbonyl substituents, formyloxy substituents, cycloalkanoyloxy substituents, alkenoyloxy substituents, alkynoyloxy substituents, heterocycloyloxy substituents, mono- or dicycloalkylamino substituents, mono- or dialkenylamino substituents, mono- or dialkynylamino substituents, mono- or diheterocycloamino substituents, cycloalkylcarbonyl amino substituents, alkenylcarbonylamino substituents, alkynylcarbonylamino substituents, heterocyclocarbonylamino substituents and/or arylcarbonyloxy substituents. The term "lower alkyl" as employed herein denotes such optionally substituted groups as described above for alkyl containing 1 to 6 carbon atoms in the normal chain.

Preferred alkyl groups include the following:
(i) unsubstituted lower alkyl groups, especially methyl;
(ii) hydroxy-substituted lower alkyl groups, especially groups of the formula —$(CH_2)_n$—OH where n is from 1 to 5 such as hydroxymethyl, 2-hydroxyethyl or 3-hydroxypropyl;
(iii) alkoxy-substituted lower alkyl groups, especially groups of the formula $R^8$—O—$(CH_2)_n$— where n is from 1 to 5, especially n=1, and $R^8$ is alkyl, particularly unsubstituted lower alkyl such as methyl;
(iv) lower alkyl groups substituted by amino or substituted amino groups, especially groups of the formula $(R^9)(R^{10})$N—$(CH_2)_n$— where n is from 1 to 5 and $R^9$ and $R^{10}$ are each independently hydrogen, alkyl or aryl, particularly 2-hydroxyethyl, 2-acetyloxyethyl, unsubstituted lower alkyl such as methyl, or unsubstituted phenyl, biphenyl or naphthyl;
(v) groups of the formula $R^5$—S(O)$_m$—$(CH_2)_n$— where n is from 1 to 5, m is 0, 1 or 2, especially n=1 and m=2, and $R^5$ is alkyl or aryl, particularly unsubstituted lower alkyl such as methyl, or unsubstituted phenyl, biphenyl or naphthyl;
(vi) alkylcarbonyloxy-substituted lower alkyl groups, especially groups of the formula $R^8$—C(O)—O—$(CH_2)_n$— where n is from 1 to 5, especially n=1, and $R^8$ is alkyl, particularly unsubstituted lower alkyl such as methyl;
(vii) aryloxy-substituted lower alkyl groups, especially groups of the formula $R^{11}$—O—$(CH_2)_n$— where n is from 1 to 5 and $R^{11}$ is aryl, particularly unsubstituted phenyl, biphenyl or naphthyl; and
(viii) arylcarbonyloxy-substituted lower alkyl groups, especially groups of the formula $R^{11}$—C(O)—O—$(CH_2)_n$— where n is from 1 to 5 and $R^{11}$ is aryl, particularly unsubstituted phenyl, biphenyl or naphthyl.

The term "alkenyl", as employed herein alone or as part of another group, denotes such optionally substituted groups as described above for alkyl, further containing at least one carbon to carbon double bond. Those groups having 2 to 8 carbon atoms are preferred. Exemplary alkenyl groups include vinyl or allyl.

The term "alkynyl", as employed herein alone or as part of another group, denotes such optionally substituted groups as described above for alkyl, further containing at least one carbon to carbon triple bond. Those groups having 2 to 8 carbons atoms are preferred. Propargyl is an exemplary alkynyl group.

The term "carbocyclo", as employed herein alone or as part of another group, denotes a saturated or partially unsaturated, optionally substituted homocyclic carbon ring system, particularly an optionally substituted cycloalkyl ring, or an optionally substituted cycloalkenyl ring. Such cyclic groups preferably contain from 1 to 3 rings and from 3 to 12, most preferably from 3 to 8 carbons per homocyclic ring. The term "carbocyclo", therefore, denotes unsubstituted as well as substituted groups. Exemplary unsubstituted groups include saturated moieties such as cyclopropyl, cyclobutyl, cyclopentyl, cyclohexyl, cycloheptyl, cyclooctyl, cyclodecyl, cyclododecyl, and adamantyl, and partially unsaturated moieties such as cyclohexadienyl. Exemplary optional substituents for the carbocyclo groups may include one or more alkyl groups as described above, or one or more of those groups described above as alkyl substituents.

The terms "ar" or "aryl", as employed herein alone or as part of another group, denote optionally substituted, homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. The terms "ar" or "aryl" as used herein, therefore, denote both unsubstituted as well as substituted groups. Exemplary optional substituents for these groups may include one or more alkyl groups as described above, or one or more of those groups described above as alkyl substituents. Such substituents may include, for example, methylenedioxy where the methylene group may be substituted by lower alkyl group(s), arylalkenyl group(s), and/or alkylthio group(s).

The terms "halogen" or "halo", as employed herein alone or as part of another group, denote chlorine, bromine, fluorine, and iodine, with chlorine or fluorine being preferred.

The term "heterocyclo", as employed herein alone or as part of another group, denotes optionally substituted, fully saturated or unsaturated, mono-cyclic or bicyclic, aromatic or nonaromatic cyclic groups having at least one heteroatom in at least one ring, and preferably having 5 to 7 atoms in each ring. Exemplary heterocyclo groups may have 1 or 2 oxygen atoms, 1 or 2 sulfur atoms, and/or 1 to 4 nitrogen atoms in a ring. The term "heterocyclo" as used herein, therefore, denotes unsubstituted as well as substituted groups. The heterocyclo groups may optionally be substituted, for example, with one or more alkyl groups as described above, or one or more of those groups described above as alkyl substituents.

Exemplary heterocyclo groups include 2- and 3-thienyl, 2- and 3-furyl, pyrrolyl (e.g. 2- and 3-pyrrolyl), pyridyl (e.g. 2-, 3- and 4-pyridyl), imidazolyl (e.g. 2-, 4- and 5-imidazolyl), pyrrolidinyl (e.g. 1-, 2- and 3-pyrrolidinyl), piperidinyl (e.g. 2-, 3- and 4-piperidinyl), azepinyl (e.g. 2-, 3- and 4-azepinyl), indolyl (e.g. 4-, 5-, 6- or 7-indolyl), isoindolyl (e.g. 4-, 5-, 6- or 7-isoindolyl), quinolinyl (e.g. 5-, 6-, 7- or 8-quinolinyl), isoquinolinyl (e.g. 5-, 6-, 7- or 8-isoquinolinyl), benzothiazolyl (e.g. 4-, 5-, 6- or 7-benzothiazolyl), benzoxazolyl (e.g. 4-, 5-, 6- or 7-benzoxazolyl), benzimidazolyl (e.g. 4-, 5-, 6-, or 7-benzimidazolyl), benzoxadiazolyl (e.g. 4-, 5-, 6- or 7-benzoxadiazolyl), and benzofurazanyl (e.g. 4-, 5-, 6- or 7-benzofurazanyl).

The term "acyl", as employed herein alone or as part of another group, denotes all organic moieties that may be derived from an organic acid (i.e., organic compounds containing the carboxylic acid group —COOH) by exchange of the hydroxyl group. Particularly preferred such groups are those of the formula

where $R^{12}$ is hydrogen, alkyl, aryl, cycloalkyl, alkenyl, alkynyl, heterocyclo or cycloalkenyl, where the aforementioned groups are as defined above, including the optional substituents thereof.

The term "salt(s)", as employed herein, refers to acidic and/or basic salts formed with inorganic and/or organic acids and bases. Basic salts are preferred. Exemplary salts include alkali metal salts such as lithium, sodium and potassium salts, alkaline earth metal salts such as calcium and magnesium salts, salts with organic bases, for example, amine salts such as dicylohexylamine salt, benzathine, N-methyl-D-glucamine, hydrabamine salts, salts with amino acids such as arginine and lysine, acetate, tartrate or citrate salts, and equivalent such salts. The nontoxic, pharmaceutically acceptable salts are preferred, although other salts are also useful, for example, in isolation or purification steps which may be employed during preparation. Zwitterions (internal or inner salts) are also included within the term "salt(s)" as used herein. Ammonium salts such as alkylammonium salts are also included within the term "salt(s)" as used herein. Particularly preferred ammonium salts are those having the formula:

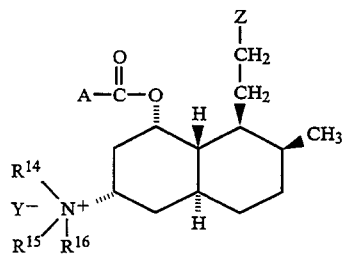

where A and Z are as defined in formula I; $R^{14}$, $R^{15}$ and $R^{16}$ are independently selected from hydrogen, alkyl, aryl, alkenyl, alkynyl, carbocyclo or heterocyclo, and especially, are all independently selected alkyl groups such as methyl; and Y is a pharmaceutically acceptable counterion such as halo (e.g. Cl, Br or I), hydroxyl, acetate, citrate or tartrate.

The term "pharmaceutically acceptable cation", as employed herein, denotes non-toxic cations of basic salts, exemplified by those described above.

The term "pharmaceutically acceptable ester", as employed herein, denotes non-toxic groups of the formula —COOR$^5$.

Reference to a compound or salt herein is defined to include solvates, such as hydrates, thereof unless otherwise indicated.

The compounds of formula I have designated stereoisomeric configurations at certain chiral centers as indicated therein. The compounds of the invention may, for example, be substantially free of other stereoisomers or admixed with compounds of differing stereoisomeric configurations at those chiral centers. In addition, all stereoisomers of chiral centers of unspecified configuration are contemplated, for example, in admixture (e.g. racemates) or substantially free of other stereoisomers.

Preferred Groups

In the compounds of the present invention, the group A is preferably:

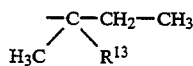

where $R^{13}$ is hydrogen, cycloalkyl, aryl or alkyl (e.g. unsubstituted alkyl or aralkyl), especially hydrogen or unsubstituted lower alkyl such as methyl.

Z is preferably the lactone ring or open chain group defined in formula I where, in the latter case, $R^3$ is hydrogen, alkyl, NH$_4^+$, alkylammonium or an alkali metal.

$R^1$ and $R^2$ are preferably, independently, hydrogen; unsubstituted lower alkyl such as methyl or ethyl; one of the aforementioned preferred alkyl groups (ii) through (viii), such as 2-hydroxyethyl; $R^5$—SO$_2$— where $R^5$ is unsubstituted lower alkyl such as methyl; trihalomethylcarbonyl such as F$_3$C—C(O)—; (trifluoroacetylamino)acetyl; alkylcarbonyl where the alkyl group of said alkylcarbonyl is one of the aforementioned preferred alkyl groups (i) through (viii); optionally substituted phenylcarbonyl such as benzoyl, aminophenylcarbonyl and (trifluoroacetylamino)benzoyl; (R$^5$)O—C(O)— where R$^5$ is unsubstituted lower alkyl such as methyl; (R$^4$)(R$^6$)N—C(O)— where R$^4$ and R$^6$ are independently hydrogen or unsubstituted lower alkyl such as methyl; formyl; and (R$^4$)(R$^6$)N—SO$_2$— where R$^4$ and R$^6$ are independently hydrogen or unsubstituted lower alkyl such as methyl. When R¹ and R², together with the nitrogen atom to which they are bonded, form a heterocyclo group, that group is preferably an unsubstituted or substituted pyrrolidinyl group. Most preferably, R¹ and R² are both independently selected from unsubstituted lower alkyl groups, especially where R¹ and R² are both methyl.

Preferred N-oxides are those at the nitrogen atom bearing the groups R¹ and R²:

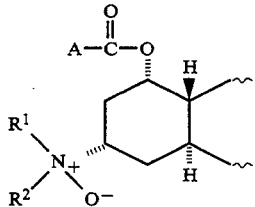

especially those where R¹ and R² are lower alkyl such as methyl.

Particularly preferred compounds of the present invention are:

[1S-[1α,3α,4aα,7β,8β(2S*, 4S*),8aβ]]-2,2-dimethylbutanoic acid, 3-[(methylsulfonyl)amino]-decahydro-7-methyl-8-[2-(tetrahydro-4-hydroxy-6-oxo-2H-pyran-2-yl)ethyl]-1-naphthalenyl ester;

[1S-[1α(βS*,δS*),2α,4β,6β,8β,8aα]]-8-(2,2-dimethyl-1-oxobutoxy)decahydro-β,δ-dihydroxy-2-methyl-6-[(methylsulfonyl)amino]-1-naphthaleneheptanoic acid;

[1S-[1α,3α,4aα,7β,8β(2S*,4S*),8aβ]]-2,2-dimethylbutanoic acid, 3-[[(methylsulfonyl)acetyl]amino]-decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)decahydro-β,δ-dihydroxy-2-methyl-6-[[(methylsulfonyl)acetyl]amino]-1-naphthaleneheptanoic acid;

[1S-[1α,3α,4aα,7β,8β(2S*,4S*),8aβ]]-2,2-dimethylbutanoic acid, 3-[(methoxyacetyl)amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)decahydro-β,δ-dihydroxy-6-[(methylacetyl)amino]-2-methyl-1-naphthaleneheptanoic acid;

[1S-[1α,3α,4aα,7β,8β(2S*,4S*),8aβ]]-2,2-dimethylbutanoic acid, 3-(benzoylamino)decahydro-7-methyl-8-[2-(tetrahydro-4-hydroxy-6-oxo-2H-pyran-2-yl)-ethyl]-1-naphthalenyl ester;

[1S-[1α(βS*,δS*),2α,4aβ,6β,8β,8aα]]-6-(benzoylamino)-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[(acetoxyacetyl)amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4β,6β,8β,8aα]]-8-(2,2-dimethyl-1-oxobutoxy)decahydro-β,δ-dihydroxy-6-[(hydroxyacetyl)amino]-2-methyl-1-naphthaleneheptanoic acid;

[1S-[1α,3α,4aα,7β,8β(2S*,4S*),8aβ]]-2,2-dimethylbutanoic acid, 3-[(trifluoroacetyl)amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-amino-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[(methoxycarbonyl)amino]-decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)decahydro-β,δ-dihydroxy-6-](methoxycarbonyl)amino]-2-methyl-1-naphthaleneheptanoic acid;

[1S-[1α(βS*,δS*),2α,4aβ,6β,8β,8aα]]-6-[[(methylamino)carbonyl]amino]-8-(2,2-dimethyl-1-oxobutoxy)decahydro-β,δ-dihydroxy-2-methyl-1-naphthaleneheptanoic acid;

[1S-[1α(βS*,δS*),2α,4aβ,6β,8β,8aα]]-6-[[(dimethylamino)carbonyl]amino]-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-(acetylamino)decahydro-7-methyl-8-[2-(tetrahydro-4-hydroxy-6-oxo-2H-pyran-2-yl)ethyl]-1-naphthalenyl ester;

1S-[1α(βS*,δS*),2α,4aβ,6β,8β,8aα]]-6-(acetylamino)-8-(2,2-dimethyl-1-oxobutoxy)-decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-(formylamino)decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)-6-(formylamino)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[[(dimethylamino)-sulfonyl]amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-[[(dimethylamino)sulfonyl]amino]-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[[(methylamino)sulfonyl]amino]-decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)decahydro-β,δ-dihydroxy-2-methyl-6-[[(methylamino)sulfonyl]amino]-1-naphthaleneheptanoic acid;

[1S-[1α,3α,4aα,7β,8β(2S*,4S*),8aβ]]-2,2-dimethylbutanoic acid, 3-(dimethylamino)decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-(dimethylamino)-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-(acetylmethylamino)decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-(acetylmethylamino)-8-(2,2-dimethyl-1-oxobutoxy)-decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[(trifluoroacetyl)methylamino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)decahydro-β,δ-dihydroxy-2-methyl-6-(methylamino)-1-naphthaleneheptanoic acid;

[1S-[1α,3α,4aα,7β,8β(2S*,4S*),8aβ]]-2,2-dimethylbutanoic acid, 3-(diethylamino)decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-(diethylamino)-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[(2-hydroxyethyl)methylamino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)decahydro-β,δ-dihydroxy-6-[(2-hydroxyethyl)methylamino]-2-methyl-1-naphthaleneheptanoic acid;

[1S-[1α,3α,4aα,7β,8β(2S*,4S*),8aβ]]-2,2-dimethylbutanoic acid, 3-aminodecahydro-7-methyl-8-[2-(tetrahydro-4-hydroxy-6-oxo-2H-pyran-2-yl)ethyl)-1-naphthalenyl ester;

[1S-[1α,3α,4aα,7β,8β(2S*,4S*),8aβ]]-2,2-dimethylbutanoic acid, 3-(dimethylamino)decahydro-7-methyl-8-[2-(tetrahydro-4-hydroxy-6-oxo-2H-pyran-2-yl)ethyl]-1-naphthalenyl ester;

[1S-[1α,3α,4aα,7β,8β(2S*,4S*), 8aβ]]-2,2-dimethylbutanoic acid, 3-(dimethylamino)decahydro-7-methyl-8-[2-(tetrahydro-4-hydroxy-6-oxo-2H-pyran-2-yl)ethyl)-1-naphthalenyl ester;

[1S-[1α,3α,4aα,7β,8β(2S*,4S*),8aβ]]-2,2-dimethylbutanoic acid, 3-(trimethylammonio)decahydro-7-methyl-8-[2-(tetrahydro-4-hydroxy-6-oxo-2H-pyran-2-yl)ethyl]-1-naphthalenyl ester, iodide;

[1S-[1α(βS*,δS*),2α,4aβ,6β,8β,8aα]]-8-(2,2-dimethyl-1-oxobutoxy)decahydro-β,δ-dihydroxy-2-methyl-2-methyl-6-(trimethylammonio)-1-naphthaleneheptanoic acid, methyl ester, iodide;

[1S-[1α(βS*,δS*),2α,4aβ,6β,8β,8aα]]-8-(2,2-dimethyl-1-oxobutoxy)decahydro-β,δ-dihydroxy-2-methyl-6-(trimethylammonio)-1-naphthaleneheptanoic acid, hydroxide;

[1S-[1α,3α,4aα,7β,8β(2S*,4S*),8aβ]]-2,2-dimethylbutanoic acid, 3-[[4-[(trifluoroacetyl)amino]benzoyl]amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-[(4-aminobenzoyl)amino]-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[[[(trifluoroacetyl)amino]acetyl]amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-[(aminoacetyl)amino]-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[[(dimethylamino)acetyl]amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-[[(dimethylamino)acetyl]amino]-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S,),8aβ]]-2,2-dimethylbutanoic acid, 3-[[[(2-hydroxyethyl)[2-(acetyloxy)ethyl]amino]acetyl]amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-[[[bis(2-hydroxyethyl)amino]acetyl]amino]-8-(2,2-dimethyl-1-oxobutoxy)decahydro-β,δ-dihydroxy-2-methyl-1-naphthaleneheptanoic acid;

[1S-[1α(βS*,δS*),2α,4aβ,6β,8β,8aα]]-6-(dimethylamino)-8-(2,2-dimethyl-1-oxobutoxy)decahydro-β,δ-dihydroxy-2-methyl-1-naphthaleneheptanoic acid, N-oxide;

[1S-[1α,3α,4aα,7β,8β(2S*,4S*),8aβ]]-2,2-dimethylbutanoic acid, 3-(1-pyrrolidinyl)decahydro-7-methyl-8-[2-(tetrahydro-4-hydroxy-6-oxo-2H-pyran-2-yl)ethyl]-1-naphthalenyl ester; and

[1S-[1α(βS*,δS*),2α,4aβ,6β,8β,8aα]]-8-(2,2-dimethyl-1-oxobutoxy)decahydro-β,δ-dihydroxy-2-methyl-6-(1-pyrrolidinyl)-1-naphthaleneheptanoic acid; and pharmaceutically acceptable salts, such as the monolithium salts, thereof.

The compounds of the instant invention may be obtained by the following methods of the invention.

Reaction Scheme

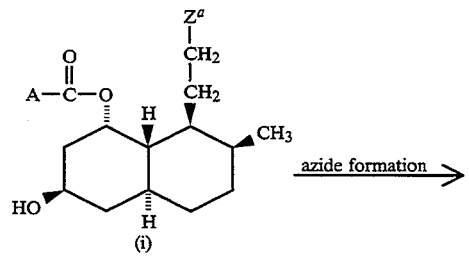

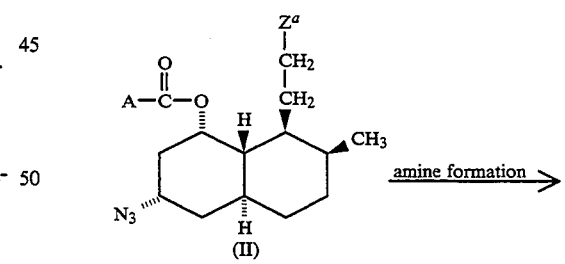

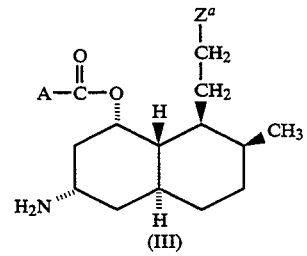

For $R^1 = R^2$ = hydrogen:

(III) →  1. deprotection
        2. optional
           ring opening

-continued
Reaction Scheme

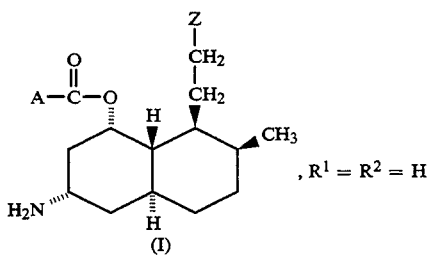
, R¹ = R² = H (I)

For R¹ and/or R² other than hydrogen:

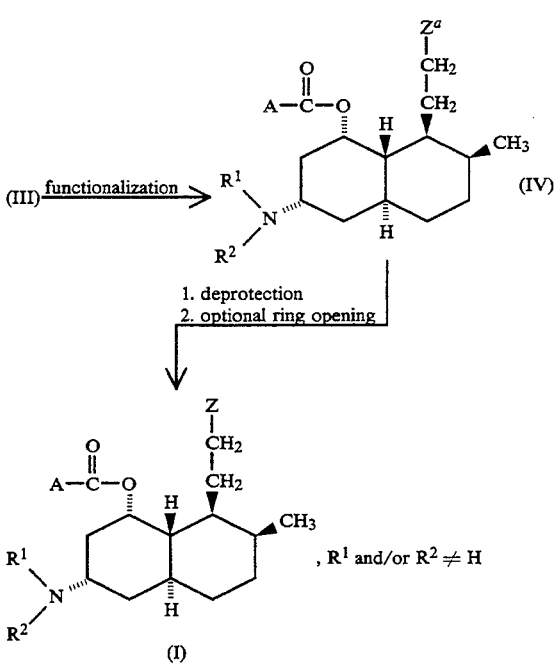

Compounds of the instant invention may be prepared according to the above Reaction Scheme.

Starting Material, Compound (i)

The above Reaction Scheme begins by converting the 6-position hydroxyl group of a compound (i) to an azide group. In compound (i), the group A is defined as in formula I, and the group $Z^a$ is:

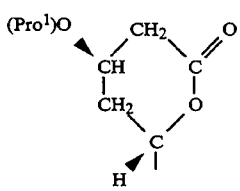

where "Pro¹" is a protecting group which may be cleaved in subsequent steps to for a hydroxyl group without destruction of the remainder of the molecule. Exemplary Pro¹ groups include benzyloxymethyl (which is preferred), p-methoxybenzyloxymethyl, tetrahydrylpyranyloxy, acyl, such as lower alkylcarbonyl, and the like.

Compounds of the formula (i) may be prepared by a method such as that described for the preparation of compounds (i) having the preferred group A:

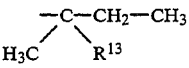

in European Patent Publication No. 0,465,265, incorporated herein by reference. Compounds of the formula (i) having different groups A may be prepared by analogous procedures. See also European Patent publication No. 0,349,063.

Azide Formation

The starting material (i) is converted to the intermediate II by contacting the compound (i) with an azide group-forming agent. Any compound or compounds capable of converting the hydroxyl group of compound (i) to the azide group of compound II may be employed as the azide group-forming agent. It is preferred to contact the compound (i) with (a) lithium azide and carbon tetrabromide, (b) lithium azide and bromocarbontrichloride; (c) tetramethyl guanidium azide and carbon tetrabromide; or (d) hydrazoic acid, di-isopropylazodicarboxylate; followed by contact with triphenylphosphine.

Azide group formation is preferably conducted at a temperature of from about 0° C. to about 25° C., and at a pressure of about 1 atm. The reaction may, for example, be completed over the course of about 36 hours to about 48 hours, and is preferably conducted under an atmosphere of argon.

Molar ratios of the preferred azide group-forming compounds to the starting compound (i) are preferably as follows: about 7:1 for lithium azide; about 5:1 for tetramethyl guanidium azide; about 3:1 for carbon tetrabromide or bromocarbontrichloride; and about 2.5:1 for triphenylphosphine. Solvents are preferably employed which are selected from organic solvents such as dimethylformamide. Amounts of solvents are preferably those where the compound (i) starting material is from about 6 to about 8% by weight, based on the combined weight of solvent and compound (i).

The method of converting a compound (i) to a compound II, and the compounds II, are novel.

Amine Formation

The azide compound II may then be converted to the intermediate III by reduction of the azide group of the former to the amine group of the latter. Any reducing agent capable of the aforementioned conversion may be employed. It is preferred to contact the compound II with triphenylphosphine.

Amine group formation is preferably conducted at a temperature of from about 75° C. to about 85° C., and at a pressure of 1 atm. The reaction may, for example, be completed over the course of about 16 hours to about 24 hours, and is preferably conducted under an atmosphere of argon.

The molar ratio of the preferred reducing agent triphenylphosphine to the starting compound II is preferably about 1.1:1. Solvents are preferably employed which are selected from organic and inorganic solvents such as a mixture of benzene and water or, most preferably, a mixture of tetrahydrofuran and water. Amounts of solvents are preferably those where the compound II starting material is from about 4 to about 6% by weight, based on the combined weight of solvent and compound II.

The method of converting a compound II to a compound III, and the compounds III, are novel.

Functionalization

Compounds of the formula III may be functionalized to yield compounds of the formula IV where $R^1$ and/or $R^2$ is other than hydrogen. The following exemplify methods which may be employed.

Sulfonamide, Sulfamide or Sulfinamide Formation

To prepare a compound IV where $R^1$ or $R^2$, together with the nitrogen atom to which it is bonded, forms a sulfonamide group

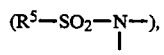
$(R^5-SO_2-N-)$, a sulfamide group

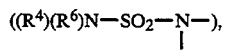
$((R^4)(R^6)N-SO_2-N-)$, or a sulfinamide group

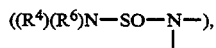
$((R^4)(R^6)N-SO-N-)$, the compound III may be contacted with a sulfonyl or sulfinyl halide of the formula:

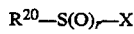
$R^{20}-S(O)_r-X$ where
   $R^{20}$ is $R^5$ and r is 2, or $R^{20}$ is $(R^4)(R^6)N-$ and r is 1 or 2, where $R^4$, $R^5$ and $R^6$ are as defined above; and
   X is halo, especially chloro;
preferably in the presence of a tertiary amine such as triethylamine, dimethylaminopyridine, or diisopropyl-(ethyl)amine.

The above reaction is preferably conducted at a temperature of from about 0° C. to about 25° C., and at a pressure of 1 atm. The reaction may, for example, be completed over the course of about 30 minutes to about 18 hours, and is preferably conducted under an atmosphere of argon.

Molar ratios of the compound $R^{20}-S(O)_r-X$ to the starting compound III are preferably from about 1.1:1 to about 1.2:1. Molar ratios of tertiary amine to the starting compound III are preferably from about 1.3:1 to about 1.5:1.

Solvents are preferably employed which are selected from organic solvents such as dichloromethane. Amounts of solvents are preferably those where the compound III starting material is from about 5 to about 10% by weight, based on the combined weight of solvent and compound III.

The above method of converting a compound III to a compound IV, and the compounds IV, are novel.

Amide, Urea or Urethane Formation

To prepare a compound IV where $R^1$ or $R^2$, together with the nitrogen atom to which it is bonded, forms an amide group, a urea group $((R^4)(R^6)N-C(O)-N-)$ or urethane group $((R^5)O-C(O)-N-)$, the compound III may be contacted with an acid, acid chloride or anhydride having the following formulae:

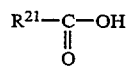
$R^{21}-C-OH$
     $\|$
     $O$

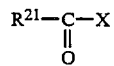
$R^{21}-C-X$
     $\|$
     $O$ or

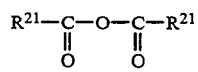
$R^{21}-C-O-C-R^{21}$
     $\|$       $\|$
     $O$       $O$ where
   $R^{21}$, together with the carbonyl group to which it is bonded, forms an acyl group, or where $R^{21}$ is $(R^4)(R^6)N-$ or $R^5O-$ where $R^4$, $R^5$ and $R^6$ are as defined above; and
   X is halo, especially chloro, preferably in the presence of a tertiary amine such as diisopropylethylamine or pyridine and/or condensing agents such as 1-hydroxybenzotriazole hydrate (HOBT) and 1-(3-di-methylaminopropyl)-3-ethylcarbodiimide hydrochloride.

The above reaction is preferably conducted at a temperature of about 24° C. and at a pressure of about 1 atm. The reaction may, for example, be completed over the course of about 1 hour and is preferably conducted under an atmosphere of argon.

Molar ratios of the compounds, $R^{21}-C(O)-OH$, $R^{21}-C(O)-X$, or $R^{21}-C(O)-O-C(O)-R^{21}$ to the starting compound III are preferably from about 1.5:1 to about 1.1:1.

Solvents are preferably employed which are selected from inorganic or organic solvents such as water, pyridine, dimethylformamide, tetrahydrofuran, dichloromethane, or mixtures thereof. Amounts of solvents are preferably those where the compound III starting material is from about 20 to about 5% by weight, based on the combined weight of solvent and compound III.

Another method for obtaining a urea group having the formula

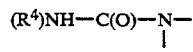
$(R^4)NH-C(O)-N-$ (formed by $R^1$ or $R^2$, together with the nitrogen atom to which it is bonded) is that where compound III is contacted with an isocyanate having the formula:

$R^4-N=C=O$ where $R^4$ is as defined above. This reaction is preferably conducted at a temperature of from about −5° C. to about 25° C., and at a pressure of about 1 atm. The reaction may, for example, be completed over the course of about 30 mins. to about 1 hour, and is preferably conducted under an atmosphere of argon.

Molar ratios of isocyanate to the starting compound III are preferably from about 1.5:1 to about 1.1:1. Solvents are preferably employed which are selected from organic solvents such as dichloromethane. Amounts of solvents are preferably those where the compound III starting material is from about 20 to about 5% by weight based on the combined weight of solvent and compound III.

Another method for the preparation of a compound IV where $R^1$ or $R^2$, together with the nitrogen atom to which it is bonded, forms an amide group is that comprising the step of contacting a compound III with an optionally substituted lactone. This reaction proceeds as follows:

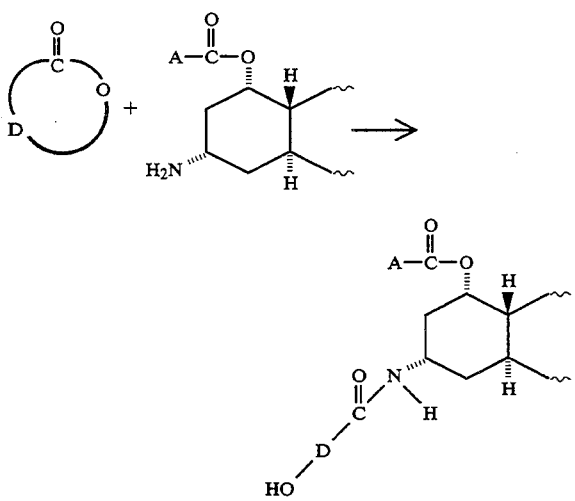

where D is selected so that the moiety HO—D—C(O)— is one of the groups recited for $R^1$ or $R^2$ above. An exemplary such lactone is that having the structure:

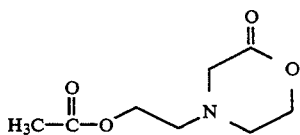

which, upon contact with the amino group of a compound III provides an $R^1$ or $R^2$ group of the formula:

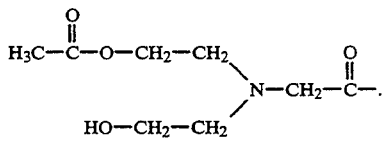

This reaction is preferably conducted at a temperature of from about 80° C. to about 90° C., and at a pressure of about 1 atm. The reaction may, for example, be completed over the course of about 24 hours and is preferably conducted under an atmosphere of argon.

Molar ratios of lactone to the compound III are preferably about 1.5:1. Solvents are preferably employed which are selected from organic solvents such as benzene or toluene. Amounts of solvents are preferably those where the starting material is from about 20 to about 5% by weight, based on the combined weight of solvent and starting material.

The above method of converting a compound III to a compound IV, and the compounds IV, are novel.

Alkyl-, Aryl-, Alkenyl-, Alkynyl-, Carbocyclo- or Heterocyclo-substituted Amine Formation To prepare a compound IV where $R^1$ or $R^2$, together with the nitrogen atom to which it is bonded, forms an alkyl-, aryl-, alkenyl-, alkynyl-, carbocyclo- or heterocyclo-substituted amine group, the compound III may be contacted with a compound having the formula:

$$R^{22}—X$$

where
$R^{22}$ is an alkyl, aryl, alkenyl, alkynyl, carbocyclo, or heterocyclo group; and X is halo, especially chloro or iodo, preferably in the presence of a tertiary amine such as diisopropylethylamine.

The above reaction is preferably conducted at a temperature of from about 23° C. to about 25° C., and at a pressure of about 1 atm. The reaction may, for example, be completed over the course of about 5–6 days, and is preferably conducted under an atmosphere of argon.

Molar ratios of the compound $R^{22}$—X to the starting compound III are preferably from about 20:1 to about 30:1.

Solvents are preferably employed which are selected from organic or inorganic solvents such as dimethylformamide. Amounts of solvents are preferably those where the compound III starting material is from about 8 to about 12% by weight, based on the combined weight of solvent and compound III.

Alternatively, and preferably, reductive amination is employed to obtain the above-described substituted-amine compounds of formula IV. Specifically, a compound III is contacted with an aldehyde or ketone having the formula:

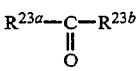

where $R^{23a}$ and $R^{23b}$ are independently selected from hydrogen, alkyl, alkenyl, alkynyl, aryl, carbocyclo or heterocyclo, in the presence of hydrogen gas and a hydrogenation catalyst such as $Pd(OH)_2$ supported on carbon or 10% Pd on carbon.

The above reaction, yielding a group $R^1$ and/or $R^2$ which, together with the nitrogen atom to which it is bonded, forms the substituted amine group

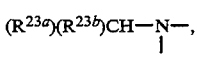

is preferably conducted at a temperature of from about 20° C. to about 25° C., and at a hydrogen pressure of about 1 atm. The reaction may, for example, be completed over the course of about 4 hours to about 18 hours.

Molar ratios of the aldehyde or ketone to the starting compound III are preferably from about 20:1 to about 25:1. Molar ratios of the hydrogenation catalyst to the starting compound III are preferably from about 0.1:1 to about 0.2:1.

Solvents are preferably employed which are selected from inorganic or organic solvents such as water and methanol. Amounts of solvents are preferably those where the compound III starting material is from about 4 to about 6% by weight, based on the combined weight of solvent and compound III.

The above methods for converting a compound III to a compound IV, and the compounds IV, are novel.

Guanidine Formation

To prepare a compound IV where $R^1$ or $R^2$, together with the nitrogen atom to which it is bonded, forms a guanidine

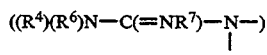

group, the compound III may be treated with a guanidinyl group forming agent under conditions for guanidine group formation, such as those described in Rasmussen et al., Synthesis, 460 (1988); Kim et al., Tetrahedron Lett., 29, 3183 (1988); and Atwal et al., Tetrahedron Lett., 30, 7313 (1989), incorporated herein by reference. In particular, a guanidine group may be formed by reacting an acylated thiourea (e.g.

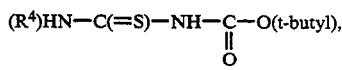

which may be formed by reacting an amine $R^4$—$NH_2$ with benzoyl isothiocyanate in chloroform to furnish a benzoyl thiourea, which in turn may be benzoyl deacylated (e.g. $K_2CO_3$, $CH_3OH$, $H_2O$), followed by reacylation ((t-butoxycarbonyl)$_2$O, NaH,THF)) with the hydrochloride of compound III in the presence of, for example, 1-(3-dimethylaminopropyl)-3-ethylcarbodiimide hydrochloride (e.g. dimethylformamide, triethylamine, room temperature). The acyl group may be removed with acid (e.g. HCl or trimethylsilyltrifluoromethanesulfonate). Alternatively, a diacylated thiourea (e.g., (t-butyl)O—C(O)—NH—C(=S)—NH—C(O)—O—(t-butyl), e.g., prepared by contact with (t-butoxycarbonyl)$_2$O, NaH, THF) may be reacted with a compound III to give a diacylated guanidine which may be treated with acid (e.g. $CF_3CO_2H$, $CH_2Cl_2$) to yield a guanidine group. See Poss et al., Abstract ORGN 424, 203rd Meeting of the American Chemical Society (April 1992), also incorporated herein by reference.

Conversion of a compound III to a guanidinyl group containing compound IV, and the compounds IV, are novel.

Fluoramine Formation

To prepare a compound IV where $R^1$ or $R^2$ is fluoro, the compound III may be fluorinated under conditions such as those described by Sharts, J. Org. Chem., 33(3), 1008–1011 (1968); Grakauskas et al., J. Org. Chem., 34 (10), 2840–2845 (1969); Wiesboeck et al., Tetrahedron, 26, 837–840 (1970); and Grakauskas et al., J. Org. Chem., 35 (5), 1545–1549 (1970), incorporated herein by reference.

The above conversion of a compound III to a fluoroamine compound IV, and the compounds IV, are novel.

Conversion of Functional Groups

Compounds of the formula IV, prepared by functionalizing the amino group of compounds of the formula III may, where desired, be further modified to form other compounds of the formula IV.

Exemplary of such further modification is oxidation of thio-containing $R^1$ or $R^2$ groups to sulfonyl-containing $R^1$ or $R^2$ groups. For example, as discussed above, compounds of the formula III may be functionalized to yield compounds of the formula IV where $R^1$ or $R^2$ is acyl by contact with an acyl chloride. Such acyl chlorides include alkylthioalkylcarbonyl chlorides, e.g. methyl thioacetyl chloride. The $R^1$ or $R^2$ alkylthioalkylcarbonyl group formed may be converted to an alkylsulfonylalkylcarbonyl group by treatment with an oxidizing agent such as m-chloroperoxybenzoic acid, or $H_2O_2$ or buffered oxone ($2KHSO_5.KHSO_4.K_2SO_4$).

The above oxidation reaction is preferably conducted at a temperature of from about 0° C. to about room temperature, and at a pressure of about 1 atm. The reaction may, for example, be completed over the course of about 30 mins. and is preferably conducted under an atmosphere of air.

Molar ratios of oxidizing agent to the thio-containing compound IV are preferably from about 2.2:1 to about 2.0:1. Solvents are preferably employed which are selected from organic solvents such as dichloromethane. Amounts of solvents are preferably those where the thio-containing compound IV is from about 20 to about 5% by weight, based on the combined weight of solvent and compound IV.

An additional exemplary further modification of a functional group is that of converting an amide group formed by an $R^1$ or $R^2$ group, together with the nitrogen atom to which it is bonded, to yield a thioamide group containing the moiety

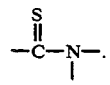

This modification may be accomplished by contacting the amide compound IV with any agent capable of converted a carbonyl group (—C(=O)—) to a thionyl group (—C(=S)—). Exemplary such agents are Lawesson's reagent or phosphorus pentasulfide.

The above reaction may, for example, be conducted at a temperature of from about 0° C. to about 25° C., and at a pressure of about 1 atm. The reaction may, for example, be conducted over the course of about 1 hour, and is preferably conducted under an atmosphere of argon.

Molar ratios of thionyl group-forming agent to amide starting compound are preferably from about 1:1 to about 1:2. Solvents are preferably employed which are selected from organic solvents such as toluene. Amounts of solvents are preferably those where the amide starting material is from about 3 to about 6% by weight, based on the combined weight of solvent and amide starting material.

Another exemplary further modification of a functional group is that of converting an amide group or thioamide group formed by an $R^1$ or $R^2$ group, together with the nitrogen atom to which it is bonded, to yield a substituted amine group as follows:

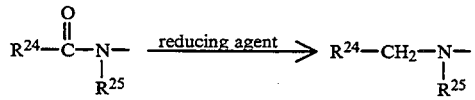

or

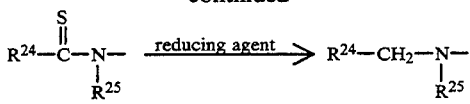

where $R^{24}$ and $R^{25}$ are independently selected from hydrogen, alkyl, aryl, alkenyl, alkynyl, carbocyclo or heterocyclo groups. Any compound capable of effecting the aforementioned reductions may be employed as the reducing agent. Exemplary such agents are a combination of $NaBH_4$ and $NiCl_2.6H_2O$.

The above reduction is preferably conducted at a temperature of from about $-20°$ C. to about $0°$ C., and at a pressure of about 1 atm. The reaction may, for example, be completed over the course of about 0.5 hour to about 1 hour, and is preferably conducted under an atmosphere of argon.

Molar ratios of reducing agent to the amide or thioamide compound IV are preferably from about 3:1 to about 6:1. Solvents are preferably employed which are selected from organic solvents such as a methanol/tetrahydrofuran mixture. Amounts of solvents are preferably those where the compound IV amide or thioamide is from about 3 to about 4% by weight, based on the combined weight of solvent and compound IV.

The above further modifications to the compounds of formula IV, and the compounds produced, are novel.

Compounds where $R^1 + R^2$ together form a Heterocyclo Group

Compounds IV wherein $R^1$ and $R^2$ together with the nitrogen atom to which they are bonded form the moiety:

where W is a grouping of atoms completing a heterocyclo group, and where "heterocyclo" is as defined above, may be prepared by contacting a compound III with a compound of the formula:

where W is as defined above and X is halo, especially bromo, preferably in the presence of a tertiary amine such as diisopropyl(ethyl)amine. An exemplary compound X—W—X is 1,4-dibromobutane (forming, in the resulting compound IV, a pyrrolidine group). This reaction is preferably conducted at a temperature of about 25° C. and at a pressure of about 1 atm. The reaction may, for example, be completed over the course of about 3 days, and is preferably conducted under an atmosphere of argon, Molar ratios of the compound X—W—X to the starting compound III are preferably about 1.5:1. Solvents are preferably employed which are selected from organic solvents such as dichloromethane. Amounts of solvents are preferably those where the compound III starting material is about 0.02% by weight based on the combined weight of solvent and compound III.

Functionalization of Compounds IV having one of $R^1$ or $R^2$=H

A further novel method, and novel compounds, provided by the present invention is that where a compound IV having one group $R^1$ or $R^2$ which has been functionalized, and the other which is hydrogen, is modified so as to functionalize the group $R^1$ or $R^2$ which is hydrogen by any suitable method for functionalization exemplified by those described above.

Deprotection

Compounds of the formulae III or IV are deprotected to obtain compounds of the formula I. Any suitable method for removing the protecting group "$Pro^1$" to yield a free hydroxyl group may be employed.

Where, for example, $Pro^1$ is benzyloxymethyl, the compounds of formulae III or IV may be hydrogenated by treatment with hydrogen gas and a hydrogenation catalyst such as $Pd(OH)_2$ on a carbon support (e.g. 20% palladium hydroxide on carbon) alone or with a catalytic carboxylic acid such as acetic acid or trifluoroacetic acid or mineral acid such as HCl. The reaction is preferably conducted at a temperature of from about 20° C. to about 25° C., and at a pressure of about 1 atm. The reaction may, for example, be completed over the course of about 30 mins. to about 18 hours.

The molar ratio of hydrogenation catalyst to the formula III or IV compound is preferably about 0.1:1.

Solvents are preferably employed which are selected from organic solvents such as ethyl acetate or tetrahydrofuran. Amounts of solvents are preferably those where the compound III or IV starting material is from about 3 to about 8% by weight, based on the combined weight of solvent and formula III or IV compound.

Deprotection of compounds III or IV to yield compounds of the formula I where Z is a lactone moiety is novel.

Lactone Ring Opening

Compounds of the formula I where Z is a lactone moiety may optionally be converted to compounds having as the group Z:

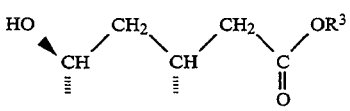

where $R^3$ is as defined above by any suitable means for opening the lactone ring, such as hydrolysis. Hydrolysis is preferably conducted by employing a base such as an alkali metal hydroxide, particularly lithium hydroxide (e.g. 1N LiOH).

The hydrolysis reaction is preferably conducted at a temperature of from about 0° C. to about 25° C., and at a pressure of about 1 atm. The reaction may, for example, be completed over the course of about 15 mins. to about 4 hours, and is preferably conducted under an atmosphere of argon.

Molar ratios of base to lactone starting compound are preferably from about 1:1 to about 2:1.

Solvents are preferably employed which are selected from organic or inorganic solvents such as water, a mixture of acetonitrile and water, tetrahydrofuran and water, dioxane and water, or dioxane/acetonitrile/water. Amounts of solvents are preferably those where the lactone starting material is from about 3 to about 11% by weight, based on the combined weight of solvent and lactone starting material.

Preparation of a compound of the formula I as described above is novel.

Quaternary Ammonium Salt Formation

Quaternary ammonium salts may preferably be prepared by contacting a compound of the formula I (or intermediates in the preparation thereof) with a compound of the formula $R^{16}$—Y where $R^{16}$ is as defined above and Y forms a pharmaceutically acceptable counterion such as halo.

The counterion Y of the quaternay ammonium salt so formed may be exchanged. For example, when Y is halo such as iodo, contact with a hydroxide ion donor exemplified by an alkali metal hydroxide such as LiOH will provide a salt with a hydroxyl, rather than halo, counterion.

N-oxide Formation

N-oxide formation is preferably achieved by contacting a compound I, or intermediate formed in the preparation thereof, with an oxidizing agent such as m-chloroperoxybenzoic acid or peracetic acid. The reaction is preferably conducted at a temperature of from about 0° C. to about 10° C., and at a pressure of about 1 atm. The reaction may, for example, be completed over the course of about 1 hour to about 4 hours, and is preferably conducted under an atmosphere of argon.

Molar ratios of oxidizing agent to the compound to be oxidized are preferably from about 1.5:1 to about 2.0:1. Solvents are preferably employed which are selected from inorganic or organic solvents such as tetrahydrofuran or acetic acid. Amounts of solvents are preferably those where the starting material is from about 5 to about 8% by weight, based on the combined weight of solvent and starting material.

The instant invention further provides novel intermediates and methods of preparation which are described in the above Reaction Schemes. These novel intermediates include those compounds designated above as II, III and IV, including all stereoisomers, salts, N-oxides where appropriate, and solvates thereof. N-oxides and salts (and solvates by definition) thereof, where appropriate, may be employed in, or prepared by, the novel methods of preparation wherever compounds of the formulae II, III and IV are employed or prepared.

Preferred Utility

The compounds of the invention are inhibitors of 3-hydroxy-3-methylglutaryl coenzyme A (HMG-CoA) reductase and thus are useful in inhibiting cholesterol biosynthesis.

The instant invention also provides pharmaceutical compositions comprising at least one of the inventive compounds in association with a pharmaceutically acceptable vehicle or diluent. The pharmaceutical composition may be formulated by employing conventional solid or liquid vehicles or diluents, as well as pharmaceutical additives of a type appropriate to the mode of desired administration. The compounds may, for example, be administered by an oral route, such as in the form of tablets, capsules, granules or powders, or they may be administered by a parenteral route, such as in the form of injectable preparations.

A typical capsule for oral administration may contain active ingredient(s) (e.g. 25 mg), lactose (e.g. 75 mg) and magnesium stearate (e.g. 15 mg). The mixture is passed through a 60-mesh sieve and packed into a No. 1 gelatin capsule.

A typical injectable preparation may be produced by aseptically placing 25 mg of a water-soluble salt of sterile active ingredient(s) into a vial, aseptically freeze-drying and sealing. For use, the contents of the vial may be mixed with 2 ml of physiological saline to produce an injectable preparation.

Such dosage forms preferably contain from about 1 to 2000 mg of active compound per dosage. The dose to be administered depends on the unitary dose, the symptoms, and the age and the body weight of the patient, and may be determined by the skilled artisan. Exemplary pharmaceutical compositions of the instant invention are hypocholesterolemic, hypolipoproteinaemic, antiatherosclerotic and/or hypolipidemic compositions comprising an amount of the inventive compound effective therefor.

The inventive compounds may be administered in a similar manner as known compounds suggested for use in inhibiting cholesterol biosynthesis, such as lovastatin, particularly to subjects which are mammalian species such as humans, dogs, cats and the like. A dose for adults is preferably between 20 and 2,000 mg per day, which may be administered in a single dose or in the form of individual divided doses from 1-4 times per day.

The compounds of the present invention may also be employed in combination with antihyperlipoproteinemic agents, such as probucol, and/or with one or more serum cholesterol lowering agents such as gemfibrozil, bile acid sequestrants such as cholestyramine, colestipol, DEAE-Sephadex ® as well as clofibrate, nicotinic acid and its derivatives, neomycin, p-aminosalicyclic acid, lovastatin, pravastatin, visinolin (velostatin, symvastatin or sinvinolin) and the like, and/or one or more squalene synthetase inhibitors. The above compounds to be employed in combination with the HMG-CoA reductase inhibitor of the invention will be used, for example, in amounts as indicated in the Physicians' Desk Reference (PDR).

The instant invention also provides methods for the treatment or prevention of hypercholesterolemia, atherosclerosis, hyperlipoproteinaemia, and/or hyperlipidemia (e.g. nephrotic hyperlipidemia) comprising the step of administering to a subject in need thereof an inventive compound in an amount effective therefor. The inventive compounds may be used to lower serum triglycerides, or to raise the plasma ratio of high density lipoprotein (HDL) cholesterol to low density lipoprotein (LDL) cholesterol. As HMG-CoA reductase inhibitors, the compounds of the invention may also be useful in inhibiting the formation of gallstones and as anti-cancer agents by preventing, or by reducing or maintaining the size of tumors.

The compounds of this invention may, further, be employed as antifungal agents, useful in controlling the growth of, including elimination of, one or more strains of fungi. For example, they may be used to control strains of Penicillium sp., *Aspergillus niger*, Cladosporium sp., *Cochliobolus miyabeorus* and *Helminthosporium cynodnotis*. For these utilities, the inventive compounds may, for example, be admixed with suitable formulating agents, powders, emulsifying agents or solvents (such as aqueous ethanol) and sprayed or dusted on plants to be protected.

The following Examples represent preferred embodiments of the present invention, and are not intended to limit the scope or spirit of the instant claims. The following abbreviations are employed in the Examples:

Abbreviations

BOM=(phenylmethoxy)methyl (i.e.(benzyloxy)methyl)
DMF=dimethylformamide
$PPh_3$=triphenylphosphine RT=room temperature
AcOH=acetic acid
EtOAc=ethyl acetate
sat'd=saturated
MeOH=methanol
EtOH=ethanol
TLC=thin layer chromatography
Hunigs base=diisopropylethylamine
THF=tetrahydrofuran
Me=methyl
Ph=phenyl
PMA=phosphomolybdic acid Lawesson's reagent=[2,4-bis(4-methoxyphenyl)-1,3-dithia-2,4-diphosphetane-2,4-disulfide], having the structure:

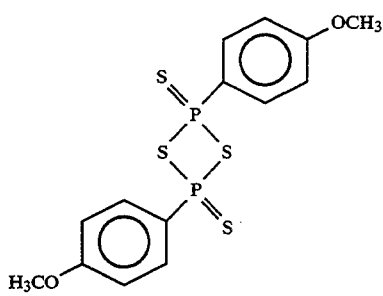

HOBT—1-hydroxybenzotriazole hydrate
EDC=1-(3-dimethylaminopropyl)-3-ethylcarbodiimide hydrochloride

EXAMPLE 1

Preparation of
[1S-[1α,3α,4aα,7β,8β-(2S*,4S*),8aβ]]-2,2-Dimethylbutanoic acid, 3-[(methylsulfonyl)amino]decahydro-7-methyl-8-[2-(tetrahydro-4-hydroxy-6-oxo-2H-pyran-2-yl)ethyl[-1-naphthalenyl ester (a) [1S-[1α,3α,4aα,7β,8β(2S*,4S*),8aβ[[-2,2-Dimethylbutanoic acid, 3-azidodecahydro-7-methyl-8-[2-(tetrahydro-4-[(phenylmethoxy)methoxy]-6-oxo-2H-pyran-2-yl]ethyl]-1-naphthalenyl ester

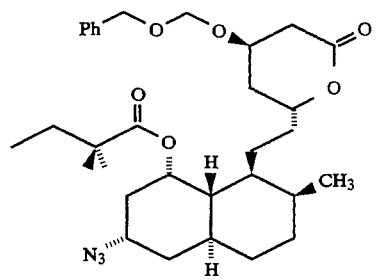

The starting alcohol [1S-[1α,3β,4aα,7β,8β-(2S*,4S*),8aβ]]-2,2-dimethylbutanoic acid, 3-hydroxydecahydro-7-methyl-8-[2-(tetrahydro-4-[(phenylmethoxy)methoxy]-6-oxo-2H-pyran-2-yl]ethyl]-1-naphthalenyl ester:

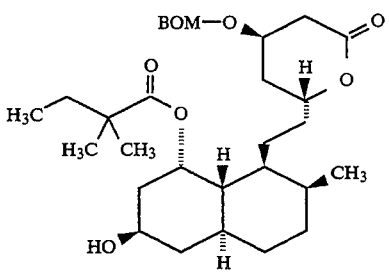

employed following, was obtained by the procedures set forth in European Patent Publication No. 0,465,265, incorporated herein by reference.

Azide formation was conducted by the following methods (i), (ii) and (iii), the latter being preferred:

(i) A solution of the above alcohol (1.00 g, 1.84 mmol), tetramethyl guanidium azide dried under high vacuum for 12 hours (2.90 g, 18.36 mmol), and $CBr_4$ (1.83 g, 5.51 mmol) in DMF (10 ml) was cooled, under argon, in an ice/water bath and treated with $PPh_3$ (1.20 g, 4.60 mmol) in one portion, and stirred at room temperature for 36 hours. The resulting reaction mixture was worked up as described below to obtain the title compound ($C_{32}H_{47}N_3O_6$, 553 mgs, 53% theory, $(M+H)^+=570$, as a clear colorless oil).

(ii) A solution of the above alcohol (1.00 g, 1.84 mmol), $LiN_3$ (540 mgs, 11.02 mmol) and $CBr_4$ (1.83 g, 5.51 mmol) in DMF (16 ml) under argon, was cooled in an ice/water bath and treated with $PPh_3$ (1.20 g, 4.60 mmol) in one portion. The reaction effervesced mildly, the cooling bath was removed almost immediately giving a golden/cloudy (undissolved $PPh_3$) suspension; after stirring at RT for $\leq 5$ minutes the reaction mixture became a clear golden solution which appeared to be effervescing very slowly. The mixture was stirred at RT for 36 hours. The resulting reaction mixture (clear light orange color) was worked up as described below to obtain the title compound ($C_{32}H_{47}N_3O_6$, 541 mgs, 52% theory, clear pale yellow oil) and dehydrated products (not collected).

(iii) A solution of the above alcohol (1.24 g, 2.28 mmol) and $LiN_3$ (806 mgs, 6.83 mmol) in DMF (18.5 ml) was treated with $BrCCl_3$ (673 μl, 6.83 mmol) and placed in a 10° C. water bath. The solution was treated with $PPh_3$ (1.49 g, 5.70 mmol), stirred at about 10° C. for 5 mins., allowed to warm to room temperature and stirred for 24 hours. The resulting reaction mixture was worked up as described below to afford the title compound ($C_{32}H_{47}N_3O_6$, 832 mgs, 64% theory) as a clear pale yellow oil.

Work-up procedure for (i), (ii) and (iii):

In each case, the reaction mixture was partitioned between EtOAc (150 ml)/$H_2O$ (50 ml) and shaken well. The aqueous layer was separated and extracted with EtOAc (3×40 ml). The combined organic layers were washed with 5% $Na_2S_2O_3$ (30 ml), brine (50 ml), dried ($MgSO_4$) and the solvent removed by evaporation to give an oil which was purified by column chromatography on silica gel using 20% EtOAc/80% hexane as the mobile phase.

(b) [1S-[1α,3α,4aα,7β,8β(2S*,4S*),8aβ]]-2,2-Dimethylbutanoic acid, 3-aminodecahydro-7-methyl-8-

[2-[tetrahydro-4-[(phenylmethoxy)methoxy]-6-oxo-2H-pyran-2-yl]ethyl]-1-naphthalenyl ester

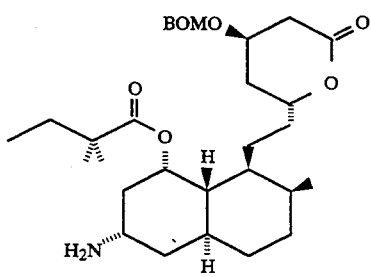

A solution of the azide title product of step (a) above (493 mgs, 0.865 mmol) and triphenylphosphine (227 mgs, 0.865 mmol) in THF (10 ml)/H$_2$O (1 ml) was heated at 80° C. (oil bath temp.) for 24 hours. The solvent was removed by evaporation and the residue purified by column chromatography on silica gel using 1) EtOAc (to remove impurities such as Ph$_3$P=O) and 2) 35% isopropyl alcohol/65% EtOAc yielding the amine title product as a clear, pale yellow oil (C$_{32}$H$_{49}$NO$_6$, 365 mgs, 78% theory, (M+H)$^+$=544).

(c) [1S-[1α,3β,4aα,7β,8β(2S*,4S*),8aβ]]-2,2-Dimethylbutanoic acid, 3-[(methylsulfonyl)amino]-decahydro-7-methyl-8-[2 -[tetrahydro-4-[(phenylmethoxy) methoxy]-6-oxo-2H-pyran-2-yl]ethyl]-1-naphthalenyl ester

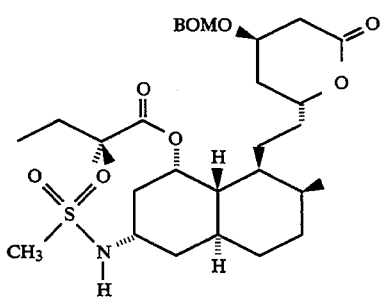

A solution of the amine title product of step (b) above (162 mgs, 0.298 mmol) in CH$_2$Cl$_2$ (5 ml) was treated with diisopropylethylamine (62 μl, 0.358 mmol) followed by CH$_3$SO$_2$Cl (24 μl 0.313 mmol) and stirred at RT for 1 hour. The solvent was removed by evaporation to give an oil which was purified by column chromatography on silica gel using 50% EtOAc/50% hexane as the mobile phase yielding a clear, colorless oil (white foam) containing the title product (C$_{33}$H$_{51}$NO$_8$S, 140 mgs, 76% theory).

(d) [1S-[1α,3α,4aα,7β,8β(2S*,4S*),8aβ]]-2,2-Dimethylbutanoic acid, 3-[(methylsulfonyl)amino]-decahydro-7-methyl-8-[2-(tetrahydro-4-hydroxy-6-oxo-2H-pyran-2-yl)ethyl]-1-napthalenyl ester

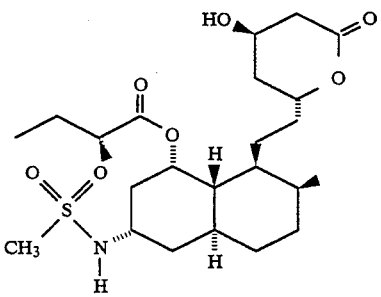

A solution of the sulfonamide title product of step (c) above (140 mg, 0.225 mmol) in EtOAc was treated with a catalytic amount of 20% Pd(OH)$_2$/C (10 mgs) and a drop of AcOH. The solution was degassed with argon. H$_2$ gas was bubbled through the solution via an Orsat gas balloon with stirring. The reaction was complete by 45 minutes. The solution was filtered through a short pad of Celite. The solution was treated with (sat'd.) NaHCO$_3$. The organic fraction was washed with brine and dried (MgSO4). This was combined with another batch of the title product alcohol previously prepared (~35 mg, ~0.07 mmol), the solvent removed by evaporation and the residue purified by column chromatography on SiO$_2$ using EtOAc as the mobile phase to yield a white foam of the title product (C$_{25}$H$_{43}$O$_7$NS, 121 mg, 0.24 mmol, 81% theory).

EXAMPLE 2

Preparation of
[1S-[1α(βS*,δS*),2α,4aβ,6β,8β,8aα]]-8-(2,2-Dimethyl-1-oxobutoxy)decahydro-β,δ-dihydroxy-2-methyl-6-[(methylsulfonyl)amino]-1-naphthaleneheptanoic acid, monolithium salt

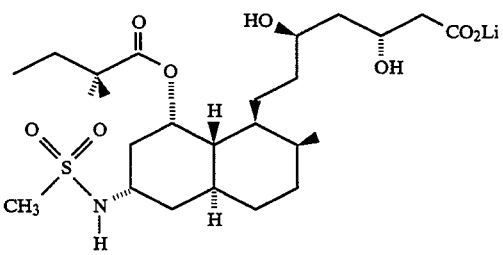

A solution of the lactone title product of step (d) of Example 1 above (108 mg, 0.215 mmol) was treated with 2 eq. 1N LiOH (0.431 mmol, 431 μl) in 3:1 CH$_3$CN/H$_2$O (5 ml). The solution was stirred. The solvent was removed by evaporation. The residue was purified by column chromatography on CHP-20P gel using 1) H$_2$O; 2) 30% CH$_3$CN/H$_2$O. The liquid was concentrated by evaporation, and the material then frozen and lyophilized to give an electrostatic white foam of the title product (C$_{25}$H$_{44}$O$_8$NSLi, 98 mg, 0.186 mmol, 87% theory, [α]$_D^\circ$=+59.1° (c=0.44, MeOH), TLC: R$_f$=0.4 in 80:10:10 (CH$_2$Cl$_2$: AcOH:MeOH)-developed using a 10% solution of phosphomolybdic acid in ethanol). Elemental Analysis (%) for C$_{25}$H$_{44}$O$_8$NSLi.1.00 H$_2$O

|   | Calc. | Found |
| --- | --- | --- |
| C | 55.24 | 55.02 |

|   | Calc. | Found |
|---|---|---|
| H | 8.53 | 8.51 |
| N | 2.58 | 2.95 |
| S | 5.90 | 6.01 |

EXAMPLE 3

Preparation of
[1S-[1α,3α,4aα,7β,8β(2S*,4S*),-8aβ]]-2,2-Dimethylbutanoic acid,
3-[[(methylsulfonyl)acetyl]amino]decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-[[(methylthio)acetyl]amino]decahydro-7-methyl-8-[2-[tetrahydro-4-[(phenylmethoxy)methoxy]-6-oxo-2H-pyran-2-yl]ethyl]-1-napthalenyl ester

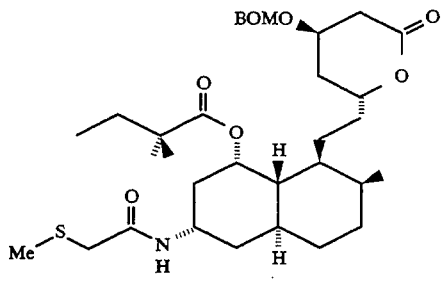

A solution of the BOM-amine title product of step (b) of Example 1 above (324 mg, 0.60 mmol) in $CH_2Cl_2$ was treated with 3 eq. diisopropylethylamine (1.8 mmol, 156 μl) followed by (methylthio)acetyl chloride (0.6 mmol) and the solution was stirred for ½ hour. The solution was diluted with EtOAc and washed with 5% $KHSO_4$ followed by sat'd $NaHCO_3$ followed by brine. The organic fraction was dried over $MgSO_4$, filtered and solvent removed by evaporation. The residue was purified on $SiO_2$ using 50% hexane/50% EtOAc, yielding the title product as a colorless oil ($C_{35}H_{53}NO_7S$, 305 mg, 0.48 mmol, 80% theory).

(b) [1S-[1α,3α,4aα,7β,8β(2S*,4S*),8aβ]]-2,2-Dimethylbutanoic acid, 3-[[(methylsulfonyl)acetyl]amino]decahydro-7-methyl-8-[2-[tetrahydro-4-](phenylmethoxy)methoxy]-6-oxo-2H-pyran-2-yl]ethyl]-1-napthalenyl ester

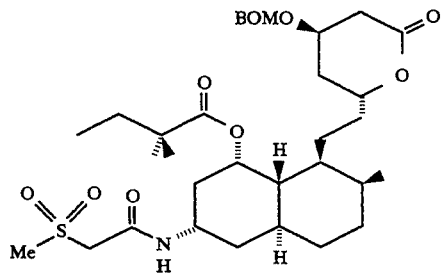

A solution of the amide title product of step (a) above (280 mg, 0.44 mmole) in $CH_2Cl_2$ was treated with 2.2 eq m-chloroperoxybenzoic acid (m-CPBA) (0.97 mmol calc. at 80%, 210 mg) and stirred for 2 hours. The solution was diluted with EtOAc and treated with $NaHSO_3$ (aq.) followed by $NaHCO_3$ (aq.) followed by brine. The solvent was removed by evaporation to yield the title product as a white foamy solid ($C_{35}H_{53}NO_9S$, 330 mg, 0.50 mmol).

(c) [1S-[1α,3α,4aα,7β,8β(2S*,4S*),8aβ]]-2,2-Dimethylbutanoic acid, 3-[((methylsulfonyl)acetyl)amino]decahydro-7-methyl-8-[2-(tetrahydro-4-hydroxy-6-oxo-2H-pyran-2-yl)ethyl]-1-napthalenyl ester

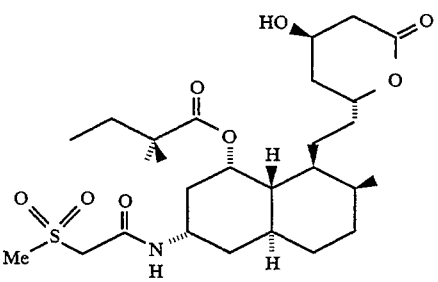

A solution of the sulfone prepared as the title product in step (b) above (330 mg, 0.50 mmol) was dissolved in EtOAc and treated with 1 ml acetic acid, followed by $Pd(OH)_2/C$. The solution was subjected to vigorously bubbled $H_2$. The solution was filtered through a short pad of Celite and the procedure was repeated. The solution was again filtered through Celite and diluted with EtOAc. The organic was washed with $NaHCO_3$ (aq. sat'd.) followed by brine. The solution was dried over $MgSO_4$, filtered and the solvent removed by evaporation. The residue was purified on $SiO_2$ using 70% EtOAc/30% hexane as the mobile phase yielding the title product as a white foamy solid ($C_{27}H_{45}NO_8S$, 160 mg, 60% theory).

EXAMPLE 4

Preparation of
[1S-[1α(βS*,S*),2α,4aβ,6β,8β,8aα]]-8-(2,2-Dimethyl-1-oxobutoxy)decahydro-β,δ-dihydroxy-2-methyl-6-[[(methylsulfonyl)acetyl]-amino]-1-naphthaleneheptanoic acid, monolithium salt

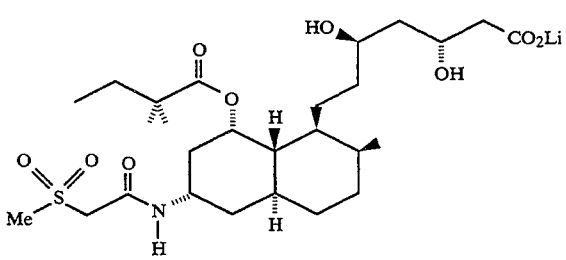

A solution of the amide-sulfone (160 mg, 0.29 mmol) prepared as the title product in Example 3 above in $CH_3CN$ (5 ml) was treated with 2 eq. 1N LiOH (0.58 mmol, 580 μl). The solution was stirred for 2 hours. The solvent was reduced by evaporation and the residue was purified on CHP-20P gel using 1) $H_2O$; 2) 20% acetonitrile/80% $H_2O$ as the mobile phase. The relevant fractions were combined, solvent was reduced by evaporation and the resulting solution filtered through a 3 μm filter and lyophilized overnight to yield a white lyophilate as the title product ($C_{27}H_{46}NO_9SLi$, 160 mg, 97% theory, $[α]_D^{20} = +36.6°$ (c=0.30, MeOH), TLC:

$R_f$=0.50 on $SiO_2$ using 8:1:1 ($CH_2Cl_2$:MeOH:AcOH): developed using a 10% solution of phosphomolybdic acid in ethanol).

Elemental Analysis (%) for $C_{27}H_{46}NO_9SLi \cdot 0.76\ H_2O$

|   | Calc. | Found |
|---|---|---|
| C | 55.79 | 55.96 |
| H | 8.24 | 8.35 |
| N | 2.41 | 2.24 |
| S | 5.52 | 5.32 |

EXAMPLE 5

Preparation of [1S-[1α,3α,4aα,7β,8β(2S*,4S*),8aβ]]-2,2-Dimethylbutanoic acid, 3-[(methoxyacetyl)amino]decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-[(methoxyacetyl)amino]-decahydro-7-methyl-8-[2-[tetrahydro-4-[(phenylmethoxy)methoxy]-6-oxo-2H-pyran-2-yl]ethyl]-1-napthalenyl ester

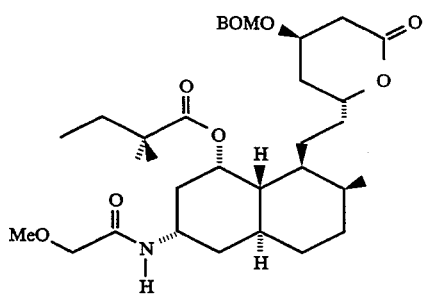

A solution of the BOM-amine prepared as the title product in step (b) of Example 1 above (232 mg, 0.43 mmol) in $CH_2Cl_2$ (10 ml) was treated with diisopropylethylamine (1.29 mmol, 225 μl) with stirring. The solution was placed under $N_2$ and treated with methoxyacetyl chloride (0.645 mmol, 70 mg, 60 μl) and stirred at RT for ½ hour. The solvent was removed by evaporation and the residue purified on $SiO_2$ using 65% EtOAc/35% hexane as the mobile phase yielding the title product as a colorless oil (135 mg, 0.219 mmol, 51% theory).

(b) [1S-[1α,3α,4aα,7β,8β(2S*,4S*),8aβ]]-2,2-Dimethylbutanoic acid, 3-[(methoxyacetyl)amino]-decahydro-7-methyl-8-[2-(tetrahydro-4-hydroxy-6-oxo-2H-pyran-2-yl)ethyl]-1-napthalenyl ester

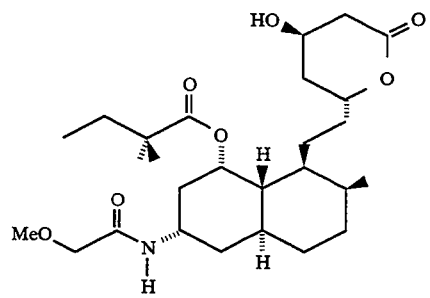

A solution of the amide prepared as the title product in step (a) above (135 mg, 0.219 mmol) was dissolved in EtOAc (10 ml), treated with AcOH (~½ ml) followed by $Pd(OH)_2$/C and bubbled through with $H_2$. The solution was filtered through a short pad of Celite, diluted with EtOAc and treated with $NaHCO_3$ (sat'd.) followed by brine. The organic fraction was dried over $MgSO_4$. Solvent was removed by evaporation. The residue was purified on $SiO_2$ using 70% EtOAc/30% hexane yielding the title product as a white solid ($C_{28}H_{47}NO_6$, 90 mg, 0.182 mmol, 83% theory).

EXAMPLE 6

Preparation of [1S-[1α(βS*,δS*), 2α,4aβ,6β,8β,8aα]]-8-(2,2-Dimethyl-1-oxobutoxy)-decahydro-β,δ-dihydroxy-6-[(methylacetyl)amino]-2-methyl-1-naphthaleneheptanoic acid, monolithium salt

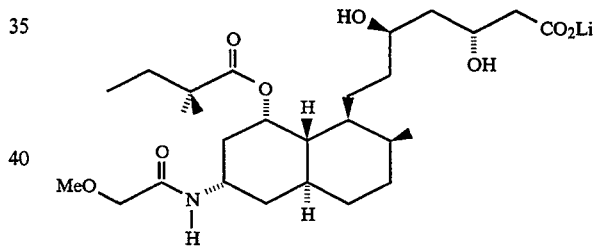

A solution of the amide title product prepared in Example 5 above (90 mg, 0.182 mmol) was dissolved in $CH_3CN/H_2O$ (~8:1) and treated with aqueous 1N LiOH (0.364 mmol, 364 μl). The solution was stirred for 2 hours. The solvent was removed by evaporation. The residue was purified on CHP-20P gel using 1) $H_2O$, 2) 20% $CH_3CN/H_2O$ as the mobile phase. The solvent was reduced to $H_2O$ and filtered through a 0.3 μm Whatman membrane filter. The solution was frozen and lyophilized overnight to yield the title product as a white lyophilate ($C_{27}H_{46}NO_8Li$, 55 mg, 0.106, 60% theory, $[α]_D° = +74.2$ (c=0.25, MeOH), TLC: $R_f$=0.70 on $SiO_2$ using 8:1:1 ($CH_2Cl_2$:MeOH:AcOH): developed using a 10% solution of phosphomolybdic acid in ethanol).

Elemental Analysis (%) for $C_{27}H_{46}NO_8Li \cdot 1.04\ H_2O$

|   | Calc. | Found |
|---|---|---|
| C | 59.34 | 59.46 |
| H | 9.21 | 8.90 |
| N | 2.66 | 2.54 |

EXAMPLE 7

Preparation of
[1S-[1α,3α,4aα,7β,8β(2S*,4S*),8aβ]]-2,2-Dimethylbutanoic acid,
3-(benzoylamino)decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-(benzoylamino)-decahydro-7-methyl-8-[2-[tetrahydro-4-[(phenylmethoxy)methoxy]-6-oxo-2H-pyran-2-yl]ethyl]-1-naphthalenyl ester

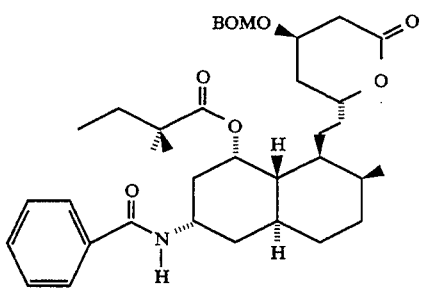

A solution of the BOM-amine prepared as in step (b) of Example 1 above (313 mg, 0.576 mmol) was dissolved in $CH_2Cl_2$ and treated with 3 eq. diisopropylethylamine (1.728 mmol, 301 μl), followed by argon. The solution was then treated with benzoyl chloride (1.5 eq., 0.864 mmol). The solution was stirred for 1 hour. The solution was diluted with EtOAc and treated with 5% $KHSO_4$. The organic fraction was washed with sat'd. aq. $NaHCO_3$, followed by brine. The organic fraction was dried over $MgSO_4$ and solvent was removed by evaporation to yield the crude title product ($C_{39}H_{53}NO_7$, >500 mg). The crude product was employed directly in the next step.

(b) [1S-[1α,3α,4aα,7β,8β(2S*,4S*),8aβ]]-2,2-Dimethylbutanoic acid, 3-(benzoylamino)decahydro-7-methyl-8-[2-(tetrahydro-4-hydroxy-6-oxo-2H-pyran-2-yl)ethyl]-1-naphthalenyl ester

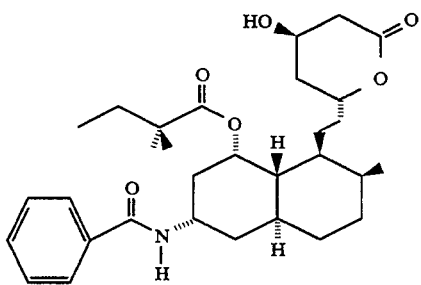

A solution of the BOM-benzamide obtained in step (a) above (>500 mg) in EtOAc was treated with ½ ml AcOH, followed by $Pd(OH)_2/C$ (20%). The solution was subjected to vigorous bubbling $H_2$. After completion, the solution was filtered through Celite and diluted with EtOAc. The EtOAc solution was then treated with (aq.) $NaHCO_3$ followed by brine. The organic fraction was washed over $MgSO_4$, filtered and solvent removed by evaporation. The residue was purified on $SiO_2$ using 55% EtOAc/45% hexane yielding a white solid as the title product ($C_{31}H_{45}NO_6$, 232 mg, 0.44 mmol, 76% theory (over the 2 steps).

EXAMPLE 8

Preparation of
[1S-[1α(βS*,δS*),2α,4aβ,6β,8β,8aα]]-6-(Benzoylamino)-8-(2,2-Dimethyl-1-oxobutoxy)decahydro-β,δ-dihydroxy-2-methyl-1-naphthalene heptanoic acid, monolithium salt

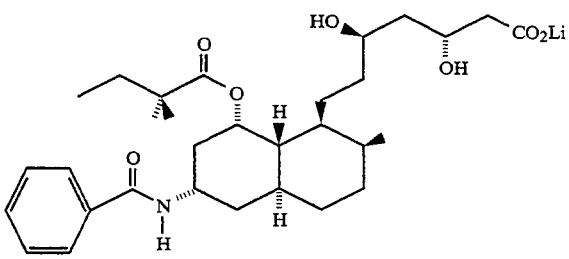

A solution of the amide (232 mg, 0.44 mmol) prepared in step (b) of Example 7 above in $CH_3CN/H_2O$ was treated with 2 eq. 1N LiOH (0.88 mmol, 888 μl) and the solution was stirred for 2 hours. The solvent was reduced by evaporation and the residue was purified on CHP-20P gel using 15% $CH_3CN/H_2O$ as the mobile phase. The solvent was reduced to $H_2O$ by evaporation. The solution was filtered through a 0.3 μm Whatman membrane filter. The solution was frozen and lyophilized overnight yielding the title product as a white lyophilate ($C_{31}H_{46}NO_7Li$, 150 mg, 62%, $[\alpha]_D^{20}$ = +104° (c=0.50, MeOH), TLC: $R_f$=0.50 on $SiO_2$ using 8:1:1 ($CH_2Cl_2$:MeOH:AcOH): developed using a 10% solution of phosphomolybdic acid in ethanol).

Elemental Analysis (%) for $C_{31}H_{46}NO_7Li \cdot 1.48 H_2O$

|   | Calc. | Found |
|---|---|---|
| C | 64.39 | 64.38 |
| H | 8.53 | 8.43 |
| N | 2.42 | 2.43 |

EXAMPLE 9

Preparation of
[1S-[1α,3α,4aα,7β,8β(2S*,4S*),8aβ]]-2,2-Dimethylbutanoic acid,
3-[(acetoxyacetyl)amino]decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-[(acetoxyacetyl)amino]-decahydro-7-methyl-8-[2-[tetrahydro-4-[(phenylmethoxy)methoxy]-6-oxo-2H-pyran-2-yl]-ethyl]-1-naphthalenyl ester

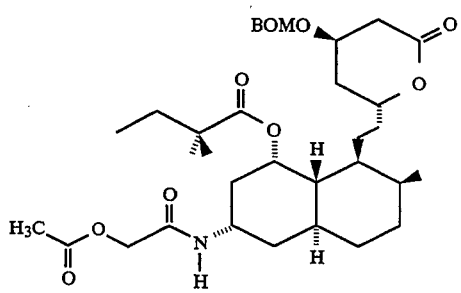

A solution of the amine title product prepared in step (b) of Example 1 above (320 mg, 0.589 mmol) in $CH_2Cl_2$ (10 ml) was treated with diisopropylethylamine (1.77 mmol, 308 μl) followed by treatment with acetoxyacetyl chloride (1.5 eq., 0.884 mmol, 120.62 mg, 94.5 μl). The solution was stirred for 1 hour, reduced in volume and partitioned between EtOAc and $H_2O$. The organic layer was washed with 5% $KHSO_4$, sat'd. $NaHCO_3$ and brine. The organic fraction was dried over $MgSO_4$ and solvent was removed by evaporation. The residue was purified on $SiO_2$ using 50% EtOAc/hexane as the mobile phase yielding the title product as a colorless oil (240 mg, % theory=69%).

(b) [1S-[1α,3α,4aα,7β,8β(2S*,4S*),8aβ]]-2,2-Dimethylbutanoic acid, 3-[(acetoxyacetyl)amino]-decahydro-7-methyl-8-[2-(tetrahydro-4-hydroxy-6-oxo-2H-pyran-2-yl)ethyl]-1-naphthalenyl ester

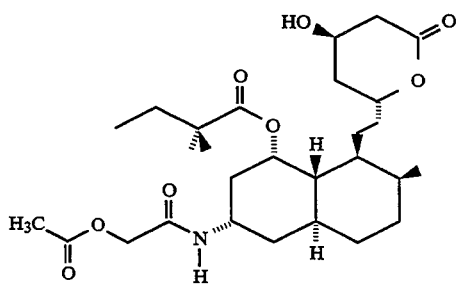

A solution of the title product (260 mg, 0.404 mmol) prepared in step (a) above in EtOAc was treated with AcOH (catalytic trace) followed by $Pd(OH)_2/C$ (cat.). The solution was degassed with argon and bubbled vigorously with $H_2$. The reaction was followed by thin-layer chromatography. The solution was filtered through a short pad of Celite and treated with aq. sat'd. $NaHCO_3$. The solvent was removed by evaporation and the residue purified on $SiO_2$ using 40% EtOAc/60% hexane yielding the title product as a colorless oil ($C_{28}H_{45}O_8N$, 182 mg, 0.348 mmol, % theory=86%).

EXAMPLE 10

Preparation of [1S-[1α(βS*,δS*),2α,4aβ,6β,8β,8aα]]-8-(2,2-Dimethyl-1-1-oxobutoxy)decahydro-β,δ-dihydroxy-6-[(hydroxyacetyl)amino]-2-methyl-1-naphthaleneheptanoic acid, monolithium salt

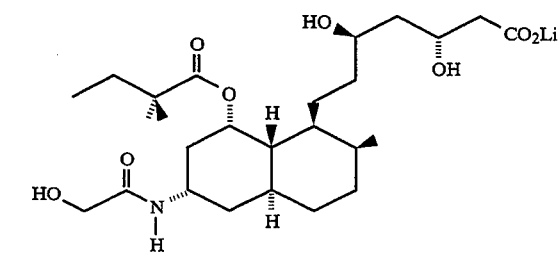

A solution of the acetoxy title product (182 mg, 0.348 mmol) prepared in step (b) of Example 9 above was dissolved in a solution of $CH_3CN/H_2O$ (10:1) and treated with 1N LiOH (1.044 mmol, 1.044 ml) and stirred for 2 hours. The solution was concentrated by evaporation and purified on CHP-20P gel using 20% $CH_3CN$/80% $H_2O$ as the mobile phase. The solution was concentrated to $H_2O$, frozen and lyophilized over a weekend to give the title compound as a white lyophilate. ($C_{26}H_{44}NO_8Li$, 150 mg, % theory=85%), colorless oil, $[\alpha]_D = +81.4°$ (c=0.50, MeOH), TLC: $R_f$=0.50 on $SiO_2$ using 8:1:1 ($CH_2Cl_2$:MeOH:AcOH): developed using a 10% solution of phosphomolybdic acid in ethanol).

Elemental Analysis (%) for $C_{26}H_{44}NO_8Li \cdot 3.08\ H_2O$

| | Calc. | Found |
|---|---|---|
| C | 55.65 | 56.03 |
| H | 9.01 | 9.01 |
| N | 2.50 | 2.12 |

EXAMPLE 11

Preparation of [1S-[1α,3α,4aα,7β,8β(2S*,4S*),8aβ]]-2,2-Dimethylbutanoic acid, 3-[(trifluoroacetyl)amino]decahydro-7-methyl-8-[2-(tetrahydro-4-hydroxy-6-oxo-2H-pyran-2-yl)ethyl-1-naphthalenyl ester (a) [1S-[1α,3α,4aα,7β,8β(2S*,4S*),8aβ]]-2,2-Dimethylbutanoic acid, 3-[(trifluoroacetyl)amino]-decahydro-7-methyl-8-[2-[tetrahydro-4-[(phenylmethoxy)methoxy]-6-oxo-2H-pyran-2-yl]-ethyl]-1-naphthalenyl ester

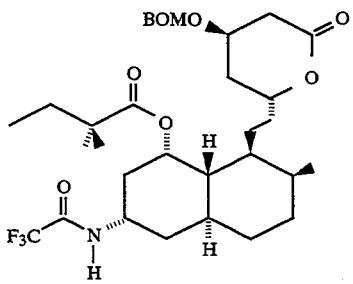

A solution of the amine title product prepared in step (b) of Example 1 above (1.09 mmol, 595 mg) in CH$_2$Cl$_2$ was treated with trifluoroacetic anhydride (2 ml, 14 mmol) at room temperature. The reaction mixture was stirred for ½ hour. The reaction mixture was diluted with EtOAc and washed with NaHCO$_3$. The organic layer was washed with brine and dried over MgSO$_4$. The solvent was removed by evaporation to give a yellow oil. Purification by column chromatography using 70% EtOAc/30% hexane on SiO$_2$. The title product was obtained as a white solid foam (C$_{34}$H$_{48}$O$_7$NF$_3$, yield=162 mg pure/224 impure, % theory=~55%, 0.603 mmol).

(b) [1S-[1α,3α,4aα,7β,8β(2S*,4S*), 8β]]-2,2-Dimethylbutanoic acid, 3-(trifluoroacetyl)amino]-decahydro-7-methyl-8-[2-(tetrahydro-4-hydroxy-6-oxo-2H -pyran-2-yl)ethyl]-1-naphthalenyl ester

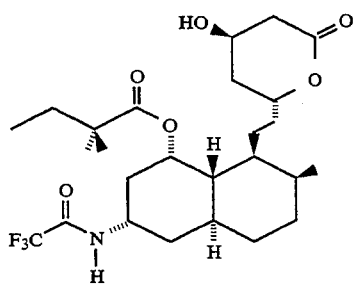

A solution of the trifluoroacetamide title product prepared in step (a) above in EtOAc (162 mg, 0.25 mmol) was treated with a few drops of AcOH (cat.) and a spatula of Pd(OH)$_2$/C. The solution was degassed with argon for 5 minutes. The solution was then treated with H$_2$ by bubbling from an Orsat gas bag. The reaction was completed in ½ hour. The solution was filtered through a short pad of Celite with EtOAc. The solution was treated with saturated NaHCO$_3$. The organic fraction was washed with brine and dried over MgSO$_4$. The solution was filtered and solvent was removed by evaporation. Purification by column chromatography on SiO$_2$ using 25% EtOAc/75% hexane yielded a white solid. The same procedure was performed for the impure fraction. The title product was obtained as a white solid foam (C$_{26}$H$_{40}$O$_6$, yield=200 mg, 0.394 mmol, % theory=~65% (combined)).

EXAMPLE 12

Preparation of
[1S-[1α(βS*,δS*),2α,4aβ,8β,8aα]]-6-Amino-8-(2,2-dimethyl-1-oxo-butoxy)decahydro-β,δ-dihydroxy-2-methyl-1-naphthaleneheptanoic acid, monolithium salt

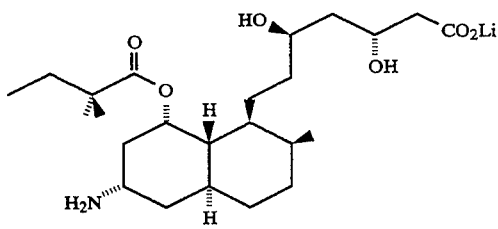

A solution of the trifluoroacetamide lactone prepared as the title product in step (b) of Example 11 above (200 mg, 0.394 mmol) in CH$_3$CN/H$_2$O ~(3:1) was treated (with stirring) with 2 eq. 1N LiOH (0.788 mmol, 788 μL). Another equivalent of 1N LiOH (400 μl, 400 mmol) was added and the reaction mixture was stirred for another hour. The solvent was removed by evaporation and the sample was loaded in H$_2$O on a CHP-20P column, using 1) H$_2$O; 2) 5% aq. CH$_3$CN; 3) 10% aq. CH$_3$CN (title compound); 4) 30% aq. CH$_3$CN as mobile phase. The relevant fractions were combined, solvent was reduced and the sample was lyophilized to yield the title product as a white lyophilate (CH$_{24}$H$_{42}$O$_6$NLi, [α]$_D$ = +53.5° (c=0.48, MeOH), yield=170 mg, % theory=96%, TLC: R$_f$=0.35 on SiO$_2$ using 8:1:1 (CH$_2$Cl$_2$:MeOH:AcOH): developed using a 10% solution of phosphomolybdic acid in ethanol).

Elemental Analysis (%) for CH$_{24}$H$_{42}$O$_6$NLi·0.79 H$_2$O

|   | Calc. | Found |
|---|---|---|
| C | 62.44 | 62.35 |
| H | 9.51 | 9.81 |
| N | 3.03 | 3.12 |

EXAMPLE 13

Preparation of
[1S-[1α,3α,4aα,7β,8β(2S*,4S*),8aβ]]-2,2-Dimethylbutanoic acids, 3-[(methoxycarbonyl)amino]decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-[(methoxycarbonyl)amino]-decahydro-7-methyl-8-[2-[tetrahydro-4-[(phenylmethoxy)methoxy]-6-oxo-2H-pyran-2-yl]-ethyl]-1-naphthalenyl ester

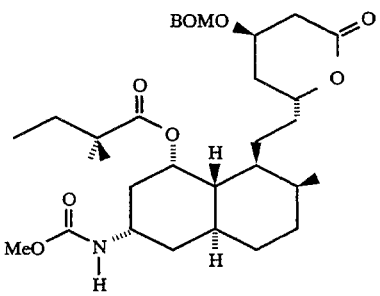

A solution of the amine title product prepared in step (b) of Example 1 above (300 mg, 0.55 mmol) was dissolved in CH$_2$Cl$_2$ (10 ml) and treated with diisopropylethylamine (214 mg, 288 μl and placed under argon. The solution was then treated with methyl chloroformate (0.825 mmol, 64 μL) and stirred at room temperature for ½ hour. The solvent was removed by evaporation and the residue was purified on SiO$_2$ using 35% EtOAc/65% hexane as the mobile phase. The title product was obtained as a colorless oil (C$_{34}$H$_{51}$O$_8$N , yield=235 mg, 0.39 mmol, % theory=72%).

(b) [1S-[1α,3α,4aα,7β,8β(2S*,4S*),8aβ]]-2,2-Dimethylbutanoic acid, 3-[(methoxycarbonyl)amino]-decahydro-7-methyl-8-[2-(tetrahydro-4-hydroxy-6-oxo-2H-pyran-2-yl)ethyl]-1-naphthalenyl ester

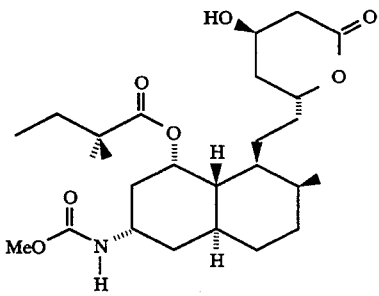

A solution of the BOM-urethane prepared in step (a) above (235 mg, 0.39 mmol) in EtOAc was treated with a catalytic amount of AcOH (a few drops) and then Pd(OH)$_2$/C. The solution was then bubbled vigorously with H$_2$ (g). The reaction was followed by TLC. The solution was filtered through a short pad of Celite, the residue was diluted with EtOAc and washed with H$_2$O followed by saturated NaHCO$_3$. The organic fraction was washed with brine and dried over MgSO$_4$. The solution was filtered and the solvent was removed by evaporation. The residue was purified on SiO$_2$ using 70% EtOAc/30% hexane as the mobile phase. The title product was obtained as white needles (C$_{26}$H$_{43}$O$_7$N, yield=140 mg, % theory=74%).

EXAMPLE 14

Preparation of
[1S-[1α(βS*,δS*),2α,4aβ,6β,8β,8aα]]-8-(2,2-Dimethyl-1-oxobutoxy)decahydro-β,δ-dihydroxy-6-[(methoxycarbonyl)amino]-2-methyl-1-naphthaleneheptanoic acid, monolithium salt

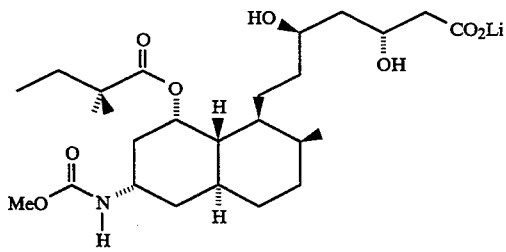

A solution of the urethane prepared as the title product in step (b) of Example 13 above (140 mg, 0.29 mmol) was dissolved in CH$_3$CN/H$_2$O and treated with 2 eq. 1N LiOH (0.58 mmol, 580 μl). The solution was stirred for 2 hours and then solvent was removed by evaporation. The residue was purified on CHP-20P resin using 1) H$_2$O to remove LiOH; 2) 20% CH$_3$CN in H$_2$O as the mobile phase. The appropriate fractions were concentrated and lyophilized overnight.

The title product was obtained as a white lyophilate (C$_{26}$H$_{44}$NO$_8$Li, yield=100 mg, 0.20 mmol, % theory=69%, [α]$_D$ = +61.4° (c=0.36, MeOH), TLC: R$_f$=0.65 on SiO$_2$ using 8:1:1 (CH$_2$Cl$_2$:MeOH:AcOH): developed using a 10% solution of phosphomolybdic acid in ethanol)

Elemental Analysis (%) for C$_{26}$H$_{44}$NO$_8$Li.1.07H$_2$O

|   | Calc. | Found |
|---|---|---|
| C | 59.50 | 59.52 |
| H | 8.86 | 9.24 |

-continued

|   | Calc. | Found |
|---|---|---|
| N | 2.67 | 2.65 |

EXAMPLE 15

Preparation of
[1S-[1α(βS*,δS*),2α,4aβ,6β,8β,8aα]]-6-[[(Methylamino)carbonyl]amino]-8-(2,2-dimethyl-1-oxobutoxy)decahydro-β,δ-dihydroxy-2-methyl-1-naphthaleneheptanoic acid, monolithium salt and

[1S-[1α(βS*,δS*),2α,4aβ,6β,8β,8aα]]-6-[[(Dimethylamino)carbonyl]amino]-8-(2,2-dimethyl-1-oxobutoxy)decahydro-β,δ-dihydroxy-2-methyl-1-naphthaleneheptanoic acid, monolithium salt (a) [1S-[1α,3α,4aα,7β,8β(2S*,4S*),8aβ]]-2,2-Dimethylbutanoic acid, 3-[[(methylamino)carbonyl]amino]decahydro-7-methyl-8-[2-[tetrahydro-4-[(phenylmethoxy)methoxy]-6-oxo-2H-pyran-2-yl]ethyl]-1-naphthalenyl ester

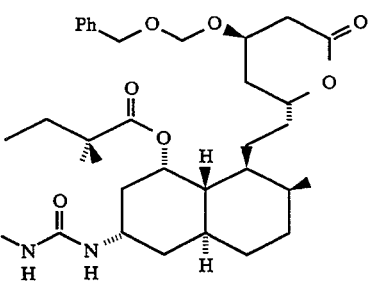

A solution of the amine prepared as in step (b) of Example 1 above (215 mgs, 0.395 mmol) in CH$_2$Cl$_2$ (8 ml) was cooled in an ice/water bath and treated with methyl isocyanate (CH$_3$—N=C=O, 35 μl, 0.593 mmol). The reaction mixture was allowed to warm to room temperature and stirred for ½ hour. The solvent was removed by evaporation and the residue purified by column chromatography on silica gel using 80% EtOAc/20% hexane as the mobile phase. The title product was obtained as a white foam (C$_{34}$H$_{52}$N$_2$O$_7$, yield=177 mgs, % theory=75%, (M+H)+ =601).

(b) [1S-[1α(βS*,δS*),2α,4aβ,6β,8β,8aα]]-6-[[(Methylamino)carbonyl]amino]-8-(2,2-di-2-methyl-1-oxobutoxy)decahydro-β,δ-dihydroxy-2-methyl-1-naphthaleneheptanoicacid, mono lithium salt and

[1S-[1α(βS*,δS*),2α,4aβ,6β,8β,8aα]]-6-[[(dimethylamino) carbonyl]amino]-8-(2,2-dimethyl-1-oxobutoxy)decahydro-β,δ-dihydroxy-2-methyl-1-naphthaleneheptanoic acid, monolithium salt A solution of the title compound prepared in step (a) above (170 mgs, 0.283 mmol) in EtOAc (15 ml) and AcOH (½ ml) was treated with 20% Pd(OH)$_2$/C (20 mgs) and H$_2$ bubbled gently through the reaction mixture for ½ hour. A further portion of 20% Pd(OH)$_2$/C was added (20 mgs) and H$_2$ bubbled through the reaction mixture. The reaction was filtered through a pad of celite, washed with saturated NaHCO$_3$ (5 ml), brine (5 ml), dried (MgSO$_4$) and the solvent removed by evaporation to give an insoluble white solid.

The solid and THF (5 ml)/H₂O (2 ml) was treated with 1N LiOH aq. (424 μl, 424 mmol) and stirred at room temperature for ½ hour. The reaction mixture was concentrated, placed on a CHP-20P/water column and eluted with 1) H₂O (to remove excess LiOH)
2) 10% MeCN/90% H₂O yielding the title [(methylamino)carbonyl]amino compound:

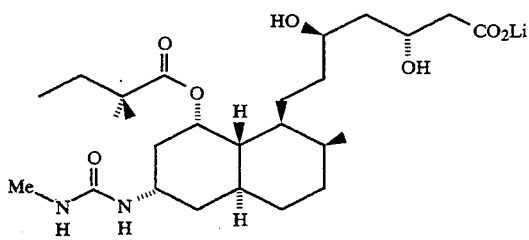

as a minor product (C₂₆H₄₅N₂O₇Li, white lyophilate, 24 mgs yield, 16% theory, [α]$_D$= +53.2 (c=0.27, MeOH); and the title [(dimethylamino)carbonyl]amino compound:

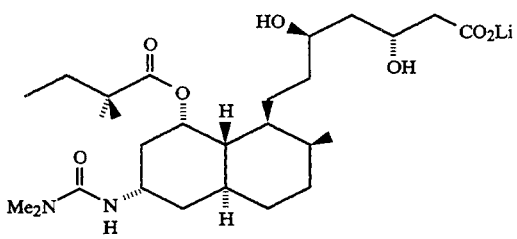

the manor product; and 3) 20% acetonitrile/80% H₂O yielding the above title [(dimethylamino)carbonyl]amino compound (C₂₇H₄₇N₂O₇Li, white lyophilate, 41 mgs, 28% theory, [α]$_D$= +59.5° (c=0.36, MeOH), TLC: R$_f$=0.25 (on silica gel using 10:10:80 AcOH/MeOH/CH₂Cl₂, developed using ~5% phosphomolybdic acid in ethanol); Elemental Analysis (%) (calculated for C₂₇H₄₇N₂O₇Li.2.26 H₂O)

|   | Calc. | Found |
|---|-------|-------|
| C | 57.97 | 58.23 |
| H | 9.28  | 9.10  |
| N | 5.01  | 4.75  |

EXAMPLE 16

Preparation of [1S-[1α,3α,4aα,7β,8β-(2S*,4S*),8aβ]]-2,2-Dimethylbutanoic acid,3-(acetylamino)decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-(acetylamino)decahydro-7-methyl-8-[2-[tetrahydro-4-[(phenylmethoxy)methoxy]-6-oxo-2H-pyran-2-yl]ethyl]-1-naphthalenyl ester

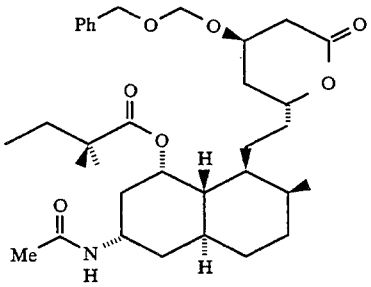

A solution of the amine prepared in step (b) of Example 1 above (181 mgs, 0.333 mmol) and pyridine (27 μl, 0.333 mmol) in CH₂Cl₂ was treated with acetic anhydride (63 μl, 0.666 mmol) and stirred at room temperature for 2½ hours. The solvent was removed by evaporation to give an oil which was purified by column chromatography on silica gel using 55% EtOAc/45% hexane as the mobile phase. The title product was obtained as a white foam (C₃₄H₅₁NO₇, 148 mgs, 76% theory, (M+H)⁺=586).

(b) [1S-[1α,3α,4aα,7β,8β(2S*,4S*),8aβ]]-2,2-Dimethylbutanoic acid, 3-(acetylamino)decahydro-7-methyl-8-[2-(tetrahydro-4-hydroxy-6-oxo-2H-pyran-2-yl)ethyl]-1-naphthalenyl ester

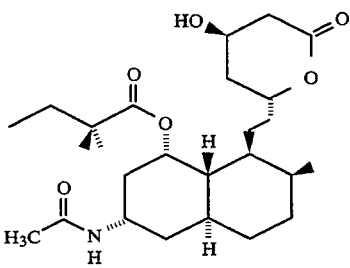

A solution of the acetamide prepared in step (a) above (230 mgs, 0.393 mmol) in EtOAc (20 ml)/AcOH (½ ml) was treated 20% Pd(OH)₂/C (catalytic). The reaction mixture was degassed with Ar, and H₂ gas bubbled through the solution. The reaction was filtered through celite (washing with MeOH), concentrated by evaporation and redissolved in EtOAc. The organic solution was washed with saturated NaHCO₃, brine, (MgSO₄) and the solvent removed by evaporation to afford the title product (170 mgs, 93%).

EXAMPLE 17

Preparation of
1S-[1α(βS*,δS*),2α,4aβ,6β,8β,8aα]]-6-(Acetylamino)-8-(2,2-dimethyl-1-oxobutoxy)-decahydro-β,δ-dihydroxy-2-methyl-1-naphthaleneheptanoic acid, monolithium salt

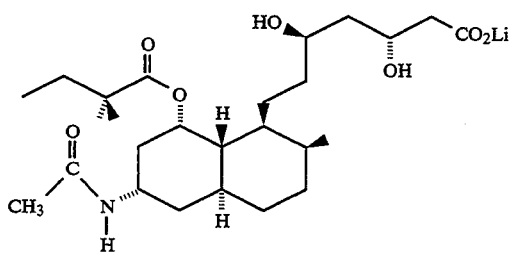

A solution of the lactone prepared as the title product in step (b) of Example 16 above (170 mgs, 0.365 mmol) in MeCN (5 ml)/THF (5 ml)/H$_2$O (4 ml) was treated with 1N LiOH (aq.) (730 μl, 0.730 mmol) and stirred for 2 hours. The reaction mixture was concentrated and purified by chromatography on CHP-20P using 1) H$_2$O; 2) 20% MeCN/80% H$_2$O as the mobile phases. The fractions containing product were concentrated by evaporation, filtered through a 0.3 μm cellulose nitrate filter and the water removed by freeze drying to give the title product as a white lyophilate. (C$_{26}$H$_{44}$O$_7$NLi (125 mgs, 70%) [α]$_D$=+46.8° (c=0.4, MeOH), TLC: R$_f$=0.35 (80:10:10—CH$_2$Cl$_2$:AcOH:MeOH)

Elemental Analysis (%) Calculated for C$_{26}$H$_{44}$O$_7$N-Li.1.16 H$_2$O

|   | Calc. (% corr. for H$_2$O) | Found |
|---|---|---|
| C | 61.17 | 61.23 |
| H | 9.15  | 9.11  |
| N | 2.74  | 2.68  |

EXAMPLE 18

Preparation of
[1S-[1α,3α,4aα,7β,8β(2S*,4S*),8aβ]]-2,2-Dimethylbutanoic acid, 3-(formylamino)decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-(formylamino)decahydro-7-methyl-8-[2-[tetrahydro-4-[(phenylmethoxy)methoxy]-6-oxo-2H-pyran-2-yl]ethyl]-1-naphthalenyl ester

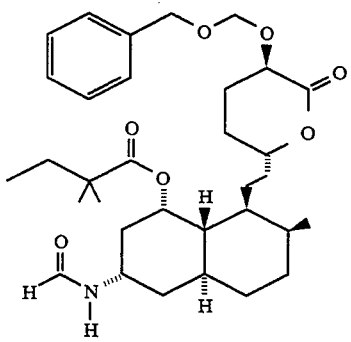

Formic acid (111 μl, 2.94 mmol) was added dropwise to acetic anhydride (226 μl, 2.29 mmol) at 0° C. After the addition, the cooling bath was removed and the reaction was heated to 50° C. (oil bath temperature) for 2 hours producing acetic formic anhydride. After cooling the reaction to room temperature, THF (5 ml) was added. The reaction was then cooled to −10° C. and a −10° C. solution of the amine prepared in step (b) of Example 1 above in THF (5 ml) was added. After 15 minutes, the reaction mixture was concentrated and chromatographed on silica gel eluting with 1:1 EtOAc/hexanes (1L) followed by 60:40 EtOAc/hexanes (500 ml). Fractions containing the formamide product were combined and concentrated in vacuo to give 448.9 mg (84%) of a colorless oil.

(b) [1S-[1α,3α,4aα,7β,8β(2S*,4S*),8aβ]]-2,2-Dimethylbutanoic acid, 3-(formylamino)decahydro-7-methyl-8-[2-(tetrahydro-4-hydroxy-6-oxo-2H-pyran-2-yl)ethyl]-naphthalenyl ester

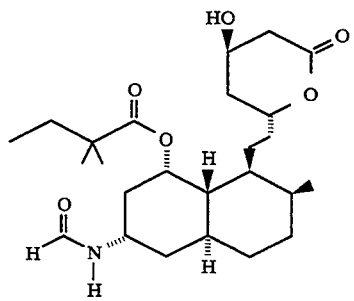

A solution of the formamide (300.3 mg, 0.525 mmol) prepared in step (a) above in 6 ml EtOAc was degassed. To this solution was added Pd(OH)$_2$/C (60 mg) and the mixture was degassed. The flask was evacuated and filled with H$_2$ via a balloon (repeated 2×). After one hour, the reaction was ca. 50% complete by TLC analysis. Over the next hour, no significant progress in the reaction was observed. Additional Pd(OH)$_2$/C (~20 mg) was added. After 40 minutes, the reaction was ca. 60% complete. The mixture was filtered through a pad of Celite, washing with EtOAc. The filtrate was concentrated and stored overnight at −40° C.

After warming to room temperature, the solution was then degassed and Pd(OH)$_2$/C (70 mg) was added. The mixture was resubjected to H$_2$ as described above. After 2 hours, the reaction mixture was filtered through a pad of Celite, washing with EtOAc followed by acetone. The crude product was chromatographed on Merck silica gel (70:1), eluting with 10% hexanes/90% EtOAc. A very small amount of higher R$_f$ material

EXAMPLE 19

Preparation of
[1S-[1α(βS*,δS*),2α,4aβ,6β,8β,8aα]]-8-(2,2-Dimethyl-1-oxobutoxy)-6-(formylamino)decahydro-β,δ-dihydroxy-2-methyl-1-naphthaleneheptanoic acid, monolithium salt

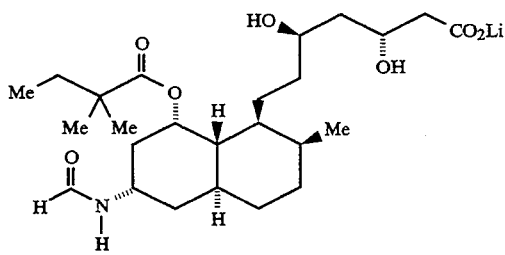

A 0° C. suspension of the formamide (178.0 mg, 0.394 mmol) prepared in step (b) of Example 18 above in 1.5 ml of dioxane was treated dropwise with 1N LiOH (473 μl, 0.473 mmol). The cooling bath was removed immediately. The starting formamide slowly went into solution over 30 minutes.

After stirring for another 10 minutes, the reaction mixture was concentrated. The crude product was chromatographed on CHP-20P resin, eluting with $H_2O$ (200 ml), 5% $CH_3CN$ in $H_2O$ (50 ml), 10% $CH_3CN$ in $H_2O$ (100 ml), 15% $CH_3CN$ in $H_2O$ (100 ml), and then 20% $CH_3CN$ in $H_2O$ (200 ml). Fractions containing the title product were combined and concentrated in vacuo. The product was dissolved in $H_2O$ and filtered through a 3.0 μm cellulose nitrate filter, and the aqueous solution was freeze-dried to yield a white lyophilate. ($C_{25}H_{42}NO_7Li$, yield: 181.1 mg (97%).) Two rotomers of the formamide were observed by $^1H$ NMR analysis; one minor and the other major. $[\alpha]_D = +23.1°$ (c=0.50, MeOH) TLC:$R_f$=0.21 on silica gel using 20:1:1 $CH_2Cl_2$:MeOH:AcOH); PMA in EtOH stain.

Elemental Analysis (%) for $C_{25}H_{42}NO_7Li \cdot 1.22\ H_2O$

|   | Calc. (% Corr. H₂O) | Found |
|---|---|---|
| C | 60.35 | 60.75 |
| H | 9.00 | 9.09 |
| N | 2.82 | 2.42 |

EXAMPLE 20

Preparation of
[1S-[1α,3α,4aα,7β,8β-(2S*,4S*),8aβ]]-2,2-Dimethylbutanoic acid,3-[[(dimethylamino)sulfonyl]amino]decahydro-7-methyl-8-[2-(tetrahydro-4-hydroxy-6-oxo-2H-pyran-2-yl)ethyl-1-naphthalenyl ester (a) [1S-[1α,3α,4aα,7β,8β(2S*,4S*),8aβ]]-2,2-Dimethylbutanoic acid, 3-[[(dimethylamino)sulfonyl]amino]decahydro-7-methyl-8-[2-[tetrahydro-4-[(phenylmethoxy)methoxy]-6-oxo-2H-pyran-2-yl]ethyl-1-naphthalenyl ester

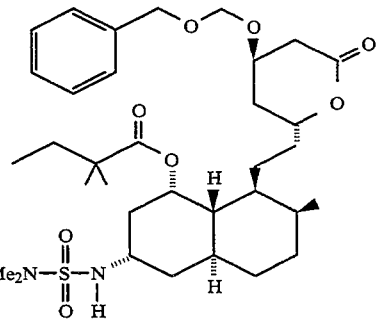

A 0° C. solution of the amine (348.2 mg, 0.640 mmol) prepared as the title product in step (b) of Example 1 above in 6 ml dry $CH_2Cl_2$ was treated with Hunigs base (134 μl, 0.768 mmol), followed by dimethylsulfamoyl chloride (($CH_3)_2NSO_2Cl$, 75.7 μl, 0.704 mmol), and a few milligrams of 4-dimethylaminopyridine (DMAP). After stirring at 0° C. for 5 minutes, the cooling bath was removed. After 45 hours, the reaction mixture was diluted with EtOAc and washed with 5% $KHSO_4$ and brine. The organic layer was dried ($Na_2SO_4$), filtered, and the filtrate concentrated in vacuo. The crude produce was chromatographed on Merck silica gel (100:1), eluting with 30% EtOAc in hexanes (100 ml) and then 35% EtOAC in hexanes (200 ml). The title product was isolated as a colorless oil in a yield of 345.7 mg (83%).

(b) [1S-[1α,3α,4aα,7β,8β(2S*,4S*),8aβ]]-2,2-Dimethylbutanoic acid, 3-[[(dimethylamino)sulfonyl]amino]decahydro-7-methyl-8-[2-(tetrahydro-4-hydroxy-6-oxo-2H-pyran-2-yl)-ethyl-1-naphthalenyl ester

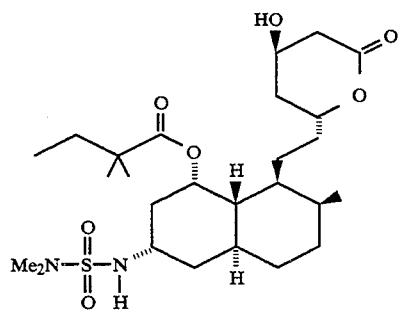

TO a degassed solution of the dimethylaminosulfamide (336.5 mg, 0.517 mmol) prepared as the title product in step (a) above in 6 ml EtOAc was added 70 mg of Pd(OH)₂/C. This mixture was evacuated and H₂ was introduced via a balloon (repeated 2×). After stirring for 35 hours, the reaction mixture was filtered through a pad of Celite, washing with EtOAc, and the filtrate was concentrated. The crude product was chromatographed on Merck silica gel (100:1), eluting with 35:65 hexanes/EtOAc. Fractions containing the title product were combined and concentrated in vacuo. ($C_{26}H_{46}N_2O_7S$, yield: 242.0 mg (88%)).

EXAMPLE 21

Preparation of
[1S-[1α(βS*,δS*),2α,4aβ,6β,8β,8aβ]]-6-[[(Dimethylamino)sulfonyl]amino]-8-(2,2dimethyl-1-oxobutoxy)decahydro-β,δ-dihydroxy-2-methyl-1-naphthaleneheptanoic acid, monolithium salt

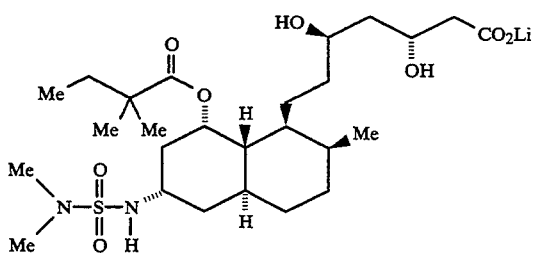

A cooled (0° C.) solution of the dimethylaminosulfamide title product (233.1 mg, 0.439 mmol) prepared in step (b) of Example 20 above in 800 μl of dioxane was treated dropwise with 1N LiOH (527 μl, 0.527 mmol). The cooling bath was removed after 20 minutes. After stirring for 1 hour at room temperature, starting material remained. Additional 1N LiOH (3×88 μl, 0.088 mmol) was added in portions over 1.25 h until complete consumption of starting material was achieved.

The reaction mixture was concentrated and chromatographed on CHP-20P resin, eluting with H$_2$O (300 ml), 5% CH$_3$CN in H$_2$O (50 ml), 10% CH$_3$CN in H$_2$O (100 ml), 15% CH$_3$CN in H$_2$O (100 ml), 20% CH$_3$CN in H$_2$O (200 ml), and then 25% CH$_3$CN in H$_2$O (200 ml). The fractions containing pure product were concentrated and the residue was taken up in H$_{20}$. The aqueous solution was filtered through a 3.0 μm cellulose nitrate filter and lyophilized yielding a white lyophilate. (C$_{26}$H$_{47}$N$_2$O$_8$SLi, yield: 201.5 mg (83%), [α]$_D$= +52.2° (c=0.50, MeOH), TLC:R$_f$=0.42 on silica gel using 20:1:1 CH$_2$Cl$_2$:MeOH:AcOH); PMA in EtOH stain).

Elemental Analysis (%) for C$_{26}$H$_{47}$N$_2$O$_8$SLi.1.18 H$_2$O

|   | Calc. | Found |
|---|---|---|
| C | 54.22 | 54.02 |
| H | 8.64 | 8.62 |
| N | 4.86 | 5.06 |
| S | 5.57 | 5.97 |

EXAMPLE 22

Preparation of
[1S-[1α,3α,4aα,7β,8β(2S*,4S*),8aβ]]-2,2-Dimethylbutanoic acid, 3-[[(methylamino)sulfonyl]amino]decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-[[(methylamino)sulfonyl]amino]decahydro-7-methyl-8-[2-[tetrahydro-4-[(phenylmethoxy)methoxy]-6-oxo-2H -pyran-2-yl]-ethyl]-1-naphthalenyl ester

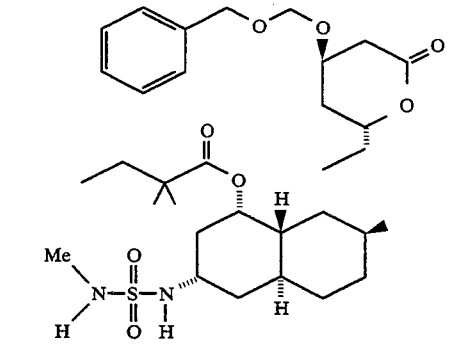

A suspension of methylsulfamic acid (242 mg, 2.18 mmol) in 2 ml dry toluene was treated with PCl$_5$ (453 mg, 2.18 mmol) (CH$_3$N(H)SO$_3$H+PCl$_5$→CH$_3$N(H-)SO$_2$Cl). The mixture was heated at 85° C. (oil bath temperature). After stirring for 45 minutes, the mixture became homogenous and nearly colorless. The reaction mixture was allowed to stir for an additional 15 minutes and then it was allowed cool. After cooling, the mixture was concentrated and placed under high vacuum (about 15 mm) for 1.5 hours.

A solution of the amine (394.7 mg, 0.726 mmol) prepared as the title product in step (b) of Example 1 above and Hunigs base (443 μl, 2.54 mmol) in 4 ml dry CH$_2$Cl$_2$ at 0° C. was treated with the above-prepared suspension of methylsulfamoyl chloride in 2 ml dry CH$_2$Cl$_2$ at 0° C. via a pipet. Some solid was not transferred.

After stirring for 20 minutes, the reaction mixture was diluted with EtOAc and washed with 5% KHSO$_4$ followed by brine. The organic layer was dried (Na$_2$SO$_4$), filtered, and the filtrate concentrated. The crude product was chromatographed on Merck silica gel (100:1), eluting with 43% EtOAc in hexane. The title compound was isolated in slightly impure form (as evidenced by $^1$H NMR analysis) in a yield of 347.0 mg (75%) as a colorless oil.

(b) [1S-[1α,3α,4aα,7β,8β(2S*,4S*),8aβ]]-2,2-Dimethylbutanoic acid, 3-[[(methylamino)sulfonyl]amino]decahydro-7-methyl-8-[2-(tetrahydro-4-hydroxy-6-oxo-2H-pyran-2-yl)ethyl]-1-naphthalenyl ester

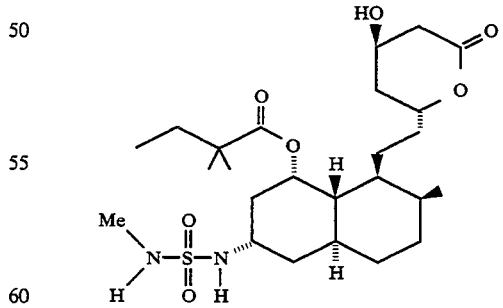

To a degassed solution of the monomethylamino sulfamide (321.0 mg, 0.504 mmol) prepared as the title product in step (a) above in 6 ml EtOAc was added Pd(OH)$_2$/C (65 mg). Hydrogen was bubbled through this mixture via a balloon connected to a needle. After stirring for 2 hours, more Pd(OH)$_2$/C (ca. 20 mg) was added. After stirring for another 1 hour, the reaction mixture was filtered through a pad of Celite, washing with EtOAc and the filtrate was concentrated. The crude product was chromatographed on Merck silica gel (100:1), eluting with 1:1 CH$_2$Cl$_2$:EtOAc. An inefficient separation resulted. Additional chromatographies with 1:1 EtOAc/CH$_2$Cl$_2$ and 2–2.5% MeOH in CH$_2$Cl$_2$ and then recrystallization from EtOAc/hexanes were performed to obtain 140.8 mg (51%) of pure title product as a white crystalline solid. (C$_{25}$H$_{44}$N$_2$O$_9$).

EXAMPLE 23

Preparation of
[1S-[1α(βS*,δS*),2α,4aβ,6β,8β,8aβ]]-8-(2,2-Dimethyl-1-oxobutoxy)decahydro-β,δ-dihydroxy-2-methyl-6-[[(methylamino)sulfonyl]amino]-1-naphthaleneheptanoic acid, monolithium salt

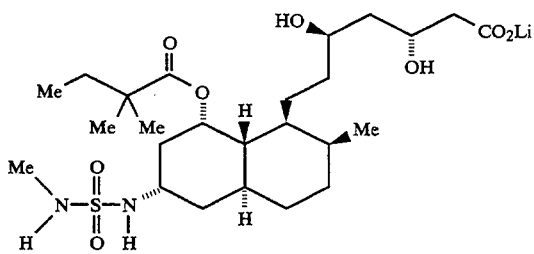

To a cooled (0° C.) solution of the lactone (136.2 mg, 0.264 mmol) prepared as the title product in step (b) of Example 22 above in 800 μl of dioxane was added 1N LiOH (316 μl, 0.316 mmol) dropwise. The cooling bath was removed. After stirring for 5 minutes the reaction mixture was concentrated. The crude product was chromatographed on CHP-20P gel, eluting with H$_2$O (200 ml), followed by 5% CH$_3$CN in H$_2$O (50 ml), 10% CH$_3$CN in H$_2$O (100 ml), 15% CH$_3$CN in H$_2$O (100 ml), 20% CH$_3$CN in H$_2$O (200 ml), and 25% CH$_3$CN in H$_2$O (200 ml). Fractions containing the desired title product were combined and concentrated. The residue was redissolved in H$_2$0, and the aqueous solution was filtered through a 3.0 μm cellulose nitrate filter and lyophilized yielding 133.3 mg (94%) of a white lyophilate. (Opt. Rot.: [α]$_D$ = +51.2° (c=0.50, MeOH); TLC: R$_f$=0.20 on silica gel using 20:1:1 CH$_2$Cl$_2$:MeOH: AcOH; PMA in EtOH stain).

Elemental Analysis (%) for C$_{25}$H$_{45}$N$_2$O$_8$SLi.0.83 H$_2$O

|   | Calc. | Found |
|---|---|---|
| C | 54.04 | 54.21 |
| H | 8.46 | 8.45 |
| N | 5.04 | 4.87 |
| S | 5.77 | 5.79 |

EXAMPLE 24

Preparation of
[1S-[1α,3α,4aα,7β,8β(2S*,4S*),8aβ]]-2,2-Dimethylbutanoic acid, 3-(dimethylamino)decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-(dimethylamino)decahydro-7-methyl-8-[2-[tetrahydro-4[(phenylmethoxy)me-thoxy]-6-oxo-2H-pyran-2-yl]-ethyl]-1-naphthalenyl ester

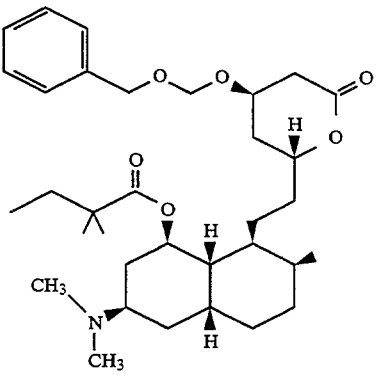

A solution of the amine prepared as the title product in step (b) of Example 1 above (0.4665 g, 0.858 mmol) in MeOH (3.5 ml) was added to a suspension of aqueous formaldehyde (37 wt. % in H$_2$O, 1.3 ml, 17.5 mmol) and Pd(OH)$_2$—C (0.01 g) in MeOH (7.5 ml). The reaction flask was briefly evacuated, then H$_2$ was introduced via balloon. After stirring at room temperature under the H$_2$ atmosphere for 5.5 hours, TLC indicated the reaction was nearly complete. Additional formaldehyde (0.50 ml, 6.7 mmol) and Pd(OH)$_2$—C (0.01 g) were added and the reaction flask evacuated and purged with H$_2$. After stirring at room temperature for 1 hour the reaction was filtered through Celite and the residue was rinsed with MeOH (5 ml) and EtOAc (5 ml). The filtrate was concentrated in vacuo. The residue was dissolved in EtOAc (25 ml) and then washed with saturated NaHCO$_3$ (5 ml), H$_2$O (5 ml) and brine (5 ml). The organic layer was dried (Na$_2$SO$_4$) and filtered through a pad of MgSO$_4$. The filtrate was concentrated in vacuo to give an oil which was purified by column chromatography on silica gel eluting with 3% MeOH in CH$_2$Cl$_2$ to give the desired title product (0.3633 g, 74%) as an oil. TLC R$_f$=0.30 (silica gel; 8% MeOH in CH$_2$Cl$_2$); 15% phosphomolybdic acid in EtOH stain.

(b) [1S-[1α,3α,4aα,7β,8β(2S*,4S*),8aβ]]-2,2-Dimethylbutanoic acid, 3-(dimethylamino)decahydro-7-methyl-8-[2-(tetrahydro-4-hydroxy-6-oxo-2H-pyran-2-yl)ethyl]-1-naphthalenyl ester

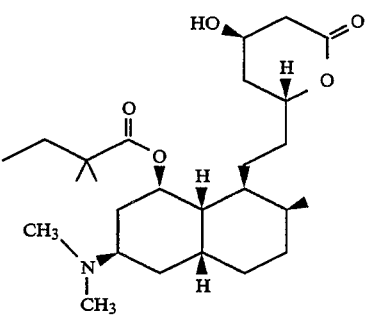

To a solution of the dimethylamino title product prepared in step (a) above (0.349 g, 0.61 mmol) in EtOAc (10 ml) was added trifluoroacetic acid (100 μl) and Pd(OH)$_2$—C (0.01 g). The reaction vessel was evacuated and H$_2$ was introduced via balloon. The evacuation and H$_2$ introduction were repeated two times more. After stirring at room temperature for 17 hours, TLC indicated only a small amount of product had formed. Fresh Pd(OH)$_2$—C (0.01 g) and more trifluoroacetic acid (20 μl) were added, and H$_2$ introduced as described above. After 4 hours at room temperature, a solution of the dimethylamino starting material (0.037 g, 0.06 mmol) in EtOAc (1 ml) was added to the reaction along with fresh catalyst (0.01 g). The reaction was hydrogenated as above for 2.5 hours, filtered through Celite and rinsed well with EtOAc (10 ml). The filtrate was stored at −40° C. for 18 hours. Fresh Pd(OH)$_2$—C (0.01 g) was added to the filtrate followed by more trifluoroacetic acid (50 μl).

The reaction was hydrogenated as above for 5.5 hours, filtered through Celite and rinsed well with EtOAc (15 ml). The filtrate was washed with saturated NaHCO$_3$ (3×10 ml), H$_2$O (10 ml) and brine (10 ml), dried (Na$_2$SO$_4$) and filtered through a pad of MgSO$_4$. The filtrate was concentrated in vacuo to give a clear oil which was purified by column chromatography on silica gel eluting with 20% acetone in EtOAc to give the desired title produce in two fractions (0.100 g, 33% and 0.035 g, 12%) plus unreacted dimethylamino starting material (0.100 g, 25%). Samples of the desired title product were combined and chromatographed on silica gel eluting with 20% acetone in EtOAc to yield 0.1458 g of the title product as a white solid. TLC R$_f$=0.14 (silica gel; 8% MeOH in CH$_2$Cl$_2$); 15% phosphomolybdic acid in EtOH stain.

Melting point=157°-160° C.

EXAMPLE 25

Preparation of
[1S-[1α(βS*,δS*),2α,4aβ,6β,8β,8aα]]-6-(Dimethylamino)-8-(2,2-dimethyl-1-oxobutoxy)decahydro-β,δ-dihydroxy-2-methyl-1-naphthaleneheptanoic acid, monolithium salt

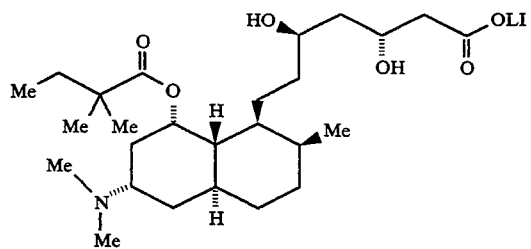

To a solution of the title product prepared in step (b) of Example 24 (0.145 g, 0.32 mmol) in peroxide-free dioxane (4 ml) was added 1N LiOH (0.42 ml, 0.42 mmol). The reaction was stirred for 1 hour at room temperature after which time TLC indicated all of the dimethylamino starting material had been consumed, producing one new spot plus a slight impurity. The solvent was removed in vacuo and the residue was then dissolved in H$_2$O (3 ml) and chromatographed on CHP-20P gel (3 cm×14 cm column) eluting with H$_2$O (200 ml), 5% CH$_3$CN in H$_2$O (100 ml), 10% CH$_3$CN in H$_2$O (100 ml), 15% CH$_3$CN in H$_2$O (100 ml), 20% CH$_3$CN in H$_2$O (300 ml). The desired title compound eluted with 15% CH$_3$CN in H$_2$O. The product fractions were concentrated in vacuo, dissolved in H$_2$O (10 ml) and filtered through a 3.0 μm cellulose nitrate membrane filter (Millipore). The water was removed by freeze drying to give the title product as a white solid (0.1314 g, 88%).

TLC: R$_f$=0.10 (silica gel; 8:1:1 CH$_2$Cl$_2$:MeOH:HOAc); 15% phosphomolybdic acid in EtOH stain. Optical Rotation [α]$_D^{25}$= +62.6° (c=0.50, MeOH)

Elemental Analysis (Microanalysis) for C$_{26}$H$_{46}$NO$_6$.Li.0.63 H$_2$O

| Calc'd | C 64.12 | H 9.78 | N 2.88 |
|---|---|---|---|
| Found | C 64.19 | H 9.87 | N 2.81 |

EXAMPLE 26

Preparation of
[1S-[1α,3α,4aα,7β,8β(2S*,4S*),-8aβ]]-2,2-Dimethylbutanoic acid, 3-(acetylmethylamino)decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-(thioformamido)decahydro-7-methyl-8-[2-[tetrahydro-4-[(phenylmethoxy)methoxy]-6-oxo-2H-pyran-2-yl]-ethyl]-1-naphthalenyl ester

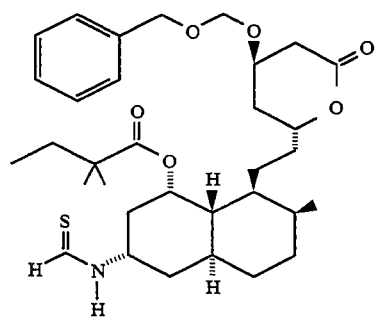

A 0° solution of the formamide (949.3 mg, 1.66 mmol) prepared as the title product in step (a) of Example 18 above in 20 ml toluene was treated with Lawesson's reagent (402.9 mg, 0.996 mmol). After stirring at 0° C. for 15 minutes, the heterogeneous reaction mixture was allowed to warm to ambient temperature and then the reaction mixture was concentrated. The oily solid was chromatographed on Merck silica gel (100:1), eluting with 40% EtOAc/60% hexane. Two rotomers were produced in the reaction and were separated, but fractions containing either rotomer were combined in vacuo and concentrated to a white foam in a yield of 897.6 mg (92%).

(b) [1S-[1α,3α,4aα,7β,8β(2S*,4S*),8aβ]]-2,2-Dimethylbutanoic acid, 3-(methylamino)decahydro-7-methyl-8-[2-[tetrahydro-4-[(phenylmethoxy)methoxy]-6-oxo-2H-pyran-2-yl]-ethyl]-1-naphthalenyl ester

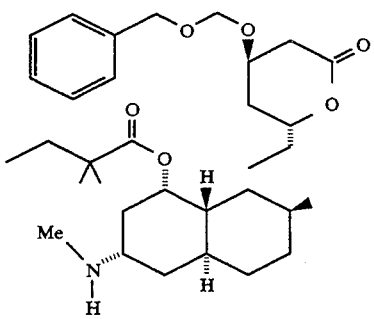

A pale green solution of the thioformamide rotomers (846.8 mg, 1.44 mmol) prepared as the title product in step (a) above and NiCl$_2$·6H$_2$O (1.03 g, 4.32 mmol) in 25 ml MeOH/THF (1:1) was cooled to −20° C. and treated with NaBH$_4$ (327 mg, 8.64 mmol). The solution turned black immediately and bubbled vigorously. The reaction mixture was stirred for 20 minutes at −20° C. and then warmed to 0° C. and stirred for 10 minutes. At this time, the reaction mixture was filtered through a pad of Celite, washing with MeOH. The filtrate was concentrated and the crude product was chromatographed on Merck silica gel (100:1), eluting with 4% MeOH in CH$_2$Cl$_2$ (2 L) and then 5% MeOH in CH$_2$Cl$_2$ (500 ml). The title product was isolated as a colorless oil in a yield of 529.4 mg (66%).

(c) [1S-[1α,3α,4aα,7β,8β(2S*,4S*),8aβ]]-2,2-Dimethylbutanoic acid, 3-(methylacetylamino)decahydro-7-methyl-8-[2-[tetrahydro-4-[(phenylmethoxy)methoxy]-6-oxo-2H-pyran-2-yl]ethyl]-1-naphthalenyl ester

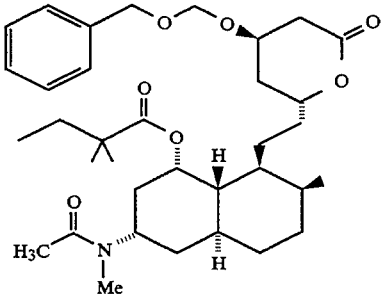

A 0° solution of the methylamine (327.7 mg, 0.588 mmol) prepared as the title product in step (b) above in 7 ml dry CH$_2$Cl$_2$ was treated with Hunigs base (154 μl, 0.881 mmol) followed by acetic anhydride (111 μl, 1.18 mmol). After stirring for 15 minutes, the reaction mixture was diluted with EtOAc and washed with 5% KHSO$_4$, saturated NaHCO$_3$, and brine. The organic layer was dried (Na$_2$SO$_4$), filtered, and the filtrate concentrated. The crude product was chromatographed on Merck silica gel (100:1), eluting with 70% EtOAc/30% hexane (1 L) and 80% EtOAc/20% hexane (100 ml) to give 326.1 mg (93%) of the title product as a colorless oil.

(d) [1S-[1α,3α,4aα,7β,8β(2S*,4S*),8aβ]]-2,2-Dimethylbutanoic acid, 3-(acetyl methylamino)decahydro-7-methyl-8-[2-(tetrahydro-4-hydroxy-6-oxo-2H-pyran-2-yl)ethyl]-1-naphthalenyl ester

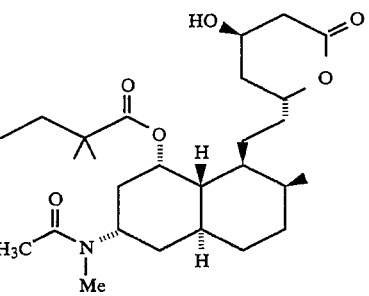

A degassed solution of the acetamide (319.1 mg, 0.532 mmol) prepared as the title product in step (c) above in 6 ml EtOAc was treated with Pd(OH)$_2$—C (65 mg). This mixture was evacuated and filled with H$_2$ via a balloon (repeated 2×). After stirring for 1 hour and 40 minutes, the reaction was approximately 40% complete. More Pd(OH)$_2$—C (30 mg) was added. After stirring for another 2 hours, the reaction was approximately 90% complete. Pd(OH)$_2$—C (20 mg) was added and the reaction mixture was stirred for an additional hour.

The reaction mixture was filtered through Celite and washed with EtOAc followed by MeOH. The filtrate was concentrated, and the crude product was chromatographed on Merck silica gel (100:1), eluting with 2% MeOH in CH$_2$Cl$_2$ (200 ml), 2.5% MeOH in CH$_2$Cl$_2$ (300 ml) and then 3.5% MeOH in CH$_2$Cl$_2$ (600 ml). The title product was isolated as a colorless oil in a yield of 220.4 mg (86%). Rotomers were present as evidenced by $^1$H and $^{13}$C NMR analyses.

EXAMPLE 27

Preparation of
[1S-[1α(βS*,δS*),2α,4aβ,6β,8β,8aα]]-6-(Acetylmethylamino)-8-(2,2-dimethyl-1-oxo-butoxy)decahydro-β,δ-dihydroxy-2-methyl-1-naphthaleneheptanoic acid, monolithium salt

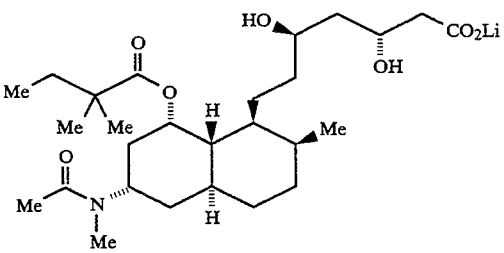

A cooled (ca. 0° C.) solution of the lactone (217.3 mg, 0.453 mmol) prepared as the title product in step (d) of Example 26 above in 1.5 ml dioxane was treated dropwise with 1N LiOH (544 μl, 0.544 mmol).

After 15 minutes of stirring, the reaction mixture was concentrated. The crude product was chromatographed on CHP-20P gel, eluting with H$_2$O (200 ml), 5% CH$_3$CN in H$_2$O (100 ml), 10% CH$_3$CN in H$_2$O (100 ml), 15% CH$_3$CN in H$_2$O (200 ml), 20% CH$_3$CN in H$_2$O (200 ml), and finally 25% CH$_3$CN in H$_2$O (200 ml). Product fractions were concentrated to an oil, which was dissolved in H$_2$O and filtered through a 3.0 μm cellulose nitrate filter. The aqueous filtrate was freeze-dried to give 208.4 mg (91%) of the title product as a white lyophilate. TLC: R$_f$=0.23 on silica gel using 20:1:1 CH$_2$Cl$_2$: MeOH: AcOH); PMA in EtOH stain; [α]$_D$ = +23.4° (c=0.50, MeOH).

Elemental Analysis (%) for C$_{27}$H$_{46}$NO$_7$Li.1.13 H$_2$O.

|   | Calc. | Found |
|---|-------|-------|
| C | 61.90 | 61.87 |
| H | 9.28  | 9.56  |
| N | 2.67  | 2.70  |

EXAMPLE 28

Preparation of [1S-[1α,3α,4aα,7β,8β(2S*,4S*), 8aβ]]-2,2-Dimethylbutanoic acid, 3-[(trifluoroacetyl)methylamino]decahydro-7-methyl -8-[2-(tetrahydro-4-hydroxy-6-oxo -2H-pyran-2-ylethyl]-1-naphthalenyl ester (a) [1S-[1α,3α,4aα,7β,8β(S*,4S*),8aβ]]-2,2-Dimethylbutanoic acid, 3-[(trifluoroacetyl)methylamino]decahydro-7-methyl-8-[2-[tetrahydro-4-[(phenylmethoxy)methoxy]-6-oxo-2H-pyran-2-yl]-ethyl]1-naphthalenyl ester

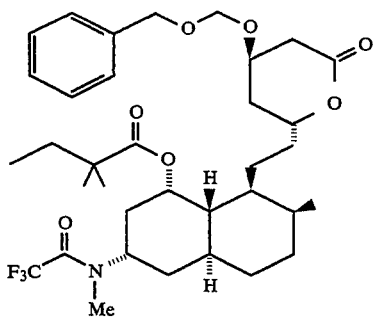

A 0° C. solution of the methylamine title product (258.4 mg, 0.463 mmol) prepared in step (b) of Example 26 above in 6 ml dry CH$_2$Cl$_2$ was treated with Hunigs base (9.68 μl, 0.566 mmol) followed by trifluoroacetic anhydride (98.2 μl, 0.695 mmol).

After stirring for 15 minutes, the reaction mixture was partitioned between 5% KHSO$_4$ and EtOAc. The organic layer was then washed with half-saturated NaHCO$_3$ and brine, dried (Na$_2$SO$_4$), filtered, and concentrated. The crude product was chromatographed on Merck silica gel (100:1), eluting with 25% EtOAc in hexane (500 ml) and then 30% EtOAc in hexane (200 ml) to give 266.3 mg (88%) of the title product as a colorless oil.

(b) [1S-[1α,3α,4aα,7β,8β(S*,4S*),8aβ]]-2,2-Dimethylbutanoic acid, 3-[(trifluoroacetyl)methylamino]decahydro-7-methyl -8-[2-(tetrahydro-4-hydroxy-6-oxo-2H-pyran-2-yl)ethyl]-1-naphthalenyl ester

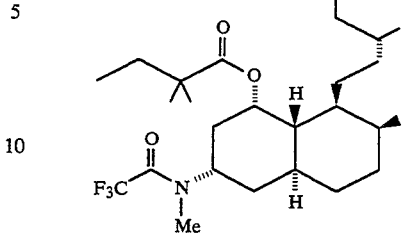

A degassed solution of the trifluoroacetamide (264.6 mg, 0.402 mmol) prepared in step (a) above in 6 ml EtOAc was treated with Pd(OH)$_2$/C (55 mg). The flask was evacuated and filled with hydrogen via a balloon (repeated 2×). After stirring for 1 hour, the reaction mixture was filtered through a pad of Celite, washing with EtOAc and then some MeOH. The filtrate was concentrated. The crude reaction mixture was chromatographed several times with mixtures of EtOAc/hexanes and MeOH/CH$_2$Cl$_2$ but pure title product was not obtained. The title product was isolated in slightly impure form as a colorless oil in a yield of >165 mg.

EXAMPLE 29

Preparation of [1S-[1α(βS*,δS*),2α,4aβ,6β,8β,8aα]]-8-(2,2-Dimethyl-1-oxobutoxy)decahydro-β,δ-dihydroxy-2-methyl-6-(methylamino)-1-naphthaleneheptanoic acid, monolithium salt

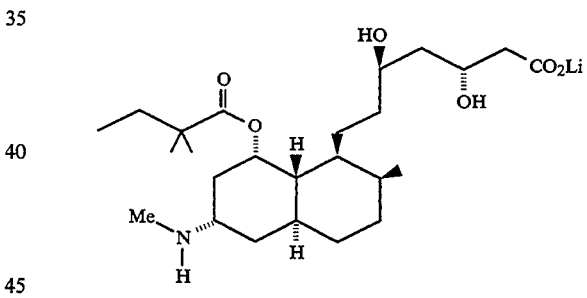

A 0° C. cooled solution of the hydroxylactone title product (160.0 mg, 0.300 mmol) of step (b) of Example 28 above in 1.5 ml dioxane was treated dropwise with 1N LiOH (720 μl, 0.720 mmol). After stirring for one hour and 40 minutes at room temperature, hydrolysis was not complete. 1N LiOH (75 μl, 0.075 mmol) was added and stirred for 1.25 hours. More 1N LiOH (75 μl, 0.075 mmol) was added. After stirring for 30 minutes, the reaction was nearly complete. The reaction mixture was stored at −40° C. overnight. The reaction mixture was warmed to ambient temperature. After stirring for 1 hour, the reaction mixture was concentrated. The crude product was chromatographed on CHP-20P gel, eluting with H$_2$O (225 ml), 5% CH$_3$CN in H$_2$O (400 ml), 10% CH$_3$CN in H$_2$O (200 ml), 15% CH$_3$CN in H$_2$O (200 ml), and finally 20% CH$_3$CN in H$_2$O (100 ml). Fractions containing the title product were combined and concentrated. The concentrate was dissolved in H$_{2O}$, and the aqueous solution was filtered through a 3.0 μm cellulose nitrate filter. The filtrate was freeze-dried to give 163.0 mg (100%) of pure title product as a white lyophilate. [α]$_D^{25}$= +51.4° (c=0.50, MeOH); TLC:

$R_f=0.24$ on silica gel using 8:1:1 $CH_2Cl_2$:MeOH:-HOAc); PMA in EtOH stain.

Elemental Analysis (%) for $C_{25}H_{44}NO_6 \cdot 0.90H_2O$

|   | Calc. | Found |
|---|---|---|
| C | 62.86 | 62.90 |
| H | 9.66 | 9.88 |
| N | 2.93 | 2.89 |

EXAMPLE 30

Preparation of
[1S-[1α,3α,4aα,7β,8β(2S*,4S*),8aβ]]-2,2-Dimethylbutanoic acid,
3-(diethylamino)decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-(diethylamino)decahydro-7-methyl-8-[2-[tetrahydro-4-[(phenylmethoxy)methoxy]]-6-oxo-2H-pyran-2-yl]-ethyl]-1-naphthalenyl ester

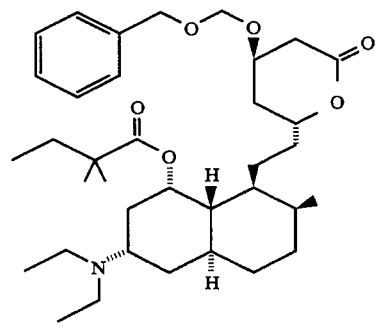

A solution of amine (431.5 mg, 0.794 mmol) prepared as the title product of step (b) of Example 1 above in 4 ml DMF was treated with Hunigs base (276 μl, 1.58 mmol) followed by 2-iodoethane (1.27 ml, 15.9 mmol). Although the reaction was incomplete after stirring for 6 days, the reaction mixture was worked-up. The reaction mixture was diluted with EtOAc, and washed with $H_2O$ (3×), 5% sodium thiosulfate, and brine. The organic layer was dried ($Na_2SO_4$) and filtered, and the filtrate was concentrated. The crude product was chromatographed on Merck silica gel (60:1), eluting with 10% acetone in EtOAc (300 ml), 15% acetone in EtOAc (200 ml), and then 25% acetone in EtOAc (100 ml). The first few fractions collected contained purely the diethyl amine title product. The majority of the fractions containing the desired product also contained the monoethyl product. These mixed fractions were rechromatographed on Merck silica gel (100:1), eluting with 5% acetone in EtOAc (300 ml), 10% acetone in EtOAc (200 ml), and 25% acetone in EtOAc. Fractions containing only the diethyl amine title product were combined with those above and concentrated in vacuo to give 185.7 mg (39%) of a very pale yellow, viscous oil. TLC (silica gel; 1:3 acetone: EtOAc); $R_f=0.24$; PMA stain.

(b) [1S-[1α,3α,4aα,7β,8β(2S*,4S*),8aβ]]-2,2-Dimethylbutanoic acid, 3-(diethylamino)decahydro-7-methyl-8-[2-(tetrahydro-4-hydroxy -6-oxo-2H-pyran-2-yl)ethyl]-1-naphthalenyl ester

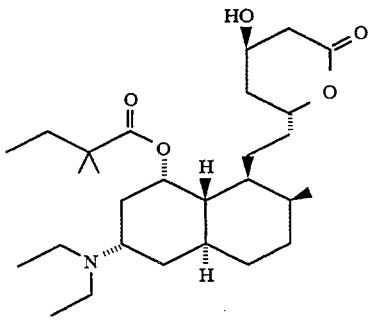

To a solution of the BOM-lactone title product (374.7 mg, 0.625 mmol) of step (a) above in 6.0 ml dry tetrahydrofuran (THF) under argon was added 1N HCl (656 μl, 0.656 mmol). After stirring for 5 minutes, Pd(OH)-2—C (75 mg) was added. The flask containing this mixture was evacuated and filled with $H_2$ via a balloon (repeated 2×). After 1 hour, more 1N HCl (656 μl, 0.656 mmol), and Pd(OH)$_2$—C (20 mg) were added. After stirring for 5 hours, the reaction mixture was diluted with EtOAc and saturated $NaHCO_3$ (aq) was added. This mixture was thoroughly mixed and then filtered through celite, washing with EtOAc. The filtrate was transferred to a separatory funnel, and the aqueous layer was drained off. The organic layer was washed with brine, dried ($Na_2SO_4$), filtered, and the filtrate concentrated. The crude product was chromatogaphed on Merck silica gel (100:1), eluting with EtOAc (200 ml) and then 5% acetone in EtOAc 200 ml). Product fractions were combined and concentrated in vacuo to give 159.8 mg (53%). A very minor impurity (higher $R_f$) was observed by TLC analysis. The material was rechromatographed on Merck silica gel (100:1), eluting with 3% MeOH in $CH_2Cl_2$ (100 ml), 4% MeOH in $CH_2Cl_2$ (200 ml), 5% MeOH in $CH_2Cl_2$ (100 ml), and then 10% MeOH in $CH_2Cl_2$ (100 ml). Fractions containing the alcohol title product were combined and concentrated in vacuo to give 132.6 mg (44%) of a colorless oil. TLC (silica gel; 1:3 acetone: EtOAc): $R_f=0.11$; PMA stain.

EXAMPLE 31

Preparation of
[1S-[1α(βS*,δS*),2α,4aβ,6β,8β,8aβ]]-6-(Diethylamino)-8-(2,2-dimethyl-1-oxobutoxy)decahydro-β,δ-dihydroxy-2-methyl-1-naphthaleneheptanoic acid, monolithium salt

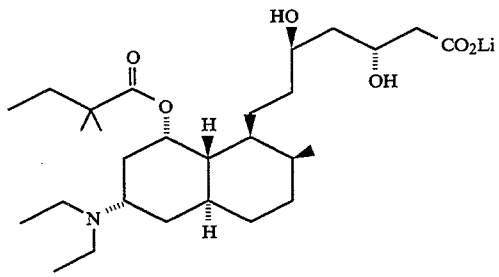

A solution of the hydroxylactone title product of step (b) of Example 30 above (129.2 mg, 0.269 mmol) in 700 μl of dioxane at approximately 0° C. was treated with 1N LiOH (377 μl, 0.377 mmol). The cooling bath was immediately removed. The reaction mixture was stirred for 30 minutes and then concentrated. The oily residue was chromatographed on CHP-20P gel, eluting with H₂O (200 ml), followed by a stepwise gradient of CH₃CN/H₂O mixtures: 5% CH₃CN in H₂O (50 ml), 10% (100 ml), 15% (200 ml), 20% (200 ml) and then 30% (100 ml). Product fractions were combined and concentrated. The residual oil was taken up in H₂O and filtered through a 3.0 μm cellulose nitrate filter. The aqueous solution was freeze-dried to give the title product in a yield of 125.3 mg (92%) as a white lyophilate.

TLC (silica gel; 8:1:1 CH₂Cl₂: MeOH:AcOH): R$_f$=0.10; PMA stain Opt. Rot.: [α]$_D$ = +63.3° (c=0.50, MeOH)

Elemental Analysis (%) for C₂₈H₅₀NO₆Li.0.15 H₂O

|   | Calc. | Found |
|---|-------|-------|
| C | 66.42 | 66.14 |
| H | 10.01 | 10.00 |
| N | 2.77  | 3.05  |

EXAMPLE 32

Preparation of
[1S-[1α,3α,4aα,7β,8β(2S*,4S*),8aβ]]-2,2-Dimethylbutanoic acid,
3-[(2-hydroxyethyl)methylamino]decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-[(2-hydroxyethyl)methylamino]decahydro-7-methyl-8-[2-[tetrahydro-4-[(phenylmethoxy)methoxy]-6-oxo-2H-pyran-2-yl]ethyl]-1-naphthalenyl ester

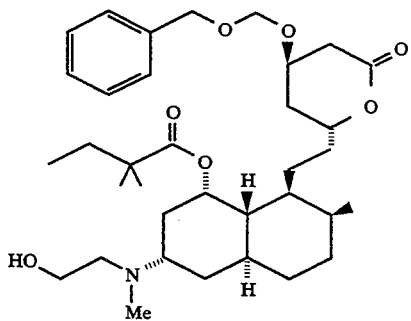

A solution of the methyl amine title product of step (b) of Example 26 above (248.5 mg, 0.446 mmol) in 2 ml DMF was treated with Hunigs base (77.4 μl, 0.444 mmol) followed by 2-iodoethanol (1.0 ml, 2.2 g, excess). After stirring for 75 hours, the reaction mixture was diluted with EtOAc, and washed with H₂O (3x), 5% sodium thiosulfate, and brine. The organic layer was dried (Na₂SO₄) and filtered, and the filtrate was concentrated. The crude product was chromatographed on Merck silca gel (100:1), eluting with 4% MeOH in CH₂Cl₂ (200 ml), 5% MeOH in CH₂Cl₂ (300 ml), and then 10% MeOH in CH₂Cl₂ (100 ml). Product fractions were combined and concentrated in vacuo to give 203.1 mg (76%) of the ethanol-methyl amine title product. TLC (silica gel; 6:1:1 CH₂Cl₂: MeOH:AcOH): R$_f$=0.46; PMA stain.

(b) [1S-[1α,3α,4aα,7β,8β(2S*,4S*),8aβ]]-2,2-Dimethylbutanoic acid, 3-[(2-hydroxyethyl)methylamino]decahydro-7-methyl-8-[2-(tetrahydro-4-hydroxy-6-oxo-2H-pyran-2-yl )ethyl]-1-naphthalenyl ester

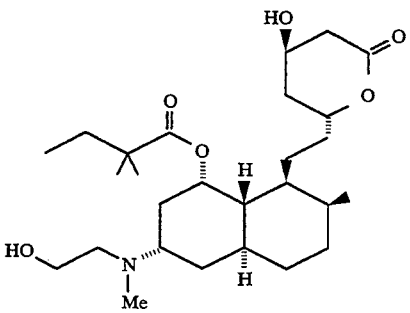

To a degassed solution of the BOM-lactone title product of step (a) above (142.2 mg, 0.236 mmol) in 2.5 ml dry THF was added Pd(OH)₂/C (30 mg). The flask containing the reaction mixture was evacuated and filled with H₂ via a balloon (repeated 2x). To this mixture was added 1N HCl (248 μl, 0.248 mmol). After stirring for 40 minutes, no reaction was observed by TLC analysis. More 1N HCl (248 μl, 0.248 mmol) and Pd(OH)₂/C (ca. 30 mg) were added. After stirring for 4 hours, the reaction was approximately 50% complete. The reaction mixture was diluted with EtOAc and saturated NaHCO₃ (ag) was added. This mixture was filtered through Celite, washing with EtOAc, and the filtrate was transferred to a separatory funnel. The Celite was washed with MeOH, and the MeOH filtrate was concentrated. The residue was taken up in EtOAc, and the solution was transferred to the separatory funnel (above). The two layers were separated, and the organic layer was dried (Na₂SO₄) and filtered. The filtrate was concentrated to 118 mg and stored overnight at −40° C. The reaction mixture was again subjected to hydrogenolysis conditions by dissolving the mixture in 2.5 ml THF and then treating with 1N HCl (248 μl, 0.248 mmol) followed by Pd(OH)₂—C (ca. 30 mg). The flask containing this mixture was briefly evacuated and filled with H₂ (repeated 2x). After stirring for 3 hours, the reaction was complete. The reaction mixture was worked up in the same manner as described above. The crude product was chromatographed on Merck silica gel (100:1), eluting with 5% MeOH in CH₂Cl₂ (200 ml), 10% MeOH in CH₂Cl₂ (200 ml), and then 10% MeOH in CH₂Cl₂ +1% concentrated NH₄OH (200 ml). Fractions containing the alcohol title product were combined and concentrated in vacuo to give 60.2 mg (53%).

EXAMPLE 33

Preparation of
[1S-[1α(βS*,δS*),2α,4aβ,6β,8β,8aα]]-8-(2,2-Dimethyl-1-oxobutoxy)decahydro-β,δ-di-hydroxy-6-[(2-hydroxyethyl)methylamino]-2-methyl-1-naphthaleneheptanoic acid, monolithium salt

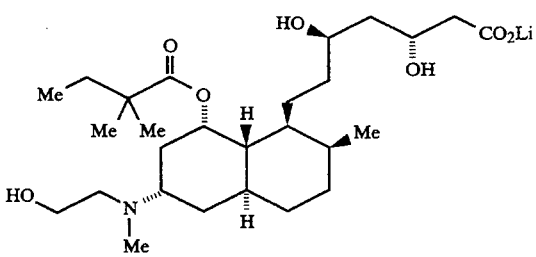

A solution of the hydroxylactone title product of step (b) of Example 32 above (117.7 mg, 0.244 mmol) in 800 μl of dioxane at ca. 0° C. was treated with 1N LiOH (342 μl, 0.342 mmol). After stirring for 15 minutes, the reaction mixture was concentrated. The crude product was chromatographed on CHP-20P gel, eluting with H₂O (200 ml), followed by a stepwise gradient of CH₃CN/H₂O mixtures: 5% CH₃CN in H₂O (200 ml), 10% (200 ml), 15% (300 ml), and then 20% (200 ml). Fractions containing pure product were combined and concentrated. The residual oil was taken up in H₂O, and filtered through a 3.0 μm cellulose nitrate filter. The aqueous solution was freeze-dried to give the title product in a yield of 94.5 mg (77%) as a white lyophilate. TLC (silica gel; 8:1:1 CH₂Cl₂:MeOH:AcOH): R$_f$=0.05; PMA in EtOH stain. Opt. Rot.: [α]$_D$= +68.1° (c=0.50, MeOH)

Elemental Analysis (%) for C₂₇H₄₈NO₇·Li·0.47 H₂O

|   | Calc. | Found |
|---|-------|-------|
| C | 63.08 | 62.99 |
| H | 9.60  | 9.88  |
| N | 2.72  | 2.81  |

EXAMPLE 34

Preparation of
[1S-[1α,3α,4aα,7β,8β(2S*,4S*),8aβ]]-2,2-Dimethylbutanoic acid,
3-aminodecahydro-7-methyl-8-[2-(tetrahydro-4-hydroxy-6-oxo-2H-pyran-2-yl)ethyl]-1-naphthalenyl ester

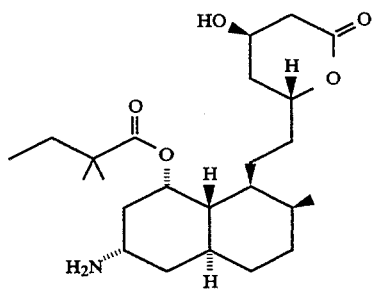

A solution of the amine (895 mg, 1.65 mmol) prepared as the title product of step (b) of Example 1 in 20 ml dry THF was treated with 1N HCl (1.73 ml, 1.73 mmol). After stirring for 5 minutes, Pd(OH)₂—C (180 mg) was added. The flask containing this mixture was evacuated and H₂ was introduced via a balloon. This procedure was repeated two more times. After stirring under H₂ for 30 minutes, no significant reaction had occurred. More 1N HCl 1.73 ml, 1.73 mmol) was added. After 20 minutes very little product formation was observed. More Pd(OH)₂—C (a small spatula tipful) was added. After stirring for another hour, reaction was ~60% complete. More Pd(OH)₂—C (approximately same amount as second addition) was added. After stirring for another hour, the reaction mixture was filtered through filter paper. The filtrate was partitioned between saturated NaHCO₃ (aq) and EtOAc. The two layers were separated. The aqueous layer was extracted with EtOAc. The organic layers were washed with H₂O and brine, dried (Na₂SO₄), and filtered through a pad of MgSO₄. The filtrate was concentrated, and the crude product was chromatographed on Merck silica gel (100:1), eluting with 5% MeOH in CH₂Cl₂ (500 ml) followed by 10% MeOH in CH₂Cl₂ (2L). Fractions containing the desired title product were combined and concentrated to yield 344.5 mg (49%).

EXAMPLE 35

Preparation of
[1S-[1α,3α,4aα,7β,8β(2S*,4S*),8aβ]]-2,2-Dimethylbutanoic acid,
3-(dimethylamino)decahydro-7-methyl-8-[2-(tetrahydro-4-hydroxy-6-oxo-2H-pyran-2-yl)ethyl]-1-naphthalenyl ester

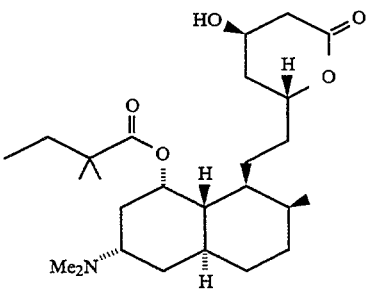

and

[1S-[1α(βS*,δS*),2α,4aβ,6β,8β,8aα]]-8-(2,2,-Dimethyl-1-oxobutoxy)decahydro-β,δ-dihydroxy-2-methyl-6-(dimethylamino)-1-napthaleneheptanoic acid, methyl ester

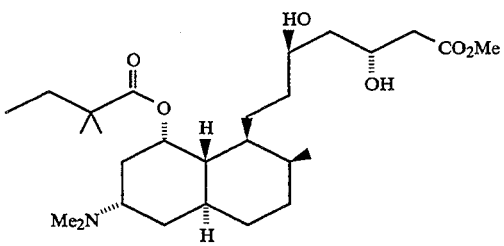

To a solution of aqueous formaldehyde (37% in H₂O, 1.2 ml, 15.6 mmol) in MeOH (6 ml) was added Pd(OH)₂—C (55 mg) and then a solution of the amine lactone title product of Example 34 above (263.8 mg, 0.623 mmol) in 4 ml MeOH, plus 2 ml MeOH rinse. The flask containing the mixture was briefly evacuated and H₂ was introduced via a balloon.

The reaction mixture was stirred for 1.5 hours and then was filtered through a pad of Celite, washing with MeOH. After concentration, the crude reaction mixture was taken up in EtOAc and washed with saturated NaHCO₃, H₂O and brine. The organic layer was dried (Na₂SO₄) and filtered through a pad of MgSO₄. The filtrate was concentrated. The crude product was chromatographed on Merck silica gel (100:1), eluting with 5% MeOH in CH₂Cl₂ (200 ml), 10% MeOH in CH₂Cl₂ (500 ml), and 20% MeOH in CH₂Cl₂ (200 ml). A second component (lower Rf) was observed in most of the fractions collected.

1st set of fractions: 42.6 mg
2nd set of fractions: 244.8 mg

The 1st set of fractions contained the above methyl ester and lactone title products.

The ¹H NMR spectrum of fraction 2 was very similar to that of the above 1st set of fractions but showed the presence of one other compound, which could have been starting material. The 2nd set of fractions was resubjected to reductive methylation conditions again: A solution of aqueous formaldehyde (1.2 ml, 15.6 mmol) in MeOH (6 ml) was treated with Pd(OH)₂—C (55 mg) and then a solution of the compounds of the 2nd set of fractions in 4 ml MeOH (plus 3×1 ml MeOH rinses). The flask containing this mixture was evacuated and filled with H₂ via a balloon. After 1 hour, the reaction mixture was worked up similarly to that described above. The reaction mixture was chromatographed on Merck silica gel (100:1), eluting with 5% MeOH in CH₂Cl₂ (200 ml), 10% MeOH in CH₂Cl₂ (500 ml) and 20% MeOH in CH₂Cl₂ (100 ml). Product fractions were combined and concentrated in vacuo to give 170.5 mg of a mixture of lactone and methyl ester title products as a colorless oil.

EXAMPLE 36

Preparation of
[1S-[1α,3α,4aα,7β,8β(2S*,4S*),8aβ]]-2,2-Dimethylbutanoic acid,
3-(dimethylamino)decahydro-7-methyl-8-[2-(tetrahydro-4-hydroxy-6-oxo-2H-pryan-2-yl)ethyl]-1-naphthalenyl ester

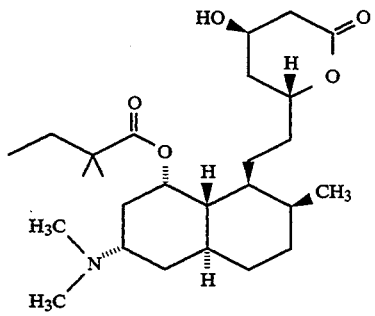

The following is an alternative procedure for obtaining the dimethylamino hydroxylactone title product of Example 35. By conducting the following procedure, which is a modification of the procedure described in Example 24, the aforementioned lactone was obtained without the formation of the methyl ester which was obtained concurrently with the lactone in Example 35.

The procedure conducted for the present Example was identical to that described in Example 24, steps (a) and (b), with the following exception: the trifluoroacetic acid employed in Example 24, step (b) was replaced by 1N HCl in the present Example. This modification provided the desired title product in 54% yield after 6.5 h.

EXAMPLE 37

Preparation of
[1S-[1α,3α,4aα,7β,8β(2S*,4S*),8aβ]]-2,2-Dimethylbutanoic acid,
3-(trimethylammonio)decahydro-7-methyl-8-[2-(tetrahydro-4-hydroxy-6-oxo-2H-pyran-2-yl)ethyl]-1-naphthalenyl ester, iodide

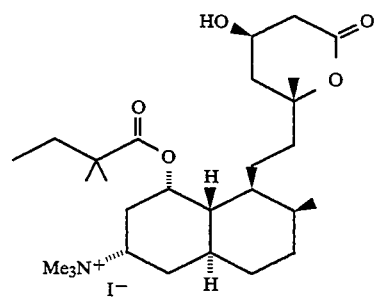

and

[1S-[1α(βS*,δS*),2α,4aβ,6β,8β,8aα]]-8-(2,2-Dimethyl-1-oxobutoxy)decahydro-β,δ-dihydroxy-2-methyl-6-(trimethylammonio)-1-naphthaleneheptanoic acid, methyl ester, iodide

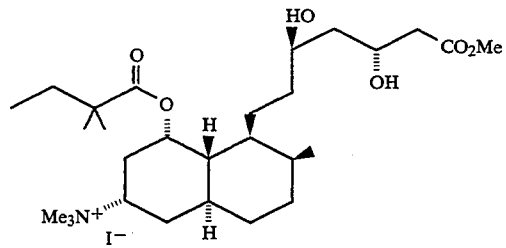

A suspension of the dimethylamine lactone and dimethyl ester title products of Example 35 above (205.7 mg, 0.455 mmol) in 2 ml CH₃CN was treated with methyl iodide (CH₃I, 991 μl, 15.9 mmol). Immediately upon addition of the methyl iodide, all the material dissolved. After stirring for 17.5 hours, the reaction mixture was concentrated in vacuo. The title product was obtained as a very pale yellow fluffy solid in a yield of 267.8 mg (99%) and was used in Example 38 without purification.

EXAMPLE 38

Preparation of
[1S-[1α(βS*,δS*),2α,4aβ,6β,8β,8aα]]-8-(2,2-Dimethyl-1-oxobutoxy)decahydro-β,δ-dihydroxy-2-methyl-6-(trimethylammonio)-1-naphthaleneheptanoic acid, hydroxide, monolithium salt

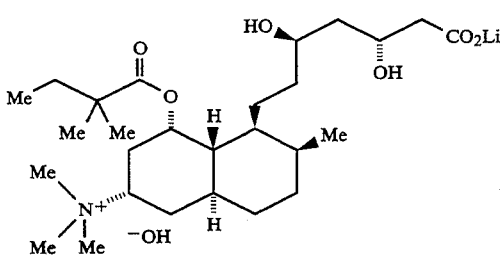

A solution of the hydroxylactone title product of Example 37 above (260.3 mg, 0.439 mmol) in 1.5 ml dioxane and 0.5 ml H₂O was treated dropwise with 1N LiOH (439 μl, 0.439 mmol). After stirring for 1 hour, more 1N LiOH (439 μl, 0.439 mmol) was added to ensure complete reaction.

The reaction mixture was concentrated. The crude product was chromatographed on CHP-20P gel, eluting with H₂O (200 ml), followed by a step-wise gradient of CH₃CN in H₂O mixtures: 5% (50 ml), 10% (100 ml), 15% (100 ml), and 20% (200 ml), and 30% (100 ml). Product fractions were combined and concentrated. The residual oil was taken up in H₂O and filtered through a 3.0 μm cellulose nitrate filter. The aqueous solution was freeze-dried to give 207.8 mg (93%) of the title product as a white lyophilate.

TLC: $R_f$=0.18 (silica gel; 8:2:1 isopropanol: conc. NH₄OH: H₂O); PMA in EtOH stain.

Opt. Rot.: $[\alpha]_D$=+64.1° (c=0.50, MeOH)

Elemental Analysis (%) for $C_{27}H_{50}NO_7Li \cdot 1.19\ H_2O$

|   | Calc. | Found |
|---|-------|-------|
| C | 61.29 | 61.16 |
| H | 9.98  | 9.97  |
| N | 2.65  | 2.78  |

EXAMPLE 39

Preparation of
[1S-[1α,3α,4aα,7β,8β(2S*,4S*),8aβ]]-2,2-Dimethylbutanoic acid,
3-[[4-[(trifluoroacetyl)amino]benzoyl]amino]decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-[[4-[(trifluoroacetyl)amino]-benzoyl]amino]decahydro-7-methyl-8-[2-[tetrahydro-4-[(phenylmethoxy)methoxy]-6-oxo-2H-pyran-2-yl]ethyl]-1-naphthalenyl ester

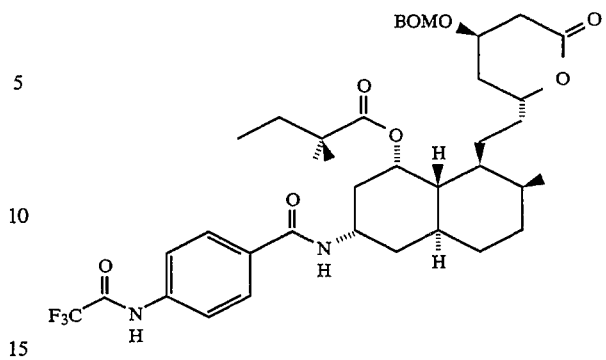

Preparation of p-(trifluoroacetylamino)benzoic acid

A solution of p-aminobenzoic acid in MeOH (500 mg, 3.65 mmol) was treated with 1.0 eq triethylamine (3.65 mmol, 509 μl) followed by 1.1 eq trifluoroacetic acid, ethyl ester (4.015 mmol, 478 μl). The solution was stirred overnight. The solution was diluted with EtOAc, washed with 5% KHSO₄, followed by brine. The solution was dried over MgSO₄ and solvent was removed by evaporation. The residue was purified by recrystallization in EtOAc/Hexane to afford eggshell-colored glossy plates (265 mg (31%), C₉H₆F₃NO₃).

Amide Formation

A solution of the BOM-amine title product of step (b) of Example 1 above (320 mg, 0.59 mmol) in THF was treated with the p-(trifluoroacetylamino)benzoic acid prepared above (1.1 eq, 0.65 mmol, 151.45 mg), 1.1 eq hydroxybenzotriazole hydrate (HOBT) (0.65 mmol, 87.5 mg) and the solution was cooled to 0° C. and stirred for 15 minutes. 1.1 eq 1-(3-Dimethylaminopropyl)-3-ethylcarbodiimide hydrochloride (EDC) (0.65 mmol, 124.3 mg) was added and the solution was warmed to room temperature and stirred overnight. The solution was added to EtOAc/5% KHSO₄. The organic layer was washed with brine, dried over MgSO₄, and solvent was removed by evaporation. The residue was purified on SiO₂ using 60% EtOAc/40% Hexane as the mobile phase. The title product was obtained as a white solid (yield=198 mg, 0.26 mmol (44% theory)). C₄₁H₅₃F₃N₂O₈.

(b) [1S-[1α,3α,4aα,7β,8β(2S*,4S*),8aβ]]-2,2-Dimethylbutanoic acid, 3-[[4-[(trifluoroacetyl)amino]-benzoyl]amino]decahydro-7-methyl-8-[2-(tetrahydro-4-hydroxy-6-oxo-2H-pyran-2-yl)ethyl]-1-naphthalenyl ester

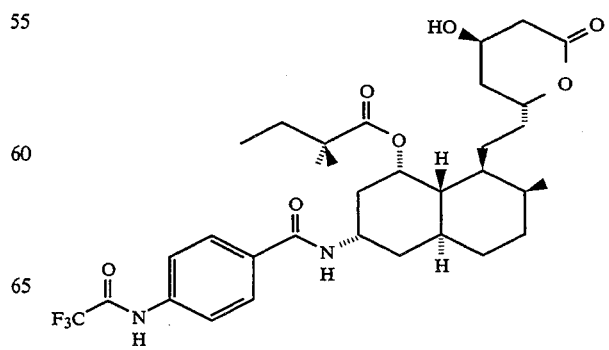

An EtOAc solution of the benzamide title product prepared in step (a) above (198 mg, 0.26 mmol) was treated with excess AcOH (~2 ml) and treated with Pd(OH)$_2$/C. H$_2$ gas was vigorously bubbled through the solution. The solution was filtered and treated with trifluoroacetic acid (TFA) (~½ ml) and fresh Pd(OH)$_2$/C. H$_2$ gas was bubbled vigorously. The reaction was followed by TLC. The solution was diluted with EtOAc and filtered through filter paper. The solution was washed with NaHCO$_3$, brine and dried over MgSO$_4$. The solution was filtered and the solvent was removed by EtOAc. The residue was purified by SiO$_2$ column chromatography using 75% EtOAc, 28% Hexane. The title product (C$_{33}$H$_{45}$F$_3$N$_2$O$_7$ was obtained as a colorless oil (yield=154 mg, % theory=91%.)

EXAMPLE 40

Preparation of
[1S-[1α(βS*,δS*),2α,4aβ,6β,8β,8aα]]-6-[(4-Aminobenzoyl)amino]-8-(2,2-dimethyl-1-oxo-butoxy)decahydro-β,δ-dihydroxy-2-methyl-1-naphthaleneheptanoic acid, monolithium salt

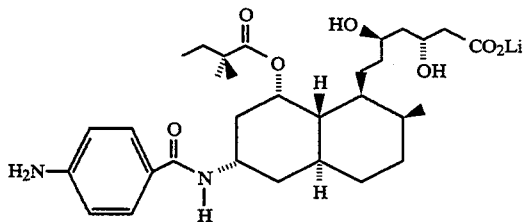

A solution of the lactone title product prepared in step (b) of Example 39 above (154 mg, 0.24 mmol) in CH$_3$CN:H$_2$O (10:1) was treated with 1N LiOH (0.723 mmol, 723 μl) and stirred for 2 hours. The solvent was reduced by evaporation and the residue purified on CHP-20 resin using 1) H$_2$O to remove LiOH
2) 20% CH$_3$CN/H$_2$O as the mobile phase.

The solution was concentrated and filtered through a 3 μm Whatman membrane filter. The solution was lyophilized. The title product was obtained as a white lyophilate (116 mg, % theory=83%) C$_{31}$H$_{47}$N$_2$O$_7$·Li·1.49 H$_2$O TLC: R$_f$=0.45 on SiO$_2$ using 8:1:1 (CH$_2$Cl$_2$:MeOH: AcOH): developed using a 10% solution of phosphomolybdic acid in ethanol.

Elemental Analysis (%) for C$_{31}$H$_{47}$N$_2$O$_7$Li·1.49 H$_2$O

|   | Calc. | Found |
|---|-------|-------|
| C | 62.73 | 62.81 |
| H | 8.49  | 8.71  |
| N | 4.72  | 4.64  |

Opt. Rot.: [α]$_D$= +114° (c=0.36, MeOH)

EXAMPLE 41

Preparation of
[1S-[1α,3α,4aα,7β,8β(2S*,4S*),8aβ]]-2,2-Dimethylbutanoic acid, 3-[[[(trifluoroacetyl)amino]acetyl]amino]decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-[[[(trifluoroacetyl)amino]acetyl]amino]decahydro-7-methyl-8-[2-[tetrahydro-4-[(phenylmethoxy)methoxy]-6-oxo-2H-pyran-2-yl]ethyl]-1-naphthalenyl ester

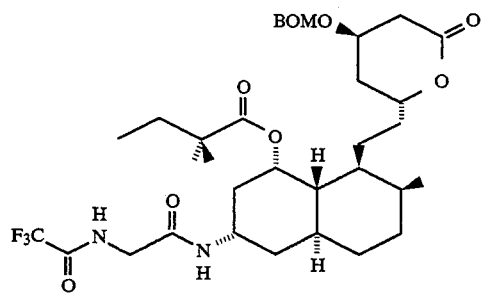

A solution of the BOM-amine title product of step (b) of Example 1 above (340 mg, 0.625 mmol) in THF was treated with 1 eq HOBT (0.625 mmol, 84.5 mg) and 1.2 eq of the carboxylic acid (trifluoroacetylamino)acetic acid (0.75 mmol, 128.3 mg). The solution was stirred for 15 minutes. The solution was then cooled to 0° C. and stirred for 15 minutes; 1 eq of EDC was added (0.625 mmol, 120 mg) and the solution was allowed to warm to room temperature and stir overnight. The solution was partitioned between 5% aq. KHSO$_4$ and EtOAc. The organic fraction was washed with brine, dried over MgSO$_4$, filtered and solvent was removed by evaporation. No purification was performed. The title product was obtained in a colorless oil. Yield: 332 mg, 0.476 mmol, % theor.=76%.

(b) [1S-[1α,3α,4aα,7β,8β(2S*,4S*),8aβ]]-2,2-Dimethylbutanoic acid, 3-[[[(trifluoroacetyl)amino]acetyl]amino]decahydro-7-methyl-8-[2-(tetrahydro-4-hydroxy-6-oxo-2H-pyran-2-yl)ethyl]-1-naphthalenyl ester

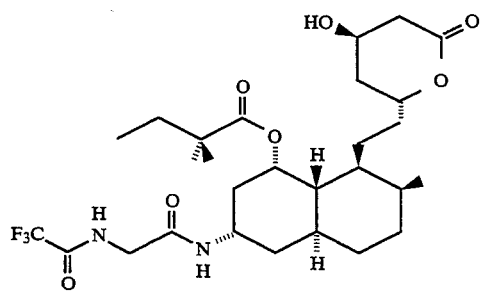

The amide title product prepared in step (a) above (332 mg, 0.476 mmol) was dissolved in EtOAc and treated with an excess of AcOH (2 ml), followed by Pd(OH)$_2$/C. The solution was bubbled vigorously with H$_2$ gas for ¾ h. The solution was filtered through a short pad of Celite. The solution was partitioned between EtOAc and saturated aq. NaHCO$_3$. The organic was washed with brine and dried over MgSO$_4$, filtered and solvent was removed by evaporation. No purification was performed. The title product was obtained in a white foam. (Yield: 272 mg, 0.472; % theor: 99%). C$_{28}$H$_{43}$N$_2$O$_7$F$_3$).

EXAMPLE 42

Preparation of
[1S-[1α(βS*,δS*),2α,4aβ,6β,8β,8aα]]-6-[(Aminoacetyl-)amino]-8-(2,2-dimethyl-1-oxo-butoxy)decahydro-β,δ-dihydroxy-2-methyl-1-naphthaleneheptanoic acid, monolithium salt

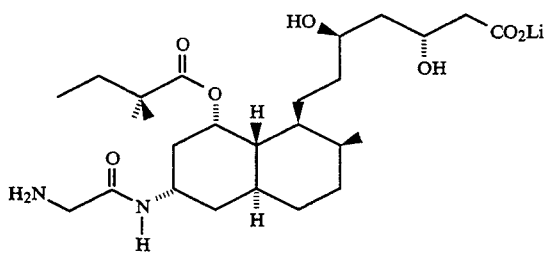

A solution of the amide-alcohol prepared as the title product in step (b) of Example 41 above (272 mg 0.472 mmol) was dissolved in $CH_3CN/H_2O$ (~10:1) and treated with 1N LiOH (1.42 mmol, 1.42 mL) and stirred for 3 hours. The organic solvent was removed by evaporation and the residue was purified on CHP-20P resin using 1) $H_2O$, 2) 20% $CH_3CN/H_2O$. The solution was reduced by evaporation, filtered through a 3 μm Whatman filter membrane, and lyophilized to give the title product as a fluffy white solid. Yield: 214 mg, theory: 90%). $C_{26}H_{45}N_2O_7Li.0.63$ $H_2O$ Opt. Rot.: $[α]_D = +50.8°$ (c=0.50, MeOH), TLC: $R_f=0.35$ on $SiO_2$ using 8:1:1 ($CH_2Cl_2$:MeOH:AcOH): developed using a 10% solution of phosphomolybdic acid in ethanol.

Elemental Analysis (%) for $C_{26}H_{45}N_2O_7Li.0.63$ $H_2O$

|   | Calc. | Found |
|---|-------|-------|
| C | 60.53 | 60.71 |
| H | 9.04  | 9.23  |
| N | 5.43  | 5.25  |

EXAMPLE 43

Preparation of
[1S-[1α,3α,4aα,7β,8β(2S*,4S*),8aβ]]-2,2-Dimethylbutanoic acid, 3-[[(dimethylamino)acetyl]amino]decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-[[(dimethylamino)acetyl]amino]decahydro-7-methyl-8-[2-[tetrahydro-4-[(phenylmethoxy)methoxy]-6-oxo-2H-pyran-2-yl]ethyl]-1-naphthalenyl ester

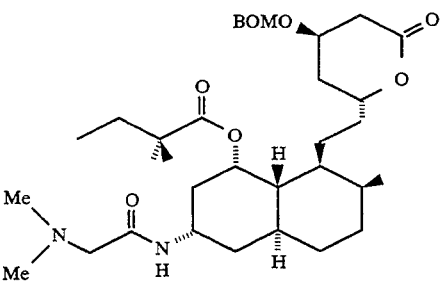

A solution of the BOM-amine title product of step (b) of Example 1 above (200 mg, 0.368 mmol) in DMF was treated with 1.1 eq. N,N-dimethyl glycine hydrochloride (0.405 mmol, 51 mg), followed by 1.1 eq Hunigs base (0.405 mmol, 64 μl). The reaction mixture was stirred for 10 minutes, and was then treated with 1.1 eq HOBT (0.405 mmol, 55 mg). The mixture was stirred another 10 minutes. The solution was cooled to 0° C. and treated with 1.1 eq. EDC (0.405 mmol, 78 mg). The reaction was allowed to warm to room temperature and was stirred for 24 hours.

The solution was partitioned between EtOAc and $H_2O$. The $H_2O$ layer was extracted 3× with EtOAc. The EtOAc layers were combined and washed with 1) $KHSO_4$ 5%, 2) $NaHCO_3$, 3) brine. The organic solution was dried over $MgSO_4$, filtered and the solvent was removed by evaporation. The residue was purified on $SiO_2$ using 65% EtOAc/35% Hexane as the mobile phase. The title product was obtained as a colorless oil (Yield: 100 mg, % theory=43% ).

(b) [1S-[1α,3α,4aα,7β,8β(2S*,4S*), 8aβ]]-2,2-Dimethylbutanoic acid, 3-[[(dimethylamino)acetyl]amino]decahydro-7-methyl-8-[2-(tetrahydro-4-hydroxy-6-oxo-2H-pyran-2-yl)ethyl]-1-naphthalenyl ester

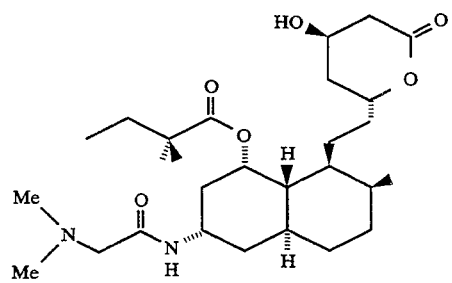

A solution of the BOM-amide prepared as the title product in step (a) above (200 mg, 0.32 mmol) in EtOAc was treated with an excess of AcOH (2 ml) followed by $Pd(OH)_2$/C. The solution was degassed with argon, followed by vigorously bubbled $H_2$. TLC indicated no reaction. Trifluoroacetic acid was added (½ ml) along with more $H_2$, and the reaction proceeded rapidly. The solution was filtered through a very short pad of Celite. The solution was washed with $NaHCO_3$ (sat. aq.) followed by NaCl (sat. aq.). The organic fraction was dried over $MgSO_4$, and solvent was removed by evaporation. No further purification was performed. The title product was obtained as a pale yellow oil. Yield: 150 mg, % theory= ~90%).

EXAMPLE 44

Preparation of
[1S-[1α(βS*,δS*),2α,4aβ,6β,8β,8aα]]-6-[[(Dimethylamino)acetyl]amino]-8-(2,2-dimethyl-1-oxobutoxy)-decahydro-β,δ-dihydroxy-2-methyl-1-naphthaleneheptanoic acid, monolithium salt

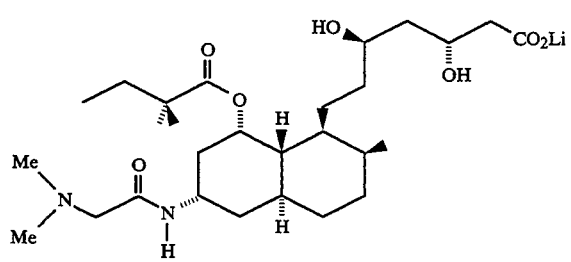

A solution of the dimethyl amino acetamide prepared as the title product in step (b) of Example 43 above (150 mg, 0.295 mmol) was dissolved in $CH_3CN/H_2O$ and treated with 1N LiOH (0.590 mmol, 590 μl) and was stirred for 2 hours. The acetonitrile was removed by evaporation and the residue was purified by column chromatography using CHP-20P as the stationary phase and
1) 7% $CH_3CN/H_2O$ (no product)
2) 10% $CH_3CN/H_2O$ (no product)
3) 17% $CH_3CN/H_2O$ (title product)
4) 20% $CH_3CN/H_2O$ (title product)
as the gradient mobile phase. The title product was obtained as a white lyophilate (Yield: 100 mg, % theory: 64%).

Elemental Analysis (%) for $C_{28}H_{49}N_2O_7Li \cdot 1.36 H_2O$

|   | Calc. | Found |
|---|-------|-------|
| C | 60.36 | 60.54 |
| H | 9.36  | 9.37  |
| N | 5.03  | 4.85  |

TLC: $R_f$=0.40 on $SiO_2$ using 8:1:1 ($CH_2Cl_2$:MeOH:AcOH): developed using a 10% solution of phosphomolybdic acid in ethanol. Opt. Rot.: $[α]_D$=+58.9° (c=0.52, MeOH)

EXAMPLE 45

Preparation of
[1S-[1α,3α,4aα,7β,8β(2S*,4S*),8aβ]]-2,2-Dimethylbutanoic acid,
3-[[[(2-hydroxyethyl)[2-(acetyloxy)ethyl]amino]acetyl]amino]decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-[[[(2-hydroxyethyl)[-2(acetyloxy)ethyl]amino]acetyl]amino]decahydro-7-methyl-8-[2-[tetrahydro-4-[(phenylmethoxy)methoxy]-6-oxo-2H-pyran-2-yl]ethyl]-1-naphthalenyl ester

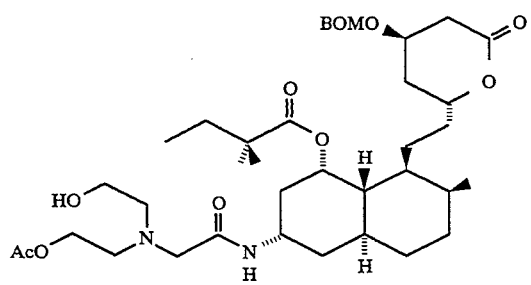

Preparation of bicine lactone reagent:

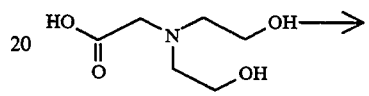

To a suspension of bicine, N,N-bis(2-hydroxyethyl)glycine (1 g, 6.12 mmol) in pyridine (3 eq, 18.4 mmol, 1.48 ml) was added acetic anhydride (3 eq, 18.4 mmol, 1.74 ml). The solution became clear after ~½ hours of stirring at room temperature. The solution was stirred for 2 hours. The solution was diluted with $H_2O$, treated with $Na_2CO_3$ (ag. sat.) and extracted with EtOAc. The organic layer was washed with 5% aq. $KHSO_4$ followed by brine, and dried over $MgSO_4$. The solvent was removed by evaporation to give the above bicine lactone as a colorless oil (Yield: ~645 mg, % theory: ~60%).

Amide Formation

A solution of the BOM-amine title product of step (b) of Example 1 above (300 mg, 0.55 mmol) was treated with the bicine-lactone reagent prepared above (0.12 mmol, 155 mg) in benzene under argon and was heated at reflux for 24 hours. The solvent was removed by evaporation and the residue was purified by $SiO_2$ chromatography using 80% ethyl acetate, 20% hexane as the mobile phase to give the title product ($C_{40}H_{62}N_2O_{10}$) as a colorless oil. (Yield: 381 mg, % theory: 64%).

(b) [1S-[1α,3α,4aα,7β,8β(2S*,4S*),8aβ]]-2,2-Dimethylbutanoic acid, 3-[[[(2-hydroxyethyl)[-2(acetyloxy)ethyl]amino]acetyl]amino]decahydro-7-methyl-8-[2-(tetrahydro-4-hydroxy-6-oxo-2H-pyran-2-yl)ethyl]-1-naphthalenyl ester

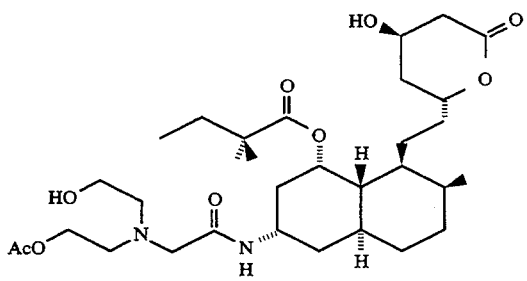

A solution of the bicine-amide prepared as the title product in step (a) above (381 mg, 0.52 mmol) was treated with AcOH, excess (~2 mls) followed by Pd(OH)$_2$/C and bubbled vigorously with H$_2$ gas. TLC indicated no reaction, so excess trifluoroacetic acid (~½ ml) was added with fresh Pd(OH)$_2$/C and H$_2$ gas was bubbled through. The solution was filtered through a fluted filter paper in EtOAc. The solution was washed with Na$_2$CO$_3$, brine and dried over MgSO$_4$. The solution was filtered and solvent was removed by evaporation. Purification on SiO$_2$ column chromatography using 3% MeOH, 97% CH$_2$Cl$_2$ as the mobile phase yielded the title product as a colorless oil. Yield: 147 mg, % theory: 46% (C$_{32}$H$_{54}$N$_2$O$_9$).

EXAMPLE 46

Preparation of [1S-[1α(βS*,δS*),2α,4aβ,6β,8β,8aα]]-6-[[[Bis(2-hydroethyl)amino]acetyl]amino]-8-(2,2-dimethyl-1-oxobutoxy)decahydro-β,δ-dihydroxy-2-methyl-1-naphthaleneheptanoic acid, monolithium salt

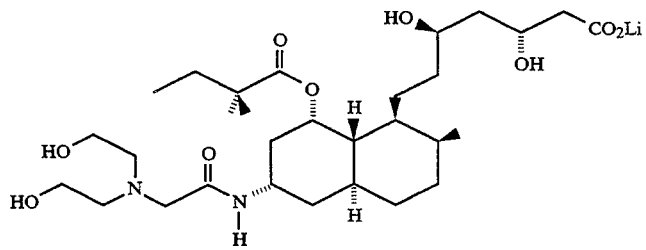

A solution of the lactone title product of step (b) of Example 45 above (147 mg, 0.24 mm) in CH$_3$CN:H$_2$O (~10:1) was treated with 1N LiOH (0.72 mmol, 720 μl) and was stirred for 2 hours. The solution was concentrated and the residue purified on CHP-20P gel using
1) H$_2$O
2) 20% CH$_3$CN/H$_2$O The solution was concentrated, filtered through a 3 μm Whatman membrane filter, and lyophilized to obtain the title product as a white lyophilate (Yield: 90 mg; % theory: 64%). Opt. Rot.: [α]$_D$=+47.9° (c=0.33, MeOH) TLC: R$_f$=0.30 on SiO$_2$ using 8:1:1(CH$_2$Cl$_2$:MeOH: AcOH): developed using a 10% solution of phosphomolybdic acid in ethanol.

Elemental Analysis (%) for C$_{30}$H$_{53}$N$_2$O$_9$Li.0.62 H$_2$O

|   | Calc. | Found |
|---|-------|-------|
| C | 59.67 | 59.58 |
| H | 9.05  | 9.16  |

-continued

|   | Calc. | Found |
|---|-------|-------|
| N | 4.64  | 4.73  |

EXAMPLE 47

Preparation of [1S-[1α(βS*,δS*),2α,4aβ,6β,8β,8aα]]-6-(Dimethylamino)-8-(2,2-dimethyl-1-oxobutoxy)decahydro-β,δ-dihydroxy-2-methyl-1-naphthalenheptanoic acid, N-oxide, monolithium salt

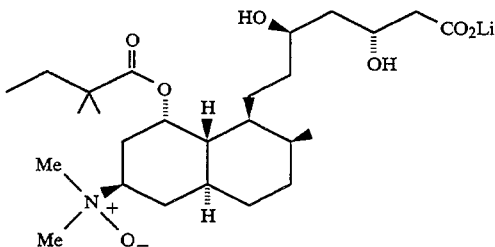

To a solution of the dimethylamino title product of step (b) of Example 24 above (0.270 g, 0.598 mmol) in THF (8 ml) cooled to 0° C. was added m-chloroperoxybenzoic acid (m-CPBA) (0.232 g of ~80%, 1.1 mmol). After stirring the reaction under argon in an ice water bath for 0.5 h, TLC indicated that the N-oxide had formed. After 1 h 1N LiOH (1.7 ml) was added to the ice cold reaction. The saponification was complete in 1.5 hours as indicated by TLC. The reaction was then concentrated in vacuo at room temperature to 1-2 ml and then chromatographed on CHP-20P gel (3 cm × 14 cm) eluting with H$_2$O (300 ml), 10% CH$_3$CN in H$_2$O (1 l), 20% CH$_3$CN in H$_2$O (400 ml). The product eluted in the 10% CH$_3$CN fractions. The fractions containing product were combined and rechromatographed on CHP-20P gel (3 cm × 16 cm) eluting with H$_2$O (300 ml), 5% CH$_3$CN in H$_2$O (400 ml), 10% CH$_3$CN in H$_2$O (400 ml), 15% CH$_3$CN in H$_2$O (300 ml). The product eluted in the 10–15% fractions. The product fractions were combined, concentrated in vacuo, dissolved in H$_2$O (10 ml), filtered through a 3 μm Whatman membrane filter and freeze dried to yield 157.9 mg (0.321 mmol) of the title product as a white solid, 54%. A second product fraction was obtained affording 30.2 mg (0.061 mmol), 10%. The second fraction was not combined with the first. C$_{26}$H$_{46}$NO$_7$Li.1.01 H$_2$O Opt. Rot.: [α]$_D$=+82.2° (c=0.50, MeOH) TLC: R$_f$=0.28 (Silica Gel, CH$_2$Cl$_2$:MeOH:HOAc 7.6:1.2:1.1) PMA in EtOH stain.

Elemental Analysis (%) for C$_{26}$H$_{46}$NO$_7$Li.1.01 H$_2$O

| | Calc. | Found |
|---|---|---|
| C | 61.25 | 61.50 |
| H | 9.49 | 9.78 |
| N | 2.79 | 2.50 |

EXAMPLE 48

Preparation of
[1S-[1α,3α,4aα,7β,8β(2S*,4S*),8aβ]]-2,2-Dimethylbutanoic acid,
3-(1-pyrrolidinyl)decahydro-7-methyl-8-[2-(tetrahydro-4-hydroxy-6-oxo-2H-pyran-2-yl)ethyl]-1-naphthalenyl ester (a) [1S-[1α,3α,4aα,7β,8β(2S*,4S*),8aβ]]-2,2-Dimethylbutanoic acid, 3-(1-pyrrolidinyl)decahydro-7-methyl-8-[2-[tetrahydro-4-[(phenylmethoxy)methoxy]-6-oxo-2H-pyran-2-yl]ethyl]-1-naphthalenyl ester

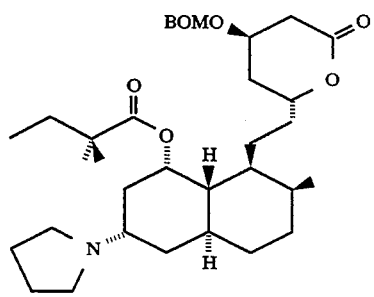

A solution of the BOM-amine prepared as the title product in step (b) of Example 1 above (100 mg, 0.184 mmol) was dissolved in CH₂Cl₂ and treated with Hunigs base (0.522 mmol, 96 μl) followed by 1,4-dibromobutane (0.276 mmol, 33–40 μl). The solution was placed under argon and stirred at room temperature for 3 days. The solution was partitioned between EtOAc and H₂O. The organic fraction was washed with 5% KHSO₄ followed by Na₂CO₃ and NaCl (sat., aq.). The solution was dried over MgSO₄, filtered and solvent was removed by evaporation. The compound was purified by SiO₂ chromatography using 5% MeOH in CH₂Cl₂ to obtain the title product as a colorless oil (Yield: 64 mg, % theory: 58%).

(b) [1S-[1α,3α,4aα,7β,8β(2S*,4S*),8aβ]]-2,2-Dimethylbutanoic acid, 3-(1-pyrrolidinyl)decahydro-7-methyl-8-[2-(tetrahydro-4-hydroxy-6-oxo-2H-pyran-2-yl)ethyl]-1-naphthalenyl ester

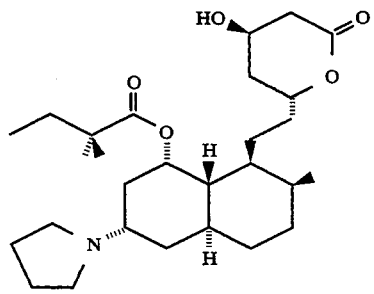

A number of combined fractions from various runs which contained the BOM pyrrolidine prepared as the title product in step (a) above (410 mg, 0.687 mmol, slightly impure) were dissolved in THF and treated with 1 eq. 1.0N HCl (687 μl), followed by Pd(OH)₂/C and H₂ gas. Another portion of 1N HCl aq. (100 μl) was added to facilitate the reaction. The solution was filtered through filter paper and diluted with EtOAc. The solution was washed with saturated NaHCO₃, brine and dried over MgSO₄. The residue was not purified further. TLC: 8:1:1 CH₂Cl₂:MeOH:AcOH. The title product was obtained (C₂₈H₄₇NO₅, yield: 280 mg, % theory: 75%).

EXAMPLE 49

Preparation of
[1S-[1α(βS*,δS*),2α,4aβ,6β,8β,8aα]]-8-(2,2-Dimethyl-1-oxobutoxy)decahydrao-β,δ-dihydroxy-2-methyl-6-(1-pyrrolidinyl)-1-naphthaleneheptanoic acid, monolithium salt

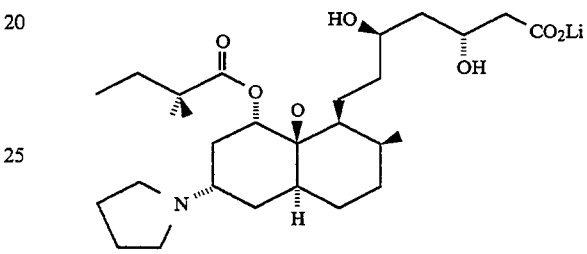

A solution of the pyrrolidine lactone prepared as the title product in step (b) of Example 48 above (280 mg, 0.59 mmol) was dissolved in CH₃CN/H₂O (20/1) and was treated with 2 eq LiOH (1N, 1.17 ml). The solution was stirred for 2 hours and solvent was removed by evaporation. The residue was subjected to CHP-20P chromatography using 1) H₂O to remove LiOH and 2) 10–20% gradient to remove product (CH₃CN/H₂O). The organic solvent was removed and the aqueous solution was lyophilized overnight to yield the title product as a white lyophilate (Yield: 78 mg). C₂₈H₄₈NO₆Li.1.00 H₂O Opt. Rot.: [α]$_D$=+63.9° (c=0.33, MeOH) TLC: R$_f$=0.30 (SiO₂ using 8:1:1 CH₂Cl₂:MeOH:AcOH): developed using a 10% solution of phosphomolybdic acid in ethanol.

Elemental Analysis (%) for C₂₈H₄₈NO₆Li.1.00 H₂O

| | Calc. | Found |
|---|---|---|
| C | 64.71 | 64.67 |
| H | 9.70 | 9.74 |
| N | 2.70 | 2.74 |

What we claim is;
1. A compound having the following formula I:

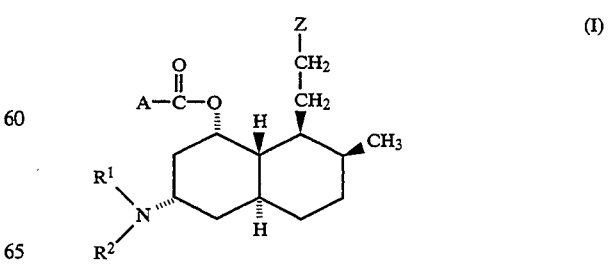

where
A is alkyl or aryl;

Z is the open chain moiety:

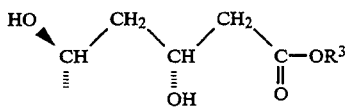

or Z is the lactone moiety:

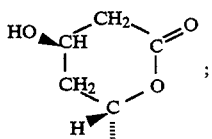

(i) $R^1$ and $R^2$ are each independently selected from:
(1) hydrogen;
(2) unsubstituted or substituted alkyl;
(3) aryl;
(4) acyl;
(5) $R^5$—$SO_2$—;
(6) $(R^4)(R^6)N$—$SO_2$—;
(7) $(R^4)(R^6)N$—$SO$—;

(8) $(R^4)(R^6)N-\underset{\underset{NR^7}{\parallel}}{C}-$;

(9) $(R^4)(R^6)N$—$C(O)$—;
(10) $(R^5)O$—$C(O)$—;
(11) alkenyl;
(12) alkynyl;
(13) carbocyclo; or
(14) $R^5$—$SO$—; or (ii) $R^1$ and $R^2$, together with the nitrogen atom to which they are bonded, form a heterocyclo group wherein said nitrogen atom is the sole ring heteroatom;

$R^3$ is:
(1) hydrogen;
(2) a pharmaceutically acceptable cation; or
(3) a moiety which, together with the atoms to which it is bonded, forms a pharmaceutically acceptable ester group;

$R^4$ and $R^6$ are each independently selected from:
(1) hydrogen;
(2) alkyl;
(3) aryl;
(4) carbocyclo;
(5) alkenyl; or
(6) alkynyl;

$R^5$ is selected from:
(1) alkyl;
(2) aryl;
(3) carbocyclo;
(4) alkenyl; or
(5) alkynyl; and $R^7$ is selected from:
(1) hydrogen;
(2) alkyl;
(3) aryl;
(4) cyano;
(5) nitro; or
(6) —$COOR^5$;

and N-oxides and/or salts thereof.

2. The compound of claim 1, wherein A is:

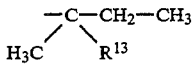

where $R^{13}$ is hydrogen, cycloalkyl, aryl or alkyl.

3. The compound of claim 1, wherein Z is said lactone moiety.

4. The compound of claim 1, wherein Z is said open chain moiety and $R^3$ is hydrogen, alkyl, $NH_4^+$, alkylammonium or an alkali metal.

5. The compound of claim 1, wherein $R^1$ and $R^2$ are independently hydrogen; alkyl wherein said alkyl is (i) unsubstituted lower alkyl; (ii) hydroxy-substituted lower alkyl; (iii) alkoxy-substituted lower alkyl; (iv) lower alkyl substituted by amino or substituted amino groups; (v) $R^5$—$S(O)_m$—$(CH_2)_n$— where n is from 1 to 5, m is 0, 1 or 2, and $R^5$ is alkyl or aryl; (vi) alkylcarbonyloxy-substituted lower alkyl; (vii) aryloxy-substituted lower alkyl; or (viii) arylcarbonyloxy-substituted lower alkyl; $R^5$—$SO_2$— where $R^5$ is unsubstituted lower alkyl; trihalomethylcarbonyl; (trifluoroacetylamino)acetyl; alkylcarbonyl where the alkyl of said alkylcarbonyl is one of the aforementioned alkyl groups (i) through (viii); optionally substituted phenylcarbonyl; $(R^5)O$—$C(O)$— where $R^5$ is unsubstituted lower alkyl; $(R^4)$ $(R^6)N$—$C(O)$— where $R^4$ and $R^6$ are independently hydrogen or unsubstituted lower alkyl; formyl; or $(R^4)$ $(R^6)N$—$SO_2$— where $R^4$ and $R^6$ are independently hydrogen or unsubstituted lower alkyl; or $R^1$ and $R^2$, together with the nitrogen atom to which they are bonded, form an unsubstituted or substituted pyrrolidinyl group.

6. The compound of claim 1, wherein said compound is:

[1S-[1α,3α,4aα,7β,8β(2S*,4S*),8aβ]]-2,2-dimethylbutanoic acid, 3-[(methylsulfonyl)amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)decahydro-β,δ-dihydroxy-2-methyl-6-[(methylsulfonyl)amino]-1-naphthaleneheptanoic acid;

[1S-[1α,3α,4aα,7β,8β(2S*,4S*),8aβ]]-2,2-dimethylbutanoic acid, 3-[[(methylsulfonyl)acetyl]amino]-decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)decahydro-β,δ-dihydroxy-2-methyl-6-[[(methylsulfonyl)acetyl]amino]-1-naphthaleneheptanoic acid;

[1S-[1α,3α,4aα,7β,8β(2S*,4S*),8aβ]]-2,2-dimethylbutanoic acid, 3-[(methoxyacetyl)amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)decahydro-β,δ-dihydroxy-6-[(methylacetyl)amino]-2-methyl-1-naphthaleneheptanoic acid;

[1S-[1α,3α,4aα,7β,8β(2S*,4S*),8aβ]]-2,2-dimethylbutanoic acid, 3-(benzoylamino)decahydro-7-methyl-8-[2-(tetrahydro-4-hydroxy-6-oxo-2H-pyran-2-yl)-ethyl]-1-naphthalenyl ester;

[1S-[1α(βS*,δS*),2α,4aβ,6β,8β,8aα]]-6-(benzoylamino)-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[(acetoxyacetyl)amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4β,6β,8β,8aα]]-8-(2,2-dimethyl-1-oxobutoxy)decahydro-β,δ-dihydroxy-6-[(hydroxyacetyl)amino]-2-methyl-1-naphthaleneheptanoic acid;

[1S-[1α,3α,4aα,7β,8β(2S*,4S*),8aβ]]-2,2-dimethylbutanoic acid, 3-[(trifluoroacetyl)amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-amino-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanonic acid, 3-[(methoxycarbonyl)amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)decahydro-β,δ-dihydroxy-6-[(methoxycarbonyl)amino]-2-methyl-1-naphthaleneptanoic acid;

[1S-[1α(βS*,δS*),2α4aβ,6β,8β,8aα]]-6-[[(methylamino)carbonyl]amino]-8-(2,2-dimethyl-1-oxobutoxy)decahydro-β,δ-dihydroxy-2-methyl-1-naphthaleneheptanoic acid;

[1S-[1α(βS*,δS*),2α,4aβ,6β,8β,8aα]]-6-[[(dimethylamino)carbonyl]amino]-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-(acetylamino)decahydro-7-methyl-8-[2-(tetrahydro-4-hydroxy-6-oxo-2H-pyran-2-yl)ethyl]-1-naphthalenyl ester;

1S-[1α(βS*,δS*),2α,4aβ,6β,8β,8aα]]-6-acetylamino)-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-(formylamino)decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)-6-(formylamino)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[[(dimethylamino)sulfonyl]amino]decahydro-7-methyl-8-[2-(tetrahydro-4-hydroxy-6-oxo-2H-pyran-2-yl)ethyl-1-naphthalenyl ester;

[1S-[1α(βS*,δS*),2α,4aβ,6β,8β,8aα]]-6-[[(dimethylamino)sulfonyl]amino]-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[[(methylamino)sulfonyl]amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-8-(2,2-dimethyl-1-oxobutoxy)decahydro-β,δ-dihydroxy-2-methyl-6-[[(methylamino)sulfonyl]amino]-1-naphthaleneheptanoic acid;

[1S-[1α,3α,4aα,7β,8β(2S*,4S*),8aβ]]-2,2-dimethylbutanoic acid, 3-(dimethylamino)decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-dimethylamino)-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-(acetylmethylamino)decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-(acetylmethylamino)-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[(trifluoroacetyl)methylamino]decahydro-7-methyl-8-[2-(tetrahydro-4-hydroxy-6-oxo-2H-pyran-2-yl)ethyl]-1-naphthalenyl ester;

[1S-[1α(βS*,δS*),2α4aβ,6β,8β,8aα]]-8-(2,2-dimethyl-1-oxobutoxy)decahydro-β,δ-dihydroxy-2-methyl-6-(methylamino)-1-naphthaleneheptanoic acid;

[1S-[1α,3α,4aα,7β,8β(2S*,4S*),8aβ]]-2,2-dimethylbutanoic acid, 3-(diethylamino)decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-(diethylamino)-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[(2-hydroxyethyl)methylamino]decahydro-7-methyl-8-[2-(tetrahydro-4-hydroxy-6-oxo-2H-pyran-2-yl)ethyl]-1-naphthalenyl ester;

[1S-[1α(βS*,δS*),2α4aβ,6β,8β,8aα]]-8-(2,2-dimethyl-1-oxobutoxy)decahydro-β,δ-dihydroxy-6-[(2-hydroxyethyl)methylamino]-2-methyl-1-naphthaleneheptanoic acid;

[1S-[1α,3α,4aα,7β,8β(2S*,4S*),8aβ]]-2,2-dimethylbutanoic acid, 3-aminodecahydro-7-methyl-8-[2-(tetrahydro-4-hydroxy-6-oxo-2H-pyran-2-yl)ethyl)-1-naphthalenyl ester;

[1S-[1α,3α,4aα,7β,8β(2S*,4S*),8aβ]]-2,2-dimethylbutanoic acid, 3-(dimethylamino)decahydro-7-methyl-8-[2-(tetrahydro-4-hydroxy-6-oxo-2H-pyran-2-yl)ethyl]-1-naphthalenyl ester;

[1S-[1α,3α,4aα,7β,8β(2S*,4S*),8aβ]]-2,2-dimethylbutanoic acid, 3-(dimethylamino)decahydro-7-methyl-8-[2-(tetrahydro-4-hydroxy-6-oxo-2H-pyran-2-yl)-ethyl)-1-naphthalenyl ester;

[1S-[1α,3α,4aα,7β,8β(2S*,4S*),8aβ]]-2,2-dimethylbutanoic acid, 3-(trimethylammonio)decahydro-7-methyl-8-[2-(tetrahydro-4-hydroxy-6-oxo-2H-pyran-2-yl)ethyl]-1-naphthalenyl ester, iodide;

[1S-[1α(βS*,δS*),2α,4aβ,6β,8β,8aα]]-8-(2,2-dimethyl-1-oxobutoxy)decahydro-β,δ-dihydroxy-2-methyl-2-methyl-6-(trimethylammonio)-1-naphthaleneheptanoic acid, methyl ester, iodide;

[1S-[1α(βS*,δS*),2α,4aβ,6β,8β,8aα]]-8-(2,2-dimethyl-1-oxobutoxy)decahydro-β,δ-dihydroxy-2-methyl-6-(trimethylammonio)-1-naphthaleneheptanoic acid, hydroxide;

[1S-[1α,3α,4aα,7β,8β(2S*,4S*),8aβ]]-2,2-dimethylbutanoic acid, 3-[[4-[(trifluoroacetyl)amino]benzoyl]amino]decahydro-7-methyl-8-[2-(tetrahydro-4-hydroxy -6-oxo-2H-pyran-2-yl)-ethyl]-1-naphthalenyl ester;

[1S-[1α,(βS*,δS*),2α,4aβ,6β,8β,8aα]]-6-[(4-aminobenzoyl)amino]-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[[[(trifluoroacetyl)amino]acetyl- ]amino]decahydro-7-methyl-8-[2-(tetrahydro-4-hydroxy -6-oxo-2H-pyran-2-yl)-ethyl]-1-naphthalenyl ester;

[1S-[1α(βS*,δS*),2α,4aβ,6β,8β,8aα]]-6-[(aminoacetyl)amino]-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[[(dimethylamino)acetyl]amino]-decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-[[(dimethylamino)acetyl]amino]-8-(2,2-dimethyl-1-oxobutoxy)decahydro-β,δ-dihydroxy-2-methyl-1-naphthaleneheptanoic acid;

[1S-[1α,3α,4aα,7β,8β(2S*,4S*),8aβ]]-2,2-dimethylbutanoic acid, 3-[[[(2-hydroxyethyl)[2(acetyloxy)ethyl]amino]acetyl]amino]decahydro-7-methyl-8-[2-(tetrahydro-4-hydroxy-6-oxo-2H-pyran-2-yl)ethyl]-1-naphthalenyl ester;

[1S-[1α(βS*,δS*),2α,4aβ,6β,8β,8aα]]-6-[[[bis(2-hydroxyethyl)amino]acetyl]amino]-8-(2,2-dimethyl-1-oxobutoxy)decahydro-β,δ-dihydroxy-2-methyl-1-naphthaleneheptanoic acid;

[1S-[1α(βS*,δS*),2α,4aβ,6β,8β,8aα]]-6-(dimethylamino)-8-(2,2-dimethyl-1-oxobutoxy)decahydro-β,δ-dihydroxy-2-methyl-1-1-naphthaleneheptanoic acid, N-oxide;

[1S-[1α,3α,4aα,7β,8β(2S*,4S*),8aβ]]-2,2-dimethylbutanoic acid, 3-(1-pyrrolidinyl)decahydro-7-methyl-8-[2-(tetrahydro-4-hydroxy-6-oxo-2H-pyran-2-yl)ethyl]-1-naphthalenyl ester; or

[1S-[1α(βS*,δS*),2α,4aβ,6β,8β,8aα]]-8-(2,2-dimethyl-1-oxobutoxy)decahydro-β,δ-dihydroxy-2-methyl-6-(1-pyrrolidinyl)-1-naphthaleneheptanoic acid; or a pharmaceutically acceptable salt thereof.

7. A compound having the following formula II:

(II)

where A is alkyl or aryl;
$Z^a$ is

; and $Pro^1$ is a protecting group which may be cleaved to form a hydroxyl group without destruction of the remainder of the molecule; or a salt thereof.

8. A compound having the following formula:

where
A is alkyl or aryl;
$Z^a$ is $Pro^1$ is a protecting group which may be cleaved to form a hydroxyl group without destruction of the remainder of the molecule;
(i) $R^1$ and $R^2$ are each independently selected from:
(1) hydrogen;
(2) alkyl;
(3) aryl;
(4) acyl;
(5) $R^5$—$SO_2$—;
(6) $(R^4)(R^6)N$—$SO_2$—;
(7) $(R^4)(R^6)N$—SO—;

(8) $(R^4)(R^6)N$—C—;
       ‖
       $NR^7$ (9) $(R^4)(R6)N$—C(O)—;
(10) $(R^5)O$—C(O)—;
(11) alkenyl;
(12) alkynyl;
(13) carbocyclo; or
(14) $R^5$—SO—; or (ii) $R^1$ and $R^2$, together with the nitrogen atom to which they are bonded, form a heterocyclo group wherein said nitrogen atom is the sole ring heteroatom;

$R^4$ and $R^6$ are each independently selected from:
(1) hydrogen;
(2) alkyl;
(3) aryl;
(4) carbocyclo;
(5) alkenyl; or
(6) alkynyl;

$R^5$ is selected from:
(1) alkyl;
(2) aryl;
(3) carbocyclo;
(4) alkenyl; or
(5) alkynyl; and $R^7$ is selected from:
(1) hydrogen;
(2) alkyl;
(3) aryl;
(4) cyano;

(5) nitro; or (6) —COOR$^5$;

or an N-oxide or salt thereof.

9. A method for inhibiting the activity of the enzyme HMG-CoA reductase, comprising the step of contacting a compound of claim 1 with said enzyme.

10. A method for the treatment and/or prevention of hypercholesterolemia, comprising the step of administering to a subject in need thereof a compound of claim 1 in an amount effective therefor.

11. A pharmaceutical composition comprising a compound of claim 1, and a pharmaceutically acceptable vehicle or diluent.

* * * * *